US011198672B2

(12) United States Patent
Watanabe et al.

(10) Patent No.: US 11,198,672 B2
(45) Date of Patent: Dec. 14, 2021

(54) COMPOUNDS HAVING S1P5 RECEPTOR AGONISTIC ACTIVITY

(71) Applicant: ONO PHARMACEUTICAL CO., LTD., Osaka (JP)

(72) Inventors: Toshihide Watanabe, Osaka (JP); Kensuke Kusumi, Osaka (JP); Satomi Imaide, Osaka (JP); Toshimitsu Endo, Osaka (JP); Takaki Komiya, Osaka (JP); Naomi Tsuburaya, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/970,865

(22) PCT Filed: Feb. 21, 2019

(86) PCT No.: PCT/JP2019/006637
§ 371 (c)(1),
(2) Date: Aug. 18, 2020

(87) PCT Pub. No.: WO2019/163917
PCT Pub. Date: Aug. 29, 2019

(65) Prior Publication Data
US 2021/0087141 A1 Mar. 25, 2021

(30) Foreign Application Priority Data

Feb. 22, 2018 (JP) .............................. JP2018-029549

(51) Int. Cl.
*C07D 205/04* (2006.01)
*C07C 49/252* (2006.01)
*C07C 49/577* (2006.01)

(52) U.S. Cl.
CPC .......... *C07D 205/04* (2013.01); *C07C 49/252* (2013.01); *C07C 49/577* (2013.01)

(58) Field of Classification Search
CPC .................................................. C07D 205/04
See application file for complete search history.

(56) References Cited

U.S. PATENT DOCUMENTS

| 2007/0167425 | A1 | 7/2007 | Nakade et al. |
| 2009/0275554 | A1 | 11/2009 | Habashita et al. |
| 2012/0190649 | A1 | 7/2012 | Thomas et al. |
| 2017/0327439 | A1* | 11/2017 | Kusumi ................ A61P 13/10 |

FOREIGN PATENT DOCUMENTS

| JP | 2013-501074 A | 1/2013 |
| WO | 2005/020882 A2 | 3/2005 |
| WO | 2006/064757 A1 | 6/2006 |
| WO | 2011/017561 A1 | 2/2011 |
| WO | 2012/109108 A1 | 8/2012 |
| WO | 2016/088834 A1 | 6/2016 |
| WO | 2017/131149 | 8/2017 |

OTHER PUBLICATIONS

Thierry Walzer, et al., "Natural killer cell trafficking in vivo requires a dedicated sphingosine 1-phosphate receptor", Nature Immunology, vol. 8, No. 12, Dec. 2007, pp. 1337-1344.
Supplementary Extended European Search Report dated Jul. 27, 2017 by the European Patent Office in related European Patent Application No. 15865945.8.
Richard N. Hanna, et al., "Patrolling monocytes control tumor metastasis to the lung", Science, Nov. 20, 2015 • vol. 350 Issue 6263, total 7 pages.
Itoh, K. et al., "Synthesis and Biological Activities of 3-Aminomethyl-1,2-dihydronaphthalene Derivatives", Chem. Pharm. Bull., 1983, vol. 31, No. 6, pp. 2006-2015.
Emilie Debien, et al., "S1PR5 is pivotal for the homeostasis of patrolling monocytes", European Journal of Immunology, Molecular immunology, 2013. 43: pp. 1667-1675.
C. Jaillard, et al., "Edg8/S1P5: An Oligodendroglial Receptor with Dual Function on Process Retraction and Cell Survival", The Journal of Neuroscience, Feb. 9, 2005 • 25(6), pp. 1459-1469.
Alexander S. Novgorodov, et al., "Activation of sphingosine-1-phosphate receptor S1P5 inhibits oligodendrocyte progenitor migration", The FASEB Journal, Research Communication, vol. 21, No. 7 , 2017, pp. 1503-1514.
International Search Report (PCT/ISA/210) dated May 21, 2019 by the International Searching Authority in counterpart International Patent Application No. PCT/JP2019/006637.
Office Action dated Jan. 2, 2019 by the United States Patent and Trademark Office in related U.S. Appl. No. 15/532,389.
Office Action dated Aug. 15, 2019 by the United States Patent and Trademark Office in related U.S. Appl. No. 15/532,389.
Office Action dated Jun. 9, 2020 by the United States Patent and Trademark Office in related U.S. Appl. No. 15/532,389.

(Continued)

*Primary Examiner* — John S Kenyon
(74) *Attorney, Agent, or Firm* — Sughrue Mion, PLLC

(57) ABSTRACT

A compound represented by the general formula (V)

wherein all the symbols are as defined in the specification, has an improved balance of the agonist activity against the $S1P_5$ receptor relative to the $S1P_1$ receptor, and can thus serve as a therapeutic agent for $S1P_5$-mediated diseases such as schizophrenia and Binswanger's disease and other neurodegenerative diseases.

3 Claims, No Drawings

(56) References Cited

OTHER PUBLICATIONS

International Search Report (PCT/ISA/210) dated Feb. 23, 2016 issued by the International Searching Authority in related International Application No. PCT/JP2 015/084019.
Written Opinion (PCT/ISA/237) dated Feb. 23, 2016 issued by the International Searching Authority in relatedt International Application No. PCT/JP2 015/084019.
International Searching Authority, International Preliminary Report on Patentability dated Aug. 27, 2020 in Application No. PCT/JP2019/006637, with English translation.

* cited by examiner

COMPOUNDS HAVING S1P5 RECEPTOR AGONISTIC ACTIVITY

CROSS-REFERENCE TO RELATED APPLICATIONS

This application is a National Phase Entry of PCT International Application No. PCT/JP2019/006637 filed Feb. 21, 2019, which claims priority to Japanese Patent Application No. 2018-029549 filed Feb. 22, 2018, the entire contents of which are incorporated by reference herein.

TECHNICAL FIELD

The present invention, in one aspect, relates to a compound represented by general formula (V):

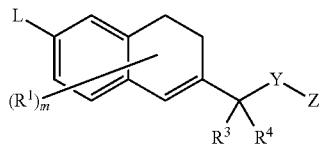

(wherein, all the symbols have the same meanings as described below), or a pharmaceutically acceptable salt thereof (hereinafter occasionally abbreviated as the compound of the present invention).

BACKGROUND ART

Sphingosine-1-phosphate [(2S,3R,4E)-2-amino-3-hydroxyoctadec-4-enyl-1-phosphate; hereinafter occasionally abbreviated as SIP] is a lipid which is synthesized by metabolic turnover of sphingolipids in cells and by the extracellular action of a secreted sphingosine kinase. It is proposed that sphingosine-1-phosphate acts as an intercellular communication mediator as well as an intracellular second messenger.

Among S1P receptors, with regard to $S1P_5$ (EDG-8) receptor, it is known that $S1P_5$ (EDG-8) receptor is highly expressed in oligodendrocytes (oligodendroglia) and oligodendrocyte progenitor cells. It is revealed that $S1P_5$ receptor promotes the induction of differentiation of oligodendrocyte progenitor cells to oligodendrocytes when $S1P_5$ receptor is activated (see Non Patent Literatures 1 and 2). Oligodendrocytes are a kind of glial cells which form the myelin sheaths (myelin) by binding to the axons of nerve cells. Accordingly, it is considered that a compound which has an agonist activity of $S1P_5$ receptor is useful for treating neurodegenerative disease or demyelinating disease such as multiple sclerosis because the compound promotes the regeneration of myelin which has disappeared (demyelination) in nerve cells.

In addition, it is known that $S1P_5$ receptor is highly expressed also in natural killer (NK) cells and it is revealed that the migration of NK cells is induced by the activation of $S1P_5$ receptor (see Non Patent Literature 3).

Further, $S1P_5$ receptor is highly expressed in patrolling monocytes which are known to be involved in the tumor immunity, and therefore, there is a possibility that the activation of the tumor immunity is induced by the activation of $S1P_5$ receptor (see Non Patent Literatures 4 and 5).

On the other hand, $S1P_1$ receptor is a receptor expressed in the cardiovascular system and on lymphocytes. It is known that compounds having an $S1P_1$ receptor agonist activity may have a lymphocyte-lowering effect or a heart-rate lowering effect.

Incidentally, as compounds of prior arts to the present invention, the following compounds are known.

As a dihydronaphthalene compound which has binding abilities to S1P receptors, it is disclosed that a compound represented by general formula (a):

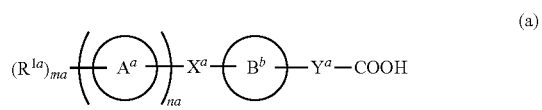

(wherein, ring $A^a$ represents a cyclic group, ring $B^a$ represents a cyclic group which may further have a substituent(s), $X^a$ represents a bond or a spacer having 1 to 8 atoms in its main chain, $Y^a$ represents a bond or a spacer having 1 to 10 atoms in its main chain, na represents 0 or 1, when na is 0, ma represents 1 and $R^{1a}$ represents a hydrogen atom or a substituent, and when na is 1, ma represents 0 or an integer of 1 to 7 and $R^{1a}$ represents a substituent (in which when ma is 2 or more, a plurality of $R^{1a}$ s may be the same or different) (provided that the definition of each of groups is excerpted)) specifically binds, in particular, to EDG-1 ($S1P_1$) receptor and EDG-6 ($S1P_4$) receptor (see Patent Literature 1).

In addition, as a dihydronaphthalene compound which has binding abilities to S1P receptors, it is disclosed that a compound represented by general formula (b):

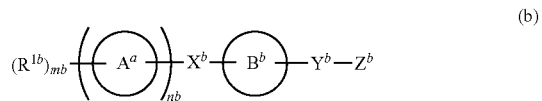

(wherein, ring $A^b$ represents a cyclic group, ring $B^b$ represents a cyclic group which may further have a substituent(s), $X^b$ represents a bond or a spacer having 1 to 8 atoms in its main chain, $Y^b$ represents a bond or a spacer having 1 to 10 atoms in its main chain, $Z^b$ represents an acidic group which may be protected, nb represents 0 or 1, when nb is 0, mb represents 1 and $R^{1b}$ represents a hydrogen atom or a substituent, and when nb is 1, mb represents 0 or an integer of 1 to 7 and $R^{1b}$ represents a substituent (in which when mb is 2 or more, a plurality of $R^{1b}$ s may be the same or different) (provided that the definition of each of groups is excerpted)) binds, in particular, to EDG-1 ($S1P_1$) receptor, EDG-6 ($S1P_4$) receptor and/or EDG-8 ($S1P_5$) receptor (see Patent Literature 2).

With regard to a compound having a dihydronaphthalene skeleton, none of prior arts disclose nor suggest that the compound of the present invention has improved the balance of an $S1P_5$ receptor agonist activity against an $S1P_1$ receptor agonist activity.

CITATIONS LISTS

Patent Literatures

Patent Literature 1: WO 2005/020882 A
Patent Literature 2: WO 2006/064757 A

Non Patent Literatures

Non Patent Literature 1: The Journal of Neuroscience, Vol. 25, No. 6, pages 1459-1469, 2005
Non Patent Literature 2: The FASEB Journal, Vol. 21, pages 01503-1514, 2007
Non Patent Literature 3: Nature Immunology, Vol. 8, No. 12, pages 1337-1344, 2007
Non Patent Literature 4: European Journal of Immunology, Vol. 43, pages 1667-1675, 2013
Non Patent Literature 5: Science, Vol. 350, No. 6263, pages 985-990, 2015

SUMMARY OF INVENTION

Technical Problems

An object of the present invention is to provide a compound which improves the balance of an $S1P_5$ receptor agonist activity against an $S1P_1$ receptor agonist activity.

Solutions to Problems

The present inventors conducted intensive studies for achieving the above object, and as a result, they found that the object can be achieved by a compound represented by the following general formula (V) or a pharmaceutically acceptable salt thereof.

That is, the present invention provides, for example, embodiments of

[1] a compound represented by general formula (V) or a pharmaceutically acceptable salt thereof:

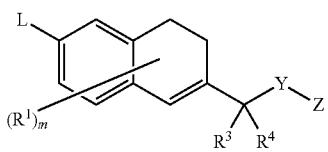

(V)

[wherein L is a branched or linear chain group composed of atoms selected from a carbon atom, an oxygen atom, a nitrogen atom, and a sulfur atom, in which the number of atoms in the main chain thereof is 3 to 8, and the chain group may contain 1 to 3 heteroatoms selected from an oxygen atom, a nitrogen atom, and a sulfur atom, provided that a carbon atom in L may be substituted with 1 to 13 halogen atoms, Y represents

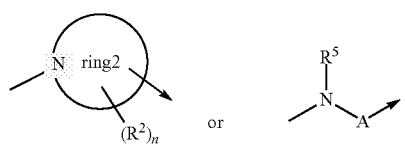

wherein each group is bound to Z through a bond represented by an arrow,

A represents a C3-7 cycloalkylene group which may be substituted or a C1-4 alkylene group which may be substituted, $R^1$ represents a C1-4 alkyl group, a C3-6 cycloalkyl group which may be substituted with a halogen, a C1-4 alkoxy group which may be substituted with a halogen, a C1-4 haloalkyl group, a halogen atom, or a hydroxy group, $R^2$ represents a C1-4 alkyl group, a C1-4 alkoxy group which may be substituted with a halogen, a C1-4 haloalkyl group, a halogen atom, or a hydroxy group, $R^3$, $R^4$, and $R^5$ each independently represent a hydrogen atom, a C1-4 alkyl group, a C3-6 cycloalkyl group which may be substituted with a halogen, or a C1-4 haloalkyl group, Z represents (1) a carboxyl group which may be substituted with one C1-8 alkyl group, (2) a hydroxy group which may be substituted with one C1-8 alkyl group, (3) a hydroxamic acid group which may be substituted with one to two C1-8 alkyl groups, (4) a sulfonic acid group which may be substituted with one C1-8 alkyl group, (5) a boronic acid group which may be substituted with one to two C1-8 alkyl groups, (6) a carbamoyl group which may be substituted with (i) one to two C1-8 alkyl groups or (ii) one to two sulfonyl groups which may be substituted with a C1-4 alkyl group, (7) a sulfamoyl group which may be substituted with (i) one to two C1-8 alkyl groups or (ii) one to two C2-8 acyl groups, (8) a sulfoximine group which may be substituted with one to two C1-8 alkyl groups, or (9) a tetrazolyl group, ring 2 represents a 3- to 7-membered nitrogen-containing heterocycle, m represents an integer of 0 to 6, n represents an integer of 0 to 5, when m is 2 or more, a plurality of $R^1$s may be the same or different, and when n is 2 or more, a plurality of les may be the same or different, provided that each hydrogen atom may be a deuterium atom or a tritium atom],

[2] a pharmaceutical composition comprising the compound represented by the general formula (V) or a pharmaceutically acceptable salt thereof according to the above [1],

[3] a method for preventing and/or treating an $S1P_5$-mediated disease, characterized by administering an effective amount of the compound represented by the general formula (V) or a pharmaceutically acceptable salt thereof according to the above [1] to a mammal,

[4] the compound represented by the general formula (V) or a pharmaceutically acceptable salt thereof according to the above [1] for use in preventing and/or treating an $S1P_5$-mediated disease, and

[5] use of the compound represented by the general formula (V) or a pharmaceutically acceptable salt thereof according to the above [1] for manufacturing a prophylactic and/or therapeutic agent for an $S1P_5$-mediated disease, and the like.

Advantageous Effects of Invention

The compound of the present invention has a highly selective $S1P_5$ receptor agonist activity than $S1P_1$ receptor agonist activity, and therefore, the compound of the present invention is useful for treating an $S1P_5$-mediated disease, for example, neurodegenerative diseases, autoimmune diseases, infections and cancers.

DESCRIPTION OF EMBODIMENTS

Hereinafter, the present invention will be described in detail with reference to specific embodiments. However, the present invention is not limited to the following embodiments, and can be carried out in an arbitrary form without departing from the gist of the invention.

Definitions

In the present invention, the phrase "to improve the balance of an S1P$_5$ receptor agonist activity against an S1P$_1$ receptor agonist activity" means "to increase the selectivity of an S1P$_5$ receptor agonist activity against an S1P$_1$ receptor agonist activity".

In the present invention, a halogen atom means fluorine, chlorine, bromine or iodine.

In the present invention, a C1-8 alkyl group includes a linear or branched C1-8 alkyl group. Examples of the C1-8 alkyl group include methyl, ethyl, propyl, butyl, pentyl, hexyl, heptyl, octyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 2-methylhexyl, 3-methylhexyl, 4-methylhexyl, 5-methylhexyl, 3-ethylpentyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 1-propylpentyl, 2-propylpentyl, 1,5-dimethylhexyl, 1-ethyl-4-methylpentyl, 1-propyl-3-methylbutyl, 1,1-dimethylhexyl, 1-ethyl-1-methyl pentyl and 1,1-diethylbutyl groups.

In the present invention, a C1-6 alkyl group includes a linear or branched C1-6 alkyl group. Examples of the C1-6 alkyl group include methyl, ethyl, propyl, butyl, pentyl, hexyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, and 2,3-dimethylbutyl groups.

In the present invention, a C1-5 alkyl group includes a linear or branched C1-5 alkyl group. Examples of the C1-5 alkyl group include methyl, ethyl, propyl, butyl, pentyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, and 2,2-dimethylpropyl groups.

In the present invention, a C1-4 alkyl group includes a linear or branched C1-4 alkyl group. Examples of the C1-4 alkyl group include methyl, ethyl, propyl, butyl, isopropyl, isobutyl, sec-butyl and tert-butyl groups.

In the present invention, a C2-7 alkyl group includes a linear or branched C2-7 alkyl group. Examples of the C2-7 alkyl group include ethyl, propyl, butyl, pentyl, hexyl, heptyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 2-methylhexyl, 3-methylhexyl, 4-methylhexyl, 5-methylhexyl, and 3-ethylpentyl groups.

In the present invention, a C2-5 alkyl group includes a linear or branched C2-5 alkyl group. Examples of the C2-5 alkyl group include ethyl, propyl, butyl, pentyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, and 2,2-dimethylpropyl groups.

In the present invention, a C3-8 alkyl group includes a linear or branched C3-8 alkyl group. Examples of the C3-8 alkyl group include propyl, butyl, pentyl, hexyl, heptyl, octyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methyl propyl, 1-ethyl-2-methyl propyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-m ethylbutyl, 1-ethyl-3-m ethylbutyl, 1,1-dimethylpentyl, 1,1,3-trimethylbutyl, 1,1-diethylpropyl, 2-methylhexyl, 3-methylhexyl, 4-methylhexyl, 5-methylhexyl, 3-ethylpentyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 1-propylpentyl, 2-propylpentyl, 1,5-dimethylhexyl, 1-ethyl-4-methylpentyl, 1-propyl-3-methylbutyl, 1,1-dimethylhexyl, 1-ethyl-1-methylpentyl and 1,1-diethylbutyl groups.

In the present invention, a C3-6 alkyl group includes a linear or branched C3-6 alkyl group. Examples of the C3-6 alkyl group include propyl, butyl, pentyl, hexyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methyl propyl, 1,1-dimethylbutyl, 1,2-dimethylbutyl, 1,3-dimethylbutyl, 2-methylpentyl, 3-methylpentyl, 4-methylpentyl, and 2,3-dimethylbutyl groups.

In the present invention, a C4-7 alkyl group includes a linear or branched C4-7 alkyl group. Examples of the C4-7 alkyl group include butyl, pentyl, hexyl, heptyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 2-methylhexyl, 3-methylhexyl, 4-methylhexyl, 5-methylhexyl, and 3-ethylpentyl groups.

In the present invention, a C2-7 alkenyl group includes a linear or branched C2-7 alkenyl group. Examples of the C2-7 alkenyl group include ethenyl, propenyl, butenyl, butadienyl, pentenyl, pentadienyl, hexenyl, hexadienyl, heptenyl, and heptadienyl groups, and isomers thereof.

In the present invention, a C2-6 alkenyl group includes a linear or branched C2-6 alkenyl group. Examples of the C2-6 alkenyl group include ethenyl, propenyl, butenyl, butadienyl, pentenyl, pentadienyl, hexenyl, and hexadienyl groups, and isomers thereof.

In the present invention, a C2-5 alkenyl group includes a linear or branched C2-5 alkenyl group. Examples of the C2-5 alkenyl group include ethenyl, propenyl, butenyl, butadienyl, pentenyl, and pentadienyl groups, and isomers thereof.

In the present invention, a C2-4 alkenyl group includes a linear or branched C2-4 alkenyl group. Examples of the C2-4 alkenyl group include ethenyl, propenyl, butenyl, and butadienyl groups, and isomers thereof.

In the present invention, a C3-8 alkenyl group includes a linear or branched C3-8 alkenyl group. Examples of the C3-8 alkenyl group include propenyl, butenyl, butadienyl, pentenyl, pentadienyl, hexenyl, hexadienyl, heptenyl, heptadienyl, octenyl, and octadienyl groups, and isomers thereof.

In the present invention, a C3-6 alkenyl group includes a linear or branched C3-6 alkenyl group. Examples of the C3-6 alkenyl group include propenyl, butenyl, butadienyl, pentenyl, pentadienyl, hexenyl, and hexadienyl groups, and isomers thereof.

In the present invention, a C4-7 alkenyl group includes a linear or branched C4-7 alkenyl group. Examples of the C4-7 alkenyl group include butenyl, butadienyl, pentenyl, pentadienyl, hexenyl, hexadienyl, heptenyl, and heptadienyl groups, and isomers thereof.

In the present invention, a C2-7 alkynyl group includes a linear or branched C2-7 alkynyl group. Examples of the C2-7 alkynyl group include ethynyl, propynyl, butynyl, butadiynyl, pentynyl, pentadiynyl, hexynyl, hexadiynyl, heptynyl, and heptadiynyl groups, and isomers thereof.

In the present invention, a C2-6 alkynyl group includes a linear or branched C2-6 alkynyl group. Examples of the C2-6 alkynyl group include ethynyl, propynyl, butynyl, butadiynyl, pentynyl, pentadiynyl, hexynyl, and hexadiynyl groups, and isomers thereof.

In the present invention, a C2-5 alkynyl group includes a linear or branched C2-5 alkynyl group. Examples of the C2-5 alkynyl group include ethynyl, propynyl, butynyl, butadiynyl, pentynyl, and pentadiynyl groups, and isomers thereof.

In the present invention, a C2-4 alkynyl group includes a linear or branched C2-4 alkynyl group. Examples of the C2-4 alkynyl group include ethynyl, propynyl, butynyl, and butadiynyl groups, and isomers thereof.

In the present invention, a C3-8 alkynyl group includes a linear or branched C3-8 alkynyl group. Examples of the C3-8 alkynyl group include propynyl, butynyl, butadiynyl, pentynyl, pentadiynyl, hexynyl, hexadiynyl, heptynyl, heptadiynyl, octynyl, and octadiynyl groups, and isomers thereof.

In the present invention, a C3-6 alkynyl group includes a linear or branched C3-6 alkynyl group. Examples of the C3-6 alkynyl group include propynyl, butynyl, butadiynyl, pentynyl, pentadiynyl, hexynyl, and hexadiynyl groups, and isomers thereof.

In the present invention, a C4-7 alkynyl group includes a linear or branched C4-7 alkynyl group. Examples of the C4-7 alkynyl group include butynyl, butadiynyl, pentynyl, pentadiynyl, hexynyl, hexadiynyl, heptynyl, and heptadiynyl groups, and isomers thereof.

In the present invention, a C1-5 alkylene group includes linear or branched C1-5 alkylene. Examples of the C1-5 alkylene group include methylene, ethylene, propylene, butylene, and pentylene groups, and isomers thereof.

In the present invention, a C1-4 alkylene group includes linear or branched C1-4 alkylene. Examples of the C1-4 alkylene group include methylene, ethylene, propylene, and butylene groups, and isomers thereof.

In the present invention, a C1-3 alkylene group includes linear or branched C1-3 alkylene. Examples of the C1-3 alkylene group include methylene, ethylene, and propylene groups, and isomers thereof.

In the present invention, a C2-4 alkylene group includes linear or branched C2-4 alkylene. Examples of the C2-4 alkylene group include ethylene, propylene, and butylene groups, and isomers thereof.

In the present invention, a C2-3 alkylene group includes linear or branched C2-3 alkylene. Examples of the C2-3 alkylene group include ethylene and propylene groups, and isomers thereof.

In the present invention, a C3-6 cycloalkyl group includes, for example, cyclopropyl, cyclobutyl, cyclopentyl, and cyclohexyl groups.

In the present invention, a C3-7 cycloalkylene group includes, for example, cyclopropylene, cyclobutylene, cyclopentylene, cyclohexylene, and cycloheptylene groups.

In the present invention, a C1-4 alkoxy group includes, for example, methoxy, ethoxy, propoxy, isopropoxy, butoxy, isobutoxy, sec-butoxy, and tert-butoxy groups.

In the present invention, a C1-4 haloalkyl group includes, for example, a fluoromethyl group, a chloromethyl group, a bromomethyl group, a iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group or a 4-bromobutyl group.

In the present invention, a C2-8 acyl group includes, for example, ethanoyl, propanoyl, butanoyl, pentanoyl, hexanoyl, heptanoyl, and octanoyl groups, and isomers thereof.

In the present invention, a 3- to 7-membered nitrogen-containing heterocycle means a heterocycle always containing one or more nitrogen atoms among unsaturated or saturated 3- to 7-membered monocyclic heterocycles containing 1 to 5 heteroatoms selected from an oxygen atom, a nitrogen atom, and a sulfur atom. Examples of the 3- to 7-membered nitrogen-containing heterocycle include aziridine, pyrrole, imidazole, triazole, tetrazole, pyrazole, azepine, diazepine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), dihydrofurazan, tetrahydrofurazan, dihydrooxadiazole, tetrahydrooxadiazole (oxadiazolidine), tetrahydrooxazine, dihydrooxadiazine, tetrahydrooxadiazine, perhydrooxazepine, tetrahydrooxadiazepine, perhydrooxadiazepine, dihydrothiadiazole, tetrahydrothiadiazole (thiadiazolidine), tetrahydrothiazine, dihydrothiadiazine, tetrahydrothiadiazine, perhydrothiazepine, tetrahydrothiadiazepine, perhydrothiadiazepine, morpholine, thiomorpholine, azabicyclo[2.2.1]heptane, azabicyclo[3.1.1]heptane, and azabicyclo[3.2.1]octane.

In the present invention, a 4- to 7-membered nitrogen-containing heterocycle means a heterocycle always containing one or more nitrogen atoms among unsaturated or saturated 4- to 7-membered monocyclic heterocycles containing 1 to 5 heteroatoms selected from an oxygen atom, a nitrogen atom, and a sulfur atom. Examples of the 4- to 7-membered nitrogen-containing heterocycle include pyrrole, imidazole, triazole, tetrazole, pyrazole, azepine, diazepine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), dihydrofurazan, tetrahydrofurazan, dihydrooxadiazole, tetrahydrooxadiazole (oxadiazolidine), tetrahydrooxazine, dihydrooxadiazine, tetrahydrooxadiazine, perhydrooxazepine, tetrahydrooxadiazepine, perhydrooxadiazepine, dihydrothiadiazole, tetrahydrothiadiazole (thiadiazolidine), tetrahydrothiazine, dihydrothiadiazine, tetrahydrothiadiazine, perhydrothiazepine, tetrahydrothiadiazepine, perhydrothiadiazepine, morpholine, thiomorpholine, azabicyclo[2.2.1]heptane, azabicyclo[3.1.1]heptane, and azabicyclo[3.2.1]octane.

In the present invention, a 3- to 7-membered nitrogen-containing saturated heterocycle means a heterocycle always containing one or more nitrogen atoms among partially or wholly saturated 3- to 7-membered monocyclic heterocycles containing 1 to 5 heteroatoms selected from an oxygen atom, a nitrogen atom, and a sulfur atom. Examples of the 3- to 7-membered nitrogen-containing saturated heterocycle include aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), tetrahydroisoxazole (isoxazolidine), tetrahydrothiazole (thiazolidine), tetrahydroisothiazole (isothiazolidine), dihydrofurazan, tetrahydrofurazan, dihydrooxadiazole, tetrahydrooxadiazole (oxadiazolidine), tetrahydrooxazine, dihydrooxadiazine, tetrahydrooxadiazine, perhydrooxazepine, tetrahydrooxadiazepine, perhydrooxadiazepine, dihydrothiadiazole, tetrahydrothiadiazole (thiadiazolidine), tetrahydrothiazine, dihydrothiadiazine, tetrahydrothiadiazine, perhydrothiazepine, tetrahydrothiadiazepine, perhydrothiadiazepine, morpholine, thiomorpholine, azabicyclo[2.2.1]heptane, azabicyclo[3.1.1]heptane, and azabicyclo[3.2.1]octane.

In the present invention, a 4- to 7-membered nitrogen-containing saturated heterocycle means a heterocycle always containing one or more nitrogen atoms among partially or wholly saturated 4- to 7-membered monocyclic heterocycles containing 1 to 5 heteroatoms selected from an oxygen atom, a nitrogen atom, and a sulfur atom. Examples of the 4- to 7-membered nitrogen-containing saturated heterocycle include azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), tetrahydroisoxazole (isoxazolidine), tetrahydrothiazole (thiazolidine), tetrahydroisothiazole (isothiazolidine), dihydrofurazan, tetrahydrofurazan, dihydrooxadiazole, tetrahydrooxadiazole (oxadiazolidine), tetrahydrooxazine, dihydrooxadiazine, tetrahydrooxadiazine, perhydrooxazepine, tetrahydrooxadiazepine, perhydrooxadiazepine, dihydrothiadiazole, tetrahydrothiadiazole (thiadiazolidine), tetrahydrothiazine, dihydrothiadiazine, tetrahydrothiadiazine, perhydrothiazepine, tetrahydrothiadiazepine, perhydrothiadiazepine, morpholine, thiomorpholine, azabicyclo[2.2.1]heptane, azabicyclo[3.1.1]heptane, and azabicyclo[3.2.1]octane.

In the present invention, a chain group means a linear or branched chain group composed of atoms selected from a carbon atom, an oxygen atom, a nitrogen atom, and a sulfur atom.

In the present invention, a main chain means a portion, which contains atoms bound to a base skeleton (dihydronaphthalene skeleton) among the atoms constituting the chain group, and is bound in the longest linear chain.

In the present invention, the number of atoms in the main chain means the total number of carbon atoms, oxygen atoms, nitrogen atoms, and sulfur atoms contained in the main chain. For example, when L is a group represented by the following figure, the number of atoms in the main chain is 5.

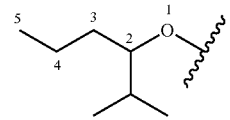 [SMILES: *OC(CCC)C(C)C]

In the present invention, L also represents a linear or branched chain hydrocarbon group having 3 to 8 carbon atoms in the main chain, or a heteroatom-containing chain hydrocarbon group containing 1 to 3 heteroatoms instead of 1 to 3 carbon atoms in the chain hydrocarbon group, wherein the heteroatoms independently selected from an oxygen atom, a nitrogen atom, and a sulfur atom, respectively.

In the present invention, the linear or branched chain hydrocarbon group having 3 to 8 carbon atoms in the main chain means, for example, a C3-8 alkyl group, a C3-8 alkenyl group, or a C3-8 alkynyl group.

[Compound of the Present Invention]

In the present invention, $R^1$ is preferably a C1-4 alkyl group, a C3-6 cycloalkyl group which may be substituted with a halogen, a C1-4 haloalkyl group, or a halogen atom, more preferably a C1-4 alkyl group, a C3-6 cycloalkyl group, or a halogen atom, and particularly preferably a methyl group, a cyclopropyl group, or fluorine.

In the present invention, $R^2$ is preferably a C1-4 alkyl group, a halogen atom, a C1-4 alkoxy group which may be substituted with a halogen, or a hydroxy group, more preferably a C1-4 alkyl group, a halogen atom, a C1-4 alkoxy group, or a hydroxy group, and particularly preferably fluorine, a methyl group, a methoxy group, or a hydroxy group.

In the present invention, R³ is preferably a hydrogen atom or a C1-4 alkyl group, more preferably a hydrogen atom or a methyl group, and particularly preferably a hydrogen atom.

In the present invention, R⁴ is preferably a hydrogen atom or a C1-4 alkyl group, more preferably a hydrogen atom or a methyl group, and particularly preferably a hydrogen atom.

In the present invention, R⁵ is preferably a hydrogen atom or a C1-4 alkyl group, and more preferably a hydrogen atom or a methyl group.

In the present invention, the halogen atom is preferably fluorine.

In the present invention, L is preferably a branched or linear chain group composed of atoms selected from a carbon atom, an oxygen atom, a nitrogen atom, and a sulfur atom, in which the number of atoms in the main chain thereof is 4 to 7, and the chain group is a chain group that may contain 1 to 3 heteroatoms selected from an oxygen atom, a nitrogen atom, and a sulfur atom (provided that a carbon atom in L may be substituted with 1 to 13 halogen atoms), more preferably a chain group that is (1) —O—(C3-6 alkyl), (2) —O—(C3-6 alkenyl), (3) —O—(C3-6 alkynyl), (4) —O—(C1-4 alkylene)-OCH₃, (5) —O—(C1-3 alkylene)-OCH₂CH₃, (6) —CH₂O—(C2-5 alkyl), (7) —CH₂O—(C2-5 alkenyl), (8) —CH₂O—(C2-5 alkynyl), (9) —CH₂CH₂O—(C1-4 alkyl), (10) —CH₂CH₂O—(C2-4 alkenyl), (11) —CH₂CH₂O—(C2-4 alkynyl), (12) —S—(C3-6 alkyl), (13) —S—(C3-6 alkenyl), (14) —S—(C3-6 alkynyl), (15) —NR⁶—(C3-6 alkyl), (16) —NR⁶—(C3-6 alkenyl), (17) —NR⁶—(C3-6 alkynyl), (18) a C4-7 alkyl group, (19) a C4-7 alkenyl group, or (20) a C4-7 alkynyl group (wherein R⁶ represents a hydrogen atom or a C1-4 alkyl group, and a carbon atom in each group may be substituted with 1 to 13 halogen atoms), and particularly preferably

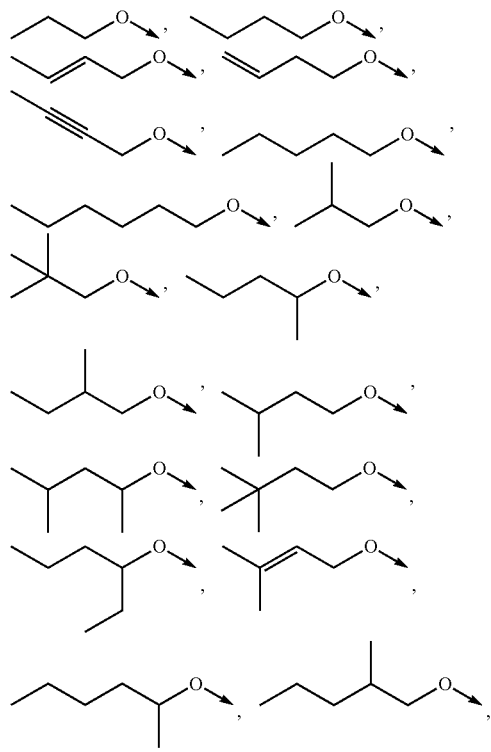

-continued

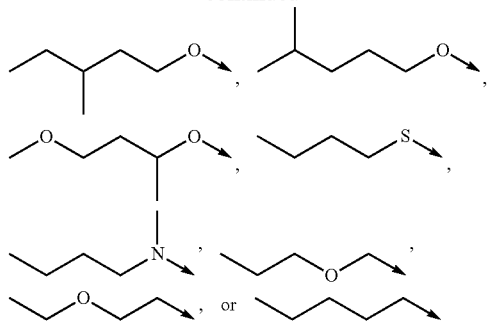

wherein a carbon atom in each group may be substituted with 1 to 13 halogen atoms, and each group is bound to a dihydronaphthalene ring through a bond represented by an arrow).

In the present invention, L is preferably (1) —O—(C2-7 alkyl), (2) —O—(C2-7 alkenyl), (3) —O—(C2-7 alkynyl), (4) —O—(C1-5 alkylene)-OCH₃, (5) —O—(C1-4 alkylene)-OCH₂CH₃, (6) —CH₂O—(C1-6 alkyl), (7) —CH₂O—(C2-6 alkenyl), (8) —CH₂O—(C2-6 alkynyl), (9) —CH₂CH₂O—(C1-5 alkyl), (10) —CH₂CH₂O—(C2-5 alkenyl), (11) —CH₂CH₂O—(C2-5 alkynyl), (12) —S—(C2-7 alkyl), (13) —S—(C2-7 alkenyl), (14) —S—(C2-7 alkynyl), (15) —NR⁶—(C2-7 alkyl), (16) —NR⁶—(C2-7 alkenyl), (17) —NR⁶—(C2-7 alkynyl), (18) a C3-8 alkyl group, (19) a C3-8 alkenyl group, or (20) a C3-8 alkynyl group (wherein R⁶ represents a hydrogen atom or a C1-4 alkyl group, and a carbon atom in each group may be substituted with 1 to 13 halogen atoms).

In the present invention, L is also preferably

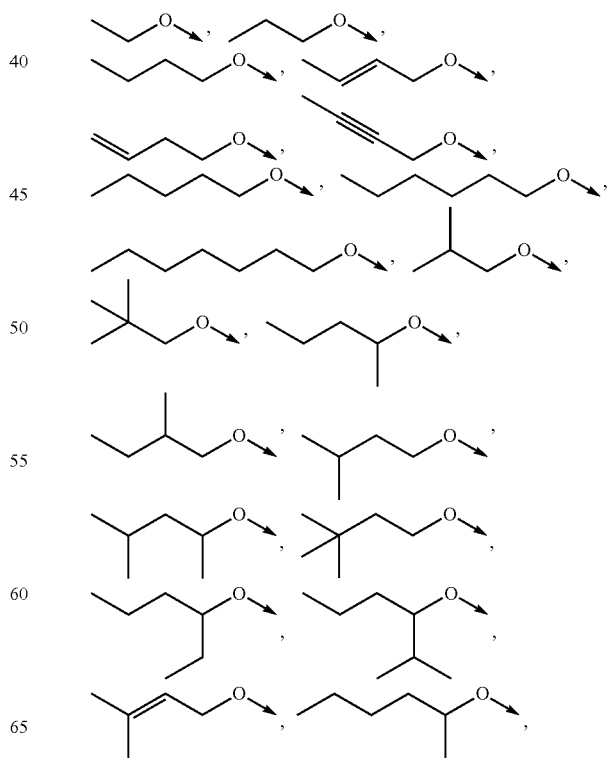

-continued

[Chemical structures showing various branched and linear chain groups with O, S, and N heteroatoms attached to dihydronaphthalene ring]

(wherein a carbon atom in each group may be substituted with 1 to 13 halogen atoms, and each group is bound to a dihydronaphthalene ring through a bond represented by an arrow).

In the present invention, Z is preferably a carboxyl group which may be substituted with a C1-8 alkyl group or a tetrazolyl group, more preferably a carboxyl group or a tetrazolyl group, and particularly preferably a carboxyl group.

In the present invention, ring 2 is preferably a 3- to 7-membered nitrogen-containing saturated heterocycle, more preferably a 4- to 7-membered nitrogen-containing saturated heterocycle, particularly preferably azetidine, pyrrolidine, piperidine, or perhydroazepine, and further more preferably azetidine or pyrrolidine.

In the present invention, ring 1 is preferably a 4- to 7-membered nitrogen-containing saturated heterocycle, more preferably azetidine, pyrrolidine, piperidine, or perhydroazepine, and particularly preferably azetidine or pyrrolidine.

In the present invention, when $R^1$ is bound to asymmetric carbon on dihydronaphthalene, the following configuration is preferred as the configuration of $R^1$. $R^1$ capable of taking the configuration is more preferably a C1-4 alkyl group, and particularly preferably a methyl group.

[Chemical structure showing dihydronaphthalene with R¹ in specific stereochemical configuration]

In the present invention, when an oxygen atom is present at an end of the chain group represented by L, the oxygen atom may be either =O or —OH.

In the present invention, Y is preferably

[Chemical structure showing N-containing ring2 with (R²)ₙ]

In the present invention, A is preferably (1) a C3-7 cycloalkylene group which may be substituted with C1-4 alkyl, C1-4 alkoxy, a halogen, or a hydroxy group, or (2) a C1-4 alkylene group which may be substituted with C1-4 alkyl, C1-4 alkoxy, a halogen, or a hydroxy group, more preferably a C3-7 cycloalkylene group or a C1-4 alkylene group, and particularly preferably a cyclobutane or ethylene group.

In the present invention, m is preferably an integer of 0 to 3, and more preferably an integer of 0 to 2.

In the present invention, n is preferably an integer of 0 to 2, and more preferably an integer of 0 to 1.

In the present invention, the compound is preferably a compound represented by general formula (V-1):

(V-1)

[Chemical structure showing dihydronaphthalene with L, (R¹)ₘ, N-ring2, Z, R³, R⁴, (R²)ₙ substituents]

[wherein all the symbols have the same meanings as described above, provided that each hydrogen atom may be a deuterium atom or a tritium atom].

In the present invention, the compound is preferably a compound represented by general formula (V-2):

(V-2)

[Chemical structure showing dihydronaphthalene with L¹, (R¹)ₘ₋₁, CH₃, N-ring2-1, Z, R³, R⁴, (R²)ₙ₋₁ substituents]

[wherein $L^1$ is a branched or linear chain group composed of atoms selected from a carbon atom, an oxygen atom, a nitrogen atom, and a sulfur atom, in which the number of atoms in the main chain thereof is 4 to 7, and the chain group may contain 1 to 3 heteroatoms selected from an oxygen atom, a nitrogen atom, and a sulfur atom, provided that a carbon atom in $L^1$ may be substituted with 1 to 13 halogen atoms, ring 2-1 represents a 3- to 7-membered nitrogen-containing saturated heterocycle, m-1 represents an integer of 0 to 2, n-1 represents an integer of 0 to 2, when m-1 is 2, a plurality of Les may be the same or different, when n-1 is 2, a plurality of Les may be the same or different, and the other symbols have the same meanings as described above, provided that each hydrogen atom may be a deuterium atom or a tritium atom].

In the present invention, the compound is preferably a compound represented by general formula (I):

(I)

[chemical structure of formula (I)]

[wherein ring 1 represents a 4- to 7-membered nitrogen-containing heterocycle, and the other symbols have the same meanings as described above, provided that each hydrogen atom may be a deuterium atom or a tritium atom].

In the present invention, the compound is more preferably a compound represented by general formula (I-1):

(I-1)

[chemical structure of formula (I-1)]

[wherein ring 1-1 represents a 4- to 7-membered nitrogen-containing saturated heterocycle, and the other symbols have the same meanings as described above, provided that each hydrogen atom may be a deuterium atom or a tritium atom].

In the present invention, the compound is also preferably a compound represented by general formula (I-1-1):

(I-1-1)

[chemical structure of formula (I-1-1)]

[wherein all the symbols have the same meanings as described above, provided that each hydrogen atom may be a deuterium atom or a tritium atom].

In the present invention, in the general formula (I-1), the general formula (V-2), or the general formula (I-1-1), $L^1$ is preferably a chain group that is (1) —O—(C3-6 alkyl), (2) —O—(C3-6 alkenyl), (3) —O—(C3-6 alkynyl), (4) —O—(C1-4 alkylene)-OCH$_3$, (5) —O—(C1-3 alkylene)-OCH$_2$CH$_3$, (6) —CH$_2$O—(C2-5 alkyl), (7) —CH$_2$O—(C2-5 alkenyl), (8) —CH$_2$O—(C2-5 alkynyl), (9) —CH$_2$CH$_2$O—(C1-4 alkyl), (10) —CH$_2$CH$_2$O—(C2-4 alkenyl), (11) —CH$_2$CH$_2$O—(C2-4 alkynyl), (12) —S—(C3-6 alkyl), (13) —S—(C3-6 alkenyl), (14) —S—(C3-6 alkynyl), (15) —NR$^6$—(C3-6 alkyl), (16) —NR$^6$—(C3-6 alkenyl), (17) —NR$^6$—(C3-6 alkynyl), (18) a C4-7 alkyl group, (19) a C4-7 alkenyl group, or (20) a C4-7 alkynyl group (wherein R$^6$ represents a hydrogen atom or a C1-4 alkyl group, and a carbon atom in each group may be substituted with 1 to 13 halogen atoms), and more preferably

[chemical structures of various chain groups]

(wherein a carbon atom in each group may be substituted with 1 to 13 halogen atoms, and each group is bound to a dihydronaphthalene ring through a bond represented by an arrow).

In the present invention, in the general formula (I-1), the general formula (V-2), or the general formula (I-1-1), ring 1-1 or ring 2-1 is preferably azetidine, pyrrolidine, piperidine, or perhydroazepine, and more preferably azetidine or pyrrolidine.

In the above-mentioned general formulae, it is also preferred to arbitrarily combine preferred groups exemplified above, respectively.

In the present invention, the compound is preferably compounds described in Examples, and more preferably (1) 1-[((3R)-6-butoxy-3-methyl-3,4-dihydronaphthalen-2-yl)methyl]azetidine-3-carboxylic acid, (2) 1-[((3S)-6-butoxy-3-methyl-3,4-dihydronaphthalen-2-yl)methyl]azetidine-3-carboxylic acid, (3) 1-[((3S)-3-methyl-6-pentoxy-3,4-dihydronaphthalen-2-yl)methyl]azetidine-3-carboxylic acid, (4) 1-[[(3S)-3-methyl-6-(4,4,4-trifluorobutoxy)-3,4-dihydronaphthalen-2-yl]methyl]azetidine-3-carboxylic acid, (5) 3-fluoro-1-[[(3S)-3-methyl-6-(3,4,4-trifluorobut-3-enoxy)-3,4-dihydronaphthalen-2-yl]methyl]azetidine-3-carboxylic acid, (6) 1-[[(3S)-3-methyl-6-(1,1,2,2,3,3,4,4,4-nonadeuteriobutoxy)-3,4-dihydronaphthalen-2-yl]methyl]azetidine-3-carboxylic acid, (7) (3R)-1-[[(3S)-3-methyl-6-(4,4,4-trifluorobutoxy)-3,4-dihydronaphthalen-2-yl]methyl]pyrrolidine-3-carboxylic acid, (8) 1-[[(3S)-3-methyl-6-((R)-3,3,3-trifluoro-2-methylpropoxy)-3,4-dihydronaphthalen-2-yl]methyl]azetidine-3-carboxylic acid, (9) 1-[[(3S)-3-methyl-6-((S)-3,3,3-trifluoro-2-methylpropoxy)-3,4-dihydronaphthalen-2-yl]methyl]azetidine-3-carboxylic acid, (10) 3-fluoro-1-[[(3S)-3-methyl-6-[(E)-4,4,4-trifluorobut-2-enoxy]-3,4-dihydronaphthalen-2-yl]methyl]azetidine-3-carboxylic acid, (11) 3-fluoro-1-{[(3S)-3-methyl-6-(3,3,3-trifluoropropoxy)-3,4-dihydro-2-naphthalenyl]methyl}-3-azetidinecarboxylic acid, (12) cis-3-({1-[(3S)-3-methyl-6-(4,4,4-trifluorobutoxy)-3,4-dihydro-2-naphthalenyl]ethyl}amino)cyclobutanecarboxylic acid, or (13) 1-{[(3S)-3-methyl-6-(propoxymethyl)-3,4-dihydro-2-naphthalenyl]methyl}-3-azetidinecarboxylic acid.

In the present invention, the compound is preferably a compound whose clearance as measured by the method described in Biological Experimental Example 2 is 10 mL/min/kg or less, and more preferably a compound whose clearance is 5 mL/min/kg or less.

In the present invention, the compound is preferably a compound whose effective dose as measured by the method described in Biological Experimental Example 4 is 100 mg/kg or less, more preferably a compound whose effective dose is 10 mg/kg or less, and particularly preferably a compound whose effective dose is 1 mg/kg or less.

Unless otherwise specifically indicated, all isomers are included in the present invention. For example, an alkyl group includes linear and branched ones. In addition, all of geometric isomers due to double bond(s), ring(s) and fused ring(s) ((E)-, (Z)-, cis- and trans-forms), optical isomers due to the presence of asymmetric carbon atom(s) and the like (R-, S-, α- and, β-configurations, enantiomer(s) and diastereomer(s)), optically active substances having optical rotation (D-, L-, d- and l-forms), polar substances by chromatographic separation (more polar and less polar substances), compounds in equilibrium, rotational isomers, a mixture thereof in any proportion and a racemic mixture are included in the present invention. In addition, tautomers are all included in the present invention.

Further, optical isomers in the present invention may include, not only 100%—pure isomers, but also isomers contain less than 50%—other optical isomers.

In the present invention, unless otherwise specified, the symbol: 
represents that a substituent binds to the back side on the paper surface (in other words, α-configuration), the symbol: 
represents that a substituent binds to the front side on the paper surface (in other words, β-configuration), and the symbol: 
represents α-configuration, β-configuration or a mixture thereof at an appropriate ratio, as would be apparent to those skilled in the art.

In the present invention, all references with respect to the compound of the present invention include the compound represented by the general formula (V), a salt thereof, a solvate thereof, an N-oxide thereof, or a cocrystal thereof, or a solvate of a salt of the compound represented by the general formula (V) or a cocrystal thereof.

The compound represented by the general formula (V) is converted into a corresponding salt by a known method. The salt is preferably a water-soluble salt. In addition, the salt is preferably a pharmaceutically acceptable salt. Examples of such a salt include salts of alkali metals (such as lithium, potassium, and sodium), salts of alkaline earth metals (such as calcium and magnesium), salts of other metals (such as silver and zinc), ammonium salts, salts of pharmaceutically acceptable organic amines (such as tetramethylammonium, choline, triethylamine, methylamine, dimethylamine, ethylamine, diethylamine, cyclopentylamine, benzylamine, phenethylamine, tert-butylamine, ethylenediamine, piperidine, piperazine, monoethanolamine, diethanolamine, tris(hydroxymethyl)aminomethane, N-benzyl-2-phenethylamine, deanol, 2-(diethylamino)ethanol, 1-(2-hydroxyethyl)pyrrolidine, lysine, arginine, and N-methyl-D-glucamine), acid adduct salts (such as inorganic acid salts (such as a hydrochloride, a hydrobromide, a hydroiodide, a sulfate, a phosphate, and a nitrate) and organic acid salts (such as an acetate, a trifluoroacetate, a lactate, a tartrate, an oxalate, a fumarate, a maleate, a benzoate, a hydroxybenzoate, a citrate, a methanesulfonate, an ethanesulfonate, a benzenesulfonate, a toluenesulfonate, an isethionate, a napadisilate, a glucuronate, and a gluconate)), and the like.

The compound represented by the general formula (V) or a pharmaceutically acceptable salt thereof can be also converted into a solvate. The solvate is preferably a low-toxicity and water-soluble solvate. Examples of such a solvate include a solvate of water and a solvate of an alcohol based solvent (such as a solvate of ethanol). In one embodiment, it is a hydrate.

An N-oxide of the compound represented by the general formula (V) represents a compound obtained by oxidation a nitrogen atom in the compound represented by the general formula (V). In addition, the N-oxide of the compound represented by the general formula (V) may be further converted to the above-described alkali (alkaline earth) metal salt, the ammonium salt, the organic amine salt or the acid addition salt.

The compound represented by the general formula (V) or a pharmaceutically acceptable salt thereof can form a cocrystal with an appropriate cocrystal forming agent. The cocrystal is preferably a pharmaceutically acceptable cocrystal formed with a pharmaceutically acceptable cocrystal forming agent. The cocrystal is typically defined as a crystal formed by two or more different types of intermolecular interactions. Further, the cocrystal may be a complex of a neutral molecule and a salt. The cocrystal can be prepared by a known method, for example, by melt crystallization, by recrystallization from a solvent, or by physical grinding of the components together. Examples of a suitable cocrystal forming agent include organic acids (such as malic acid, succinic acid, adipic acid, gluconic acid, tartaric acid, benzoic acid, 4-hydroxybenzoic acid, 3-hydroxybenzoic acid, nicotinic acid, and isonicotinic acid), organic amines (such as imidazole, diethanolamine, triethanolamine, tris(hydroxymethyl)aminomethane, N-benzyl-phenethylamine, deanol, 2-(diethylamino)ethanol, 1-(2-hydroxyethyl)pyrrolidine, 4-(2-hydroxyethyl)morpholine, N-methyl-D-glucamine, glycine, histidine, and proline) and other organic compounds (such as caffeine and saccharin), and the like. Suitable cocrystal forming agents include those described in WO 2006/007448.

In addition, the compound represented by the general formula (V) can be administered as a prodrug. For example, a prodrug of the compound represented by the general formula (V) refers to a compound which is converted to the compound represented by the general formula (V) by a reaction with an enzyme, gastric acid and the like in vivo. Examples of the prodrug of the compound represented by the general formula (V) include the followings: when the compound represented by the general formula (V) has a hydroxy group, a compound obtained by making the hydroxy group in the compound represented by the general formula (V) is acylated, alkylated, phosphorylated or borated (for example, a compound obtained by making the hydroxy group in the compound of the present invention is acetylated, palmitoylated, propanoylated, pivaloylated, succinylated, fumarylated, alanylated, dimethylaminomethylcarbonylated or the like); a compound obtained by making a carboxyl group in the compound represented by the general formula (V) is esterified or amidated (for example, a compound obtained by making a carboxyl group in the compound represented by the general formula (V) is an ethyl ester, an isopropyl ester, a phenyl ester, a carboxymethyl ester, a dimethylaminomethyl ester, a pivaloyloxymethyl ester, an ethoxycarbonyloxyethyl ester, a phthalidyl ester, a (5-methyl-2-oxo-1,3-dioxolen-4-yl)methyl ester, a cyclohexyloxycarbonylethyl ester, a methylamide or the like); and the like. These compounds can be prepared by a known method. In addition, the prodrug of the compound represented by the general formula (V) may be either a hydrate or a non-hydrate. Further, the prodrug of the compound represented by the general formula (V) may be a compound which is converted to the compound represented by the general formula (V) under a physiological condition as described in "*Iyakuhin no kaihatsu*", Vol. 7, "*Bunshi sekkei*", pages 163-198, Hirokawa-Shoten Ltd., published 1990.

Furthermore, the compound represented by the general formula (V) may also be labeled by an isotope (for example, $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$ and the like) and the like.

[Processes for the preparation of the compound of the present invention]

The compound of the present invention can be prepared by a known method. For example, the compound of the present invention can be prepared by appropriately improving a method described in Comprehensive Organic Transformations: A Guide to Functional Group Preparations, 3rd Edition (Richard C. Larock, John Wiley & Sons Inc., 2018) or the methods described in Examples and the like or combining these methods.

A compound of the general formula (V) in which $R^3$ and $R^4$ are each a hydrogen atom, and one of the atoms constituting L is an oxygen atom, and ring 1 is a 4- to 7-membered nitrogen-containing saturated heterocycle, that is, a compound represented by general formula (I-A):

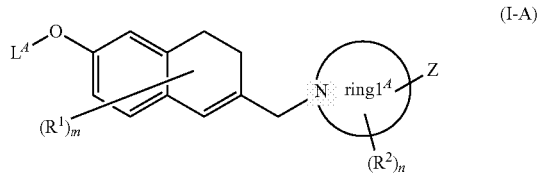

(wherein $L^A$ is a branched or linear chain group composed of atoms selected from a carbon atom, an oxygen atom, a nitrogen atom, and a sulfur atom, in which the number of atoms in the main chain thereof is 2 to 7, and the chain group may contain 1 to 2 heteroatoms selected from an oxygen atom, a nitrogen atom, and a sulfur atom, provided that a carbon atom in $L^A$ may be substituted with 1 to 13 halogen atoms, ring $1^A$ represents a 4- to 7-membered nitrogen-containing saturated heterocycle, and the other symbols have the same meanings as described above) can be produced according to reaction scheme 1 shown below. Note that a compound of the general formula (I-A) in which ring $1^A$ is a 3- to 7-membered nitrogen-containing saturated heterocycle can also be produced in the same manner as the method according to the Reaction Scheme 1.

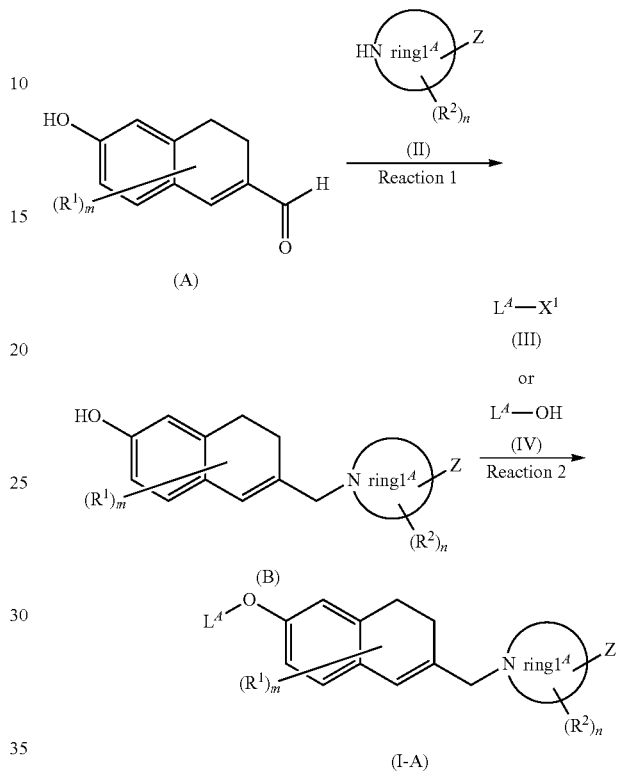

(wherein $X^1$ represents a halogen atom, a trifluoromethanesulfonyloxy group (OTf group), a methanesulfonyloxy group (OMs group), or a toluenesulfonyloxy group (OTs), and the other symbols have the same meanings as described above.)

In the Reaction Scheme 1, reaction 1 can be carried out by using a compound represented by general formula (A) and a compound represented by general formula (II) and subjecting the compounds to a reductive amination reaction. The reductive amination reaction is known and is carried out, for example, in an organic solvent (such as di chloroethane, dichloromethane, N,N-dimethylformamide, N,N-dimethyl acetamide, N-methylpyrrolidone, acetic acid, tetrahydrofuran, methanol, or a mixture thereof) in the presence of a reducing agent (such as sodium triacetoxyborohydride, sodium cyanoborohydride, or sodium borohydride) at a temperature of 0 to 40° C.

In the Reaction Scheme 1, reaction 2 can be carried out by subjecting a compound represented by general formula (B) and a compound represented by general formula (III) to an etherification reaction or subjecting a compound represented by general formula (B) and a compound represented by general formula (IV) to a Mitsunobu reaction. The etherification reaction is known and is carried out, for example, in an organic solvent (such as N,N-dimethylformamide, dimethyl sulfoxide, chloroform, dichloromethane, diethyl ether, tetrahydrofuran, or methyl t-butyl ether) in the presence of an alkali metal hydroxide (such as sodium hydroxide, potassium hydroxide, or lithium hydroxide), an alkaline earth metal hydroxide (such as barium hydroxide or calcium hydroxide), or a carbonate (such as sodium carbonate or potassium carbonate), or an aqueous solution thereof or a mixture thereof at 0 to 100° C. The Mitsunobu reaction is known and is carried out, for example, in an organic solvent (such as dichloromethane, diethyl ether, tetrahydrofuran, acetonitrile, benzene, or toluene) in the presence of an azo compound (such as diethyl azodicarboxylate (DEAD), diisopropyl azodicarboxylate, 1,1'-(azodicarbonyl)dipiperidine, or 1,1'-azobis(N,N-dimethylformamide)), or a phosphine compound (such as triphenylphosphine, tributylphosphine, trimethylphosphine, or polymer-supported triphenylphosphine) at 0 to 60° C.

A compound of the general formula (V) in which one of the atoms constituting L is a carbon atom, a nitrogen atom, or a sulfur atom, that is, a compound represented by general formula (V-A):

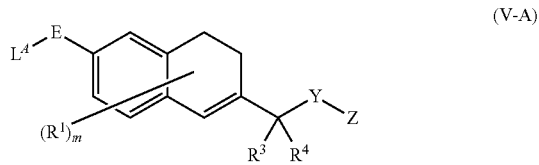

(V-A)

(wherein E represents a carbon atom, a nitrogen atom, or a sulfur atom, and the other symbols have the same meanings as described above) can be produced according to Reaction Scheme 2 shown below.

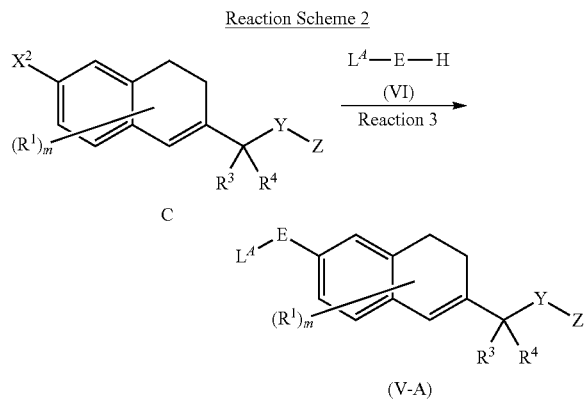

Reaction Scheme 2

(wherein $X^2$ represents a halogen atom or a trifluoromethanesulfonyloxy group (OTf group), and the other symbols have the same meanings as described above.)

In the Reaction Scheme 2, reaction 3 can be carried out by subjecting a compound represented by general formula (C) and a compound represented by general formula (VI) to a transition metal catalyst cross-coupling reaction. The transition metal catalyst cross-coupling reaction is known, and examples of the transition metal catalyst include a palladium catalyst, a copper catalyst, a nickel catalyst, a ruthenium catalyst, an iridium catalyst, a rhodium catalyst, an iron catalyst, a platinum catalyst, a silver catalyst, and a gold catalyst.

Among the transition metal catalyst cross-coupling reactions, a Suzuki coupling reaction is carried out, for example, in an organic solvent (such as benzene, toluene, dimethylformamide, dioxane, tetrahydrofuran, methanol, acetonitrile, dimethoxyethane, or acetone) in the presence of a base (such as sodium ethylate, sodium hydroxide, potassium hydroxide, triethylamine, sodium carbonate, sodium hydrogen carbonate, potassium carbonate, cesium carbonate, thallium carbonate, tripotassium phosphate, cesium fluoride, barium hydroxide, or tetrabutylammonium fluoride), or an aqueous solution thereof or a mixture thereof and a catalyst (such as tetrakis(triphenylphosphine)palladium ($Pd(PPh_3)_4$), bis(triphenylphosphine)palladium dichloride ($PdCl_2(PPh_3)_2$), palladium acetate ($Pd(OAc)_2$), palladium black, 1,1'-bis(diphenylphosphinoferrocene)dichloropalladium ($PdCl_2(dppf)_2$), diallyl palladium dichloride ($PdCl_2(allyl)_2$), phenylbis(triphenylphosphine)palladium iodide (PhPdI($PPh_3)_2$), or tris(dibenzylideneacetone)dipalladium ($Pd_2(dba)_3$)) at room temperature to 120° C.

In Reaction Schemes 1 or 2, when a protecting group is present in each of the compounds represented by general formulae, for example, when Z is protected, a deprotection reaction can be performed, as necessary.

Examples of the protecting group for a carboxyl group include a methyl group, an ethyl group, an allyl group, a t-butyl group, a trichloroethyl group, a benzyl (Bn) group, a phenacyl group, and the like.

Examples of the protecting group of a hydroxy group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group and the like.

The protecting groups are not particularly limited to those described above as long as the protecting groups can be eliminated easily and selectively. For example, the protecting groups described in T. W. Greene, Protective Groups in Organic Synthesis, Fifth Edition, Wiley, New York, 2014 are used.

The deprotection reactions of protecting groups are well known and can be performed by the following methods. Examples of the deprotection reaction include (1) alkaline hydrolysis,
(2) a deprotection reaction under an acidic condition,
(3) a deprotection reaction by hydrogenolysis,
(4) a deprotection reaction of a silyl group,
(5) a deprotection reaction by using a metal,
(6) a deprotection reaction by using a metal complex and the like.

These methods are described specifically as follows.

(1) A deprotection reaction by alkaline hydrolysis is performed, for example, in an organic solvent (such as methanol, tetrahydrofuran and dioxane), by using a hydroxide of an alkali metal (such as sodium hydroxide, potassium hydroxide and lithium hydroxide), a hydroxide of an alkaline earth metal (such as barium hydroxide and calcium hydroxide), a carbonate (such as sodium carbonate and potassium carbonate), an aqueous solution thereof or a mixture thereof at 0 to 40° C.

(2) A deprotection reaction under an acidic condition is performed, for example, in an organic solvent (such as dichloromethane, chloroform, dioxane, ethyl acetate, and anisole), in an organic acid (such as acetic acid, trifluoroacetic acid, methanesulfonic acid and p-tosylic acid), an inorganic acid (such as hydrochloric acid and sulfuric acid) or a mixture thereof (such as hydrobromic acid/acetic acid) at 0 to 100° C.

(3) A deprotection reaction by hydrogenolysis is performed, for example, in a solvent (such as an ether-based solvent (such as tetrahydrofuran, dioxane, dimethoxyethane and diethyl ether), an alcohol-based solvent (such as methanol and ethanol), a benzene-based solvent (such as benzene and toluene), a ketone-based solvent (such as acetone and methyl ethyl ketone), a nitrile-based solvent (such as acetonitrile), an amide-based solvent (such as dimethylformamide), water, ethyl acetate, acetic acid or a mixed solvent of two or more of them), in the presence of a catalyst (such as a palladium-carbon, a palladium black, palladium hydroxide-carbon, platinum oxide and a Raney nickel), under hydrogen atmosphere at a normal pressure or under pressurization or in the presence of ammonium formate, at 0 to 200° C.

(4) A deprotection reaction of a silyl group is performed, for example, in a water-miscible organic solvent (such as tetrahydrofuran and acetonitrile), by using tetrabutylammonium fluoride at 0 to 40° C.

(5) A deprotection reaction by using a metal is performed, for example, in an acidic solvent (such as acetic acid, a buffer solution of pH 4.2 to 7.2 or a mixed solution of such a solution and an organic solvent such as tetrahydrofuran), in the presence of powdery zinc, if necessary, while applying an ultrasonic wave, at 0 to 40° C.

(6) A deprotection reaction by using a metal complex is performed, for example, in an organic solvent (such as dichloromethane, dimethylformamide, tetrahydrofuran, ethyl acetate, acetonitrile, dioxane and ethanol), water or a mixed solvent thereof, in the presence of a trapping reagent (such as tributyltin hydride, triethylsilane, dimedone, morpholine, diethylamine and pyrrolidine), an organic acid (such as acetic acid, formic acid and 2-ethylhexanoic acid) and/or a salt of an organic acid (such as sodium 2-ethylhexanoate and potassium 2-ethylhexanoate), in the presence or absence of a phosphine-based reagent (such as triphenylphosphine), by using a metal complex (such as tetrakis(triphenylphosphine)palladium (0), bis(triphenylphosphine)palladium (II) dichloride, palladium (II) acetate and chlorotris(triphenylphosphine)rhodium (I)), at 0 to 40° C.

In addition to the above-described methods, a deprotection reaction can be performed, for example, by a method described in T. W. Greene, Protective Groups in Organic Synthesis, Fifth Edition, Wiley, New York, 2014.

As can be easily understood by those skilled in the art, the desired compound of the present invention can be easily produced by properly using these deprotection reactions.

In the present specification, the compound used as the starting material in each of the reactions, for example, the compound represented by the general formula (A), the general formula (II), the general formula (III), the general formula (IV), the general formula (C), or the general formula (VI), is known or can be easily prepared by a known method.

In the present specification, a reaction which involves heating in each of the reactions can be performed by using a water bath, an oil bath, a sand bath or a microwave as apparent to those skilled in the art.

In the present specification, a solid phase-supported reagent which is supported by a macromolecular polymer (such as polystyrene, polyacrylamide, polypropylene and polyethylene glycol) may be used appropriately, in each of the reactions.

In the present specification, the reaction product in each of the reactions can be purified by a conventional purification means. Examples of the purification means include distillation under a normal pressure or reduced pressure, high performance liquid chromatography which uses silica gel or magnesium silicate, thin-layer chromatography, an ion exchange resin, a scavenger resin, column chromatography, washing, recrystallization and the like. The purification may be performed at each of reactions or may be performed after the completion of several reactions.

[Toxicity]

The toxicity of the compound of the present invention is sufficiently low, and the compound of the present invention can be used as a pharmaceutical safely.

[Application to Pharmaceuticals]

The compound of the present invention has an $S1P_5$ (EDG-8) receptor agonist activity, and therefore, is useful as an agent for preventing and/or treating an $S1P_5$-mediated disease. Examples of the $S1P_5$-mediated disease include neurodegenerative disease, autoimmune disease, infection, cancer and the like.

In addition, the compound of the present invention has an $S1P_5$ (EDG-8) receptor agonist activity, and therefore, is useful as an agent for preventing and/or treating cancer through the activating action of the tumor immunity.

In the present invention, examples of the neurodegenerative disease include anxiety-related disease (social anxiety disorder, anxiety neurosis, obsessive-compulsive disorder and Post-Traumatic Stress Disorder (PTSD)), polyglutamine disease, retinitis pigmentosa, neurosis, convulsion, panic disorder, sleep disorder, depression, reactive depression, epilepsy, Parkinson's disease, parkinsonian syndrome, Down's syndrome, schizophrenia, autonomic ataxia, Huntington's disease, Alzheimer-type dementia, affective disorder (including depressive disorder and bipolar disorder), cognitive impairment, migraine, tension-type headache, cluster headache, dissociative disorder, amyotrophic lateral sclerosis, neuromyelitis optica, optic neuritis, acute disseminated encephalomyelitis, allergic encephalomyelitis, Marchiafava-Bignami disease, Binswanger's disease, progressive multifocal leukoencephalopathy, postinfectious encephalitis, central pontine myelinolysis, adrenoleukodystrophy, multiple system atrophy, Krabbe disease, metachromatic leukodystrophy, Alexander's disease, Canavan disease, Cockayne syndrome, Pelizaeus-Merzbacher disease, Hurler's syndrome, Lowe syndrome, spinal cord injury, transverse myelitis, spinocerebellar degeneration, chronic inflammatory demyelinating polyradiculoneuropathy (CIDP), Guillain-Barre syndrome, phenylketonuria, Refsum's disease, Charcot-Marie-Tooth disease, Gaucher's disease, Niemann-Pick disease, multiple sclerosis, fragile X syndrome, autism, insomnia, nervous cough, psychogenic convulsive seizure, psychogenic syncopal attack, writer's cramp, spasmodic torticollis, neuropathy, neurodegeneration with brain iron accumulation, Lewy body dementia and the like.

In the present invention, neurodegenerative disease is preferably Alzheimer-type dementia, Parkinson's disease, multiple system atrophy, multiple sclerosis or Lewy body dementia.

In the present invention, examples of the autoimmune disease include inflammatory bowel disease, arthritis, lupus, rheumatism, psoriatic arthritis, osteoarthritis, Still's disease, juvenile arthritis, type 1 diabetes mellitus, myasthenia gravis, Hashimoto's thyroiditis, iodine thyroiditis, Basedow's disease, Sjogren's syndrome, Addison disease, opsoclonus-myoclonus syndrome, ankylosing spondylitis, antiphospholipid syndrome, aplastic anemia, autoimmune hepatitis, celiac disease, Goodpasture's syndrome, idiopathic thrombocytopenic purpura, scleroderma, primary biliary cirrhosis, Reiter's disease, Takayasu's arteritis, temporal arteritis, warm autoimmune hemolytic anemia, Wegener's granulomatosis, psoriasis, alopecia universalis, Behcet's disease, chronic fatigue syndrome, autonomic neuropathy, endometriosis, interstitial cystitis, myotonia, vulvodynia and systemic lupus erythematosus.

In the present invention, examples of the infection include symptoms which are developed by the infection of a normal cell in vivo with a pathogenic microorganism and proliferation of the pathogenic microorganism. Representative examples of the pathogenic microorganism include one or more kinds of a virus, a bacterium, a fungus and the like. The above-described pathogenic microorganism also includes a *Rickettsia*, a *Chlamydia*, a protozoan, a parasite and the like.

In the present invention, examples of the virus which causes infection include human hepatitis virus (such as hepatitis B virus, hepatitis C virus, hepatitis A virus and hepatitis E virus), human retrovirus, human immunodeficiency virus (such as HIV1 and HIV2), human T-cell leukemia virus or human T-lymphotropic virus (such as HTLV1 and HTLV2), herpes simplex virus type 1 or type 2, Epstein-Barr (EB) virus, cytomegalovirus, varicella-zoster virus, human herpesvirus (such as human herpesvirus 6), poliovirus, measles virus, rubella virus, Japanese encephalitis virus, mumps virus, influenza virus, common cold virus (such as adenovirus, enterovirus and rhinovirus), virus which causes severe acute respiratory syndrome (SARS), Ebola virus, West Nile virus, flavivirus, echovirus, Coxsackie virus, coronavirus, respiratory syncytial virus, rotavirus, norovirus, sapovirus, parvovirus, vaccinia virus, HTL virus, dengue virus, papilloma virus, molluscum contagiosum virus, rabies virus, JC virus, arbovirus, encephalitis virus, hantavirus and Ebola virus.

In the present invention, examples of the bacterium which causes infection include *Vibrio cholerae, Salmonella enterica, Escherichia coli, Legionella, Bacillus anthracis, Helicobacter pylori, Listeria monocytogenes, Mycobacterium tuberculosis*, nontuberculous mycobacteria, *Staphylococcus, Streptococcus, Streptococcus pneumoniae, Neisseria meningitidis, Klebsiella pneumoniae, Serratia, Corynebacterium diphtheriae, Brucella, Bartonella henselae, Erysipelothrix rhusiopathiae, Actinomyces, Borrelia burgdorferi, Clostridium perfringens, Shigella dysenteriae, Yersinia pestis, Clostridium tetani, Enterobacter* and the like.

In the present invention, examples of the fungus which causes infection include *Candida, Aspergillus, Cryptococcus, Blastomyces, Coccidioides, Histoplasma, Paracoccidioides* and *Sporothrix*.

In the present invention, examples of the protozoan which causes infection include *Plasmodium* and *Toxoplasma gondii*.

In the present invention, examples of the parasite which causes infection include *Entamoeba histolytica, Ascaris lumbricoides, Babesia, Cryptosporidium, Giardia lamblia, Ancylostoma, Enterobius vermicularis, Schistosoma, Cestoda, Trichinella spiralis* and *Trichuris trichiura*.

In the present invention, examples of other microorganisms which cause infection include *Mycoplasma* and *Spirochaeta*.

In the present invention, examples of cancer include cancer associated with cerebral nerve (such as pediatric brain tumors (for example, neuroblastoma, medulloblastoma, astrocytoma (juvenile pilocytic astrocytoma), ependymoma, craniopharingioma, germ cell tumors, optic nerve glioma, choroid plexus papilloma and pontine glioma), adult brain tumors (for example, adult astrocytoma, adult malignant astrocytoma, adult glioblastoma, adult ependymoma, adult malignant ependymoma, adult malignant oligodendroglioma, adult medulloblastoma, adult meningioma and adult malignant meningioma), glioma (for example, astrocytoma, oligodendroglioma, ependymoma and brain stem glioma), pituitary adenoma, acoustic schwannoma, retinoblastoma and uveal malignant melanoma), respiratory tract cancer (such as pharyngeal cancer (for example, nasopharyngeal cancer, oropharyngeal cancer and hypopharyngeal cancer), laryngeal cancer, nasal sinus cancer, lung cancer (for example, small cell cancer and non-small-cell cancer), thymoma and mesothelioma), gastrointestinal cancer (such as esophageal cancer, gastric cancer, duodenal cancer and large bowel cancer (for example, colon cancer, rectal cancer and anal cancer)), oral cancer (such as gingival cancer, tongue cancer and salivary gland cancer), urinary system cancer (such as penile cancer, renal pelvis ureter cancer, renal cell cancer, testicular tumor, prostate cancer and bladder cancer), cancers that affect women (such as vulvar cancer, uterine cancer (for example, cervical cancer and endometrial cancer), uterine sarcoma, trophoblastic disease (for example, hydatidiform mole, choriocarcinoma, placental-site trophoblastic tumor and persistent trophoblastic disease), vaginal cancer, breast cancer, breast sarcoma, ovarian cancer and ovarian germ cell tumor), skin cancer (such as melanoma (malignant melanoma) (for example, malignant lentiginous melanoma, superficial spreading melanoma, nodular melanoma, acral lentiginous melanoma and erosive melanoma), mycosis fungoides, squamous cell carcinoma, basal cell carcinoma, premonitory signs of skin cancer intraepidermal carcinoma (for example, actinic keratosis, Bowen's disease and Paget's disease), lymphomatoid papulosis, cutaneous CD30 positive anaplastic large cell lymphoma, Sezary syndrome and cutaneous B-cell lymphoma), bone and muscle cancer (such as osteosarcoma, soft tissue sarcoma, rhabdomyosarcoma, synovial sarcoma and liposarcoma), thyroid cancer, carcinoid, liver cancer (hepatoma), hepatoblastoma, bile duct cancer, gallbladder cancer, pancreatic cancer, pancreatic endocrine tumors (such as insulinoma, gastrinoma and VIPoma), carcinoma of unknown primary, hereditary tumors familial tumors (such as hereditary nonpolyposis colorectal cancer, familial adenomatous polyposis, hereditary breast and ovarian cancer syndrome, Li-Fraumeni syndrome, hereditary melanoma, Wilms' tumor, hereditary papillary renal cell carcinoma, von Hippel-Lindau syndrome and multiple endocrine neoplasia), leukemia (such as acute myeloid leukemia, acute lymphoblastic leukemia, myelodysplastic syndrome, chronic myeloid leukemia chronic myeloproliferative disorder, adult T-cell leukemia-lymphoma, chronic lymphocytic leukemia and small lymphocytic lymphoma), multiple myeloma, primary macroglobulinemia, malignant lymphoma (such as Hodgkin's lymphoma, non-Hodgkin's lymphoma (intermediate- and high-grade lymphomas, Burkitt's lymphoma, lymphoblastic lymphoma, follicular lymphoma, mantle-cell lymphoma, MALT (Mucosa-Associated Lymphoid Tissue) lymphoma and NK (natural killer) cell lymphoma)) and the like.

The compound of the present invention may be administered as a combined medicine by being combined with other drug(s) for the purpose of:
1) complementation and/or enhancement of the preventing and/or treating effect of the compound,
2) improvement in kinetics absorption, and reduction of the dose of the compound, and/or
3) reduction of the side effect of the compound.

The combined medicine of the compound of the present invention with other drug(s) may be administered in the form of a compounding agent in which both ingredients are compounded in a preparation or may be administered by means of separate preparations. The case of being administered by means of separate preparations includes concomitant administration and administrations with a time difference. In addition, in the case of the administrations with a time difference, the compound of the present invention may be firstly administered, followed by administration of the other drug(s). Alternatively, the other drug(s) may be firstly administered, followed by administration of the compound of the present invention. A method for administering the compound of the present invention and that for administering the other drug(s) may be the same or different.

The disease against which the above-described combined medicine exhibits the preventing and/or treating effect is not particularly limited as long as the disease is that against which the preventing and/or treating effect of the compound of the present invention is complemented and/or enhanced.

In addition, the combined medicine which is combined with the compound of the present invention includes not only those which have been found up to now but also those which will be found in future.

Examples of the other drug(s) for complementation and/or enhancement of the preventing and/or treating effect of the compound of the present invention on neurodegenerative disease include an acetylcholinesterase inhibitor, a nicotinic receptor modulator, a suppressor of production, secretion, accumulation, agglutination and/or deposition of β amyloid protein (such as a β secretase inhibitor, a γ secretase inhibitor, a drug having β amyloid protein agglutination inhibitory action, a β amyloid vaccine and a catabolic enzyme of β amyloid), an activator of brain function (such as an activator of brain metabolism and a cerebral circulation improving drug), a dopamine receptor agonist (a dopamine receptor stimulant), a dopamine release accelerating drug (a dopamine secretion accelerating drug or a dopamine release accelerating drug), a dopamine uptake inhibitor, a dopamine agonist, a dopamine antagonist, lithium carbonate, a serotonergic agonist, a serotonin antagonist (such as a 5-$HT_{2A}$ antagonist, a 5-$HT_3$ antagonist, a 5-$HT_4$ antagonist and a 5-$HT_7$ antagonist), a monoamine oxidase (MAO) inhibitor, an aromatic L-amino acid decarboxylase inhibitor (DCI), a norepinephrine (noradrenaline) supplement, an anticholinergic drug, a catechol-O-methyltransferase (COMT) inhibitor, a therapeutic drug for amyotrophic lateral sclerosis, a therapeutic drug for hyperlipidemia, an apoptosis inhibitor, a nerve regeneration differentiation accelerating drug, an antihypertensive drug, a therapeutic drug for diabetes, a therapeutic drug for diabetic complication, an antidepressant (such as a tricyclic antidepressant and a tetracyclic antidepressant), an antianxiety drug, an antiepileptic drug, an anticonvulsant drug, an antispasmodic drug, a nonsteroidal anti-inflammatory drug, an anti-cytokine drug (such as a TNF inhibitor and an MAP kinase inhibitor), a steroid, a sex hormone or a derivative thereof (such as progesterone, estradiol and estradiol benzoate), a thyroid hormone, a parathyroid hormone (such as PTH), a calcium channel blocker (a calcium antagonist), a calcium receptor antagonist, an opioid receptor agonist, an N-methyl-D-2-amino-5-D-aspartate (NMDA) receptor antagonist, a VR-1 receptor agonist, a neuromuscular junction blocking drug, a cannabinoid-2 receptor agonist, a GABAA receptor modulator (such as a GABAA receptor agonist), a GABAB receptor modulator, prostaglandins, a cholecystokinin antagonist, a nitric oxide synthase (NOS) inhibitor, a local anesthetic, a neurotrophic factor (such as neurotrophin, TGF-β superfamily, a neurokinin family and a growth factor), a sympathomimetic drug, a parasympathomimetic drug, a sympatholytic drug, a prostaglandin receptor antagonist, a prostaglandin receptor agonist, a carbonic anhydrase inhibitor, a hyperosmotic drug, a vasodilator drug, a metabolic activator, a diuretic drug (such as a thiazide diuretic drug, a loop diuretic drug and a potassium-sparing diuretic drug), a peripheral blood flow improving drug, an immunosuppressive drug (such as a dimethyl fumarate, glatiramer acetate, interferon beta-1a, interferon beta-1b, fingolimod), an immunoglobulin, an α-amino-3-hydroxy-5-methyl-4-isoxazolepropionic acid (AMPA)/kainic acid receptor antagonist, an Rho-kinase inhibitor, vitamins (such as vitamin B6 and vitamin B12), a cyclooxygenase (COX)-2 inhibitor, an anti-dizziness drug, a therapeutic drug for anemia, a therapeutic drug for heavy metal poisoning, a muscarinic receptor agonist, an aldose reductase inhibitor, a nerve regeneration accelerating drug, a protein kinase C (PKC) inhibitor, an advanced glycation end product (AGE) inhibitor, a reactive oxygen species scavenger, a muscle relaxant and the like.

Examples of the other drug(s) for complementation and/or enhancement of the preventing and/or treating effect of the compound of the present invention on autoimmune disease include an immunosuppressive drug (such as a dimethyl fumarate, glatiramer acetate, interferon beta-1a, interferon beta-1b, fingolimod), a steroid, a disease-modifying antirheumatic drug, an elastase inhibitor, a cannabinoid-2 receptor agonist, a prostaglandin, a prostaglandin synthase inhibitor, a phosphodiesterase inhibitor, a metalloprotease inhibitor, an adhesion molecule inhibitor, an anti-cytokine protein preparation such as an anti-TNF-α preparation, an anti-IL-1 preparation and an anti-IL-6 preparation, a cytokine inhibitor, a nonsteroidal anti-inflammatory drug and an anti-CD 20 antibody.

Examples of the other drug(s) for complementation and/or enhancement of the preventing and/or treating effect of the compound of the present invention on infection include an antiviral drug, an antibiotic, an antifungal drug, an antiparasitic drug, an antiprotozoal drug and the like.

Examples of the other drug(s) for complementation and/or enhancement of the preventing and/or treating effect of the compound of the present invention on cancer include an alkylating drug, an antimetabolite, an anticarcinogenic antibiotic, a plant alkaloid drug, a hormonal drug, a platinum compound, an anti-CD 20 antibody and other anticancer agents.

The compound of the present invention is normally administered systemically or locally, in the form of an oral preparation or a parenteral preparation. Examples of the oral preparation include an oral liquid preparation (such as an elixir, a syrup, a pharmaceutically acceptable liquid agent, a suspension and an emulsion), an oral solid preparation (such as a tablet (including a sublingual tablet and an orally disintegrating tablet), a pill, a capsule (including a hard capsule, a soft capsule, a gelatin capsule and a microcapsule), a powdered agent, a granule and a lozenge) and the like. Examples of the parenteral preparation include a liquid preparation (such as an injection preparation (such as a subcutaneous injection preparation, an intravenous injection preparation, an intramuscular injection preparation, an intraperitoneal injection preparation and a preparation for drip infusion), an eye drop (such as an aqueous eye drop (such as an aqueous ophthalmic solution, an aqueous ophthalmic suspension, a viscous eye drop and a solubilized eye drop) and a non-aqueous eye drop (such as a non-aqueous ophthalmic solution and a non-aqueous ophthalmic suspension))), an external preparation (such as an ointment (such as an ophthalmic ointment)), an ear drop, an patch and the like. The above-described preparation may be a controlled-release preparation such as an immediate-release preparation and a sustained release preparation. The above-described preparation can be prepared by a known method, for example, by a method described in Pharmacopeia of Japan or the like.

The oral liquid preparation as an oral preparation is prepared, for example, by dissolving, suspending or emulsifying an active ingredient in a generally used diluent (such as purified water, ethanol and a mixed liquid thereof). In addition, the liquid preparation may further contain a wetting agent, a suspending agent, an emulsifying agent, a sweetening agent, a flavoring agent, a perfume, a preservative, a buffer agent and the like.

The oral solid preparation as an oral preparation is prepared, for example, by mixing an active ingredient with an excipient (such as lactose, mannitol, glucose, microcrystalline cellulose and starch), a bonding agent (such as hydroxypropyl cellulose, polyvinylpyrrolidone and magnesium aluminometasilicate), a disintegrating agent (such as calcium cellulose glycolate), a lubricant (such as magnesium stearate), a stabilizer, a solubilizing agent (such as glutamic acid and aspartic acid) and the like by a routine procedure. In addition, if necessary, the active ingredient may be coated with a coating agent (such as white soft sugar, gelatin, hydroxypropyl cellulose and hydroxypropyl methylcellulose phthalate) or may be coated with two or more layers.

The external preparation as a parenteral preparation is prepared by a known method or according to a normally used formulation. For example, an ointment is prepared by triturating or melting an active ingredient in a base. An ointment base is selected from those which are known and those which are normally used. For example, one selected from the followings is used or two or more kinds selected from the followings are used by being mixed together: a higher fatty acid or a higher fatty acid ester (such as adipic acid, myristic acid, palmitic acid, stearic acid, oleic acid, an adipate ester, a myristate ester, a palmitate ester, a stearate ester and an oleate ester), waxes (such as beeswax, whale wax and ceresin), a surface-active agent (such as a polyoxyethylene alkyl ether phosphoric ester), a higher alcohol (such as cetanol, stearyl alcohol and cetostearyl alcohol), a silicone oil (such as dimethyl polysiloxane), hydrocarbons (such as hydrophilic petrolatum, white petrolatum, purified lanolin and liquid paraffin), glycols (such as ethylene glycol, diethylene glycol, propylene glycol, polyethylene glycol and macrogol), a vegetable oil (such as castor oil, olive oil, sesame oil and turpentine oil), an animal oil (such as mink oil, egg-yolk oil, squalane and squalene), water, an absorption promoter and an agent for preventing skin rash. In addition, a moisturizing agent, a preservative, a stabilizing agent, an antioxidant, a flavoring agent and the like may be contained.

The injection preparation as a parenteral preparation includes a solution, a suspension, an emulsion and a solid injection preparation which is used at the time of use by being dissolved or suspended in a solvent. The injection preparation is used, for example, by dissolving, suspending or emulsifying an active ingredient in a solvent. Examples of the solvent used include distilled water for injection, saline, a vegetable oil, alcohols such as propylene glycol, polyethylene glycol and ethanol and the like as well as a mixture thereof. In addition, the injection preparation may contain a stabilizer, a solubilizing agent (such as glutamic acid, aspartic acid and polysorbate 80 (registered trademark)), a suspending agent, an emulsifying agent, an analgesic, a buffer agent, a preservative and the like. The above-described injection preparation is prepared by being sterilized at the final process or by an aseptic manipulation method. In addition, the above-described injection preparation can be also used by preparing a sterile solid preparation, for example, a lyophilized preparation, and dissolving the sterile solid preparation in sterilized or sterile distilled water for injection or other solvent before use of the preparation.

In order to use the compound of the present invention or the combined medicine of the compound of the present invention with other drug(s) for the above-described purpose, the compound of the present invention or the combined medicine of the compound of the present invention with other drug(s) is normally administered systemically or locally, in the form of an oral preparation or a parenteral preparation. The dose varies depending on the age, the body weight, the symptom, the therapeutic effect, the method for administration, the duration of the treatment and the like. However, normally, the dose per adult is in the range of from 1 ng to 1,000 mg per administration, from one to several oral administrations per day or the dose per adult is in the rage of from 0.1 ng to 10 mg per administration, from one to several parenteral administrations per day. Alternatively, the dose is continuously administrated intravenously for a period of time in the range of 1 to 24 hours per day. Of course, the dose varies depending on various factors as described above, and therefore, there are some cases in which a dose below the above-described dose is sufficient and there are other cases in which administration of a dose which exceeds the above-described range is required.

The present application provides, for example, the following embodiments.

[1] A compound represented by the general formula (V) or a pharmaceutically acceptable salt thereof:

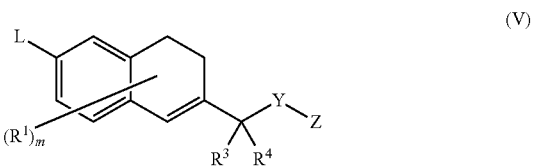

(V)

[wherein L is a branched or linear chain group composed of atoms selected from a carbon atom, an oxygen atom, a nitrogen atom, and a sulfur atom, in which the number of atoms in the main chain thereof is 3 to 8, and the chain group may contain 1 to 3 heteroatoms selected from an oxygen atom, a nitrogen atom, and a sulfur atom, provided that a carbon atom in L may be substituted with 1 to 13 halogen atoms, Y represents

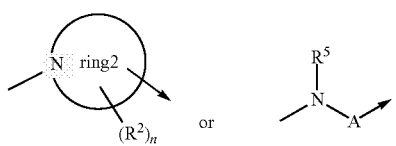

wherein each group is bound to Z through a bond represented by an arrow,

A represents a C3-7 cycloalkylene group which may be substituted or a C1-4 alkylene group which may be substituted, $R^1$ represents a C1-4 alkyl group, a C3-6 cycloalkyl group which may be substituted with a halogen, a C1-4 alkoxy group which may be substituted with a halogen, a C1-4 haloalkyl group, a halogen atom, or a hydroxy group, R² represents a C1-4 alkyl group, a C1-4 alkoxy group which may be substituted with a halogen, a C1-4 haloalkyl group, a halogen atom, or a hydroxy group, R³, R⁴, and R⁵ each independently represent a hydrogen atom, a C1-4 alkyl group, a C3-6 cycloalkyl group which may be substituted with a halogen, or a C1-4 haloalkyl group, Z represents (1) a carboxyl group which may be substituted with one C1-8 alkyl group, (2) a hydroxy group which may be substituted with one C1-8 alkyl group, (3) a hydroxamic acid group which may be substituted with one to two C1-8 alkyl groups, (4) a sulfonic acid group which may be substituted with one C1-8 alkyl group, (5) a boronic acid group which may be substituted with one to two C1-8 alkyl groups, (6) a carbamoyl group which may be substituted with (i) one to two C1-8 alkyl groups or (ii) one to two sulfonyl groups which may be substituted with a C1-4 alkyl group, (7) a sulfamoyl group which may be substituted with (i) one to two C1-8 alkyl groups or (ii) one to two C2-8 acyl groups, (8) a sulfoximine group which may be substituted with one to two C1-8 alkyl groups, or (9) a tetrazolyl group, ring 2 represents a 3- to 7-membered nitrogen-containing heterocycle, m represents an integer of 0 to 6, n represents an integer of 0 to 5, when m is 2 or more, a plurality of R¹s may be the same or different, and when n is 2 or more, a plurality of R$^e$s may be the same or different, provided that each hydrogen atom may be a deuterium atom or a tritium atom],

[2] The compound or a pharmaceutically acceptable salt thereof according to the above [1], wherein the compound is a compound represented by the general formula (V-1):

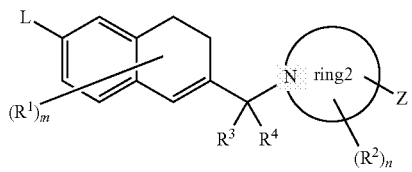

(V-1)

[wherein all the symbols represent the same meanings as described in the above [1], provided that each hydrogen atom may be a deuterium atom or a tritium atom],

[3] The compound or a pharmaceutically acceptable salt thereof according to the above [1] or [2], wherein L is (1) —O—(C2-7 alkyl), (2) —O—(C2-7 alkenyl), (3) —O—(C2-7 alkynyl), (4) —O—(C1-5 alkylene)-OCH₃, (5) —O—(C1-4 alkylene)-OCH₂CH₃, (6) —CH₂O—(C1-6 alkyl), (7) —CH₂O—(C2-6 alkenyl), (8) —CH₂O—(C2-6 alkynyl), (9) —CH₂CH₂O—(C1-5 alkyl), (10) —CH₂CH₂O—(C2-5 alkenyl), (11) —CH₂CH₂O—(C2-5 alkynyl), (12) —S—(C2-7 alkyl), (13) —S—(C2-7 alkenyl), (14) —S—(C2-7 alkynyl), (15) —NR⁶—(C2-7 alkyl), (16) —NR⁶—(C2-7 alkenyl), (17) —NR⁶—(C2-7 alkynyl), (18) a C3-8 alkyl group, (19) a C3-8 alkenyl group, or (20) a C3-8 alkynyl group, and R⁶ represents a hydrogen atom or a C1-4 alkyl group, provided that a carbon atom in each group may be substituted with 1 to 13 halogen atoms,

[4] The compound or a pharmaceutically acceptable salt thereof according to the above [1] or [2], wherein L is a branched or linear chain group in which the number of atoms in the main chain is 4 to 7,

[5] The compound or a pharmaceutically acceptable salt thereof according to the above [1] or [2], wherein L is (1) —O—(C3-6 alkyl), (2) —O—(C3-6 alkenyl), (3) —O—(C3-6 alkynyl), (4) —O—(C1-4 alkylene)-OCH₃, (5) —O—(C1-3 alkylene)-OCH₂CH₃, (6) —CH₂O—(C2-5 alkyl), (7) —CH₂O—(C2-5 alkenyl), (8) —CH₂O—(C2-5 alkynyl), (9) —CH₂CH₂O—(C1-4 alkyl), (10) —CH₂CH₂O—(C2-4 alkenyl), (11) —CH₂CH₂O—(C2-4 alkynyl), (12) —S—(C3-6 alkyl), (13) —S—(C3-6 alkenyl), (14) —S—(C3-6 alkynyl), (15) —NR⁶—(C3-6 alkyl), (16) —NR⁶—(C3-6 alkenyl), (17) —NR⁶—(C3-6 alkynyl), (18) a C4-7 alkyl group, (19) a C4-7 alkenyl group, or (20) a C4-7 alkynyl group, and R⁶ represents a hydrogen atom or a C1-4 alkyl group, provided that a carbon atom in each group may be substituted with 1 to 13 halogen atoms,

[6] The compound or a pharmaceutically acceptable salt thereof according to any one of the above [1] to [5], wherein ring 2 is a 3- to 7-membered nitrogen-containing saturated heterocycle (preferably azetidine, pyrrolidine, piperidine, or perhydroazepine),

[7] The compound or a pharmaceutically acceptable salt thereof according to the above [1] or [2], wherein the compound is a compound represented by the general formula (V-2):

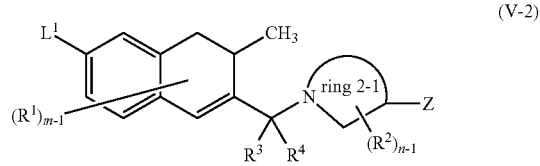

(V-2)

[wherein L¹ is a branched or linear chain group composed of atoms selected from a carbon atom, an oxygen atom, a nitrogen atom, and a sulfur atom, in which the number of atoms in the main chain thereof is 4 to 7, and the chain group may contain 1 to 3 heteroatoms selected from an oxygen atom, a nitrogen atom, and a sulfur atom, provided that a carbon atom in L¹ may be substituted with 1 to 13 halogen atoms, ring 2-1 represents a 3- to 7-membered nitrogen-containing saturated heterocycle, m-1 represents an integer of 0 to 2, n-1 represents an integer of 0 to 2, when m-1 is 2, a plurality of les may be the same or different, when n-1 is 2, a plurality of R$^e$s may be the same or different, and the other symbols represent the same meanings as described in the above [1], provided that each hydrogen atom may be a deuterium atom or a tritium atom],

[8] The compound or a pharmaceutically acceptable salt thereof according to any one of the above [1] to [7], wherein Z is a carboxyl group which may be substituted with one C1-8 alkyl group, or a tetrazolyl group,

[9] The compound or a pharmaceutically acceptable salt thereof according to the above [7] or [8], wherein L¹ is (1) —O—(C3-6 alkyl), (2) —O—(C3-6 alkenyl), (3) —O—(C3-6 alkynyl), (4) —O—(C1-4 alkylene)-OCH₃, (5)

—O—(C1-3 alkylene)-OCH$_2$CH$_3$, (6) —CH$_2$O—(C2-5 alkyl), (7) —CH$_2$O—(C2-5 alkenyl), (8) —CH$_2$O—(C2-5 alkynyl), (9) —CH$_2$CH$_2$O—(C1-4 alkyl), (10) —CH$_2$CH$_2$O—(C2-4 alkenyl), (11) —CH$_2$CH$_2$O—(C2-4 alkynyl), (12) —S—(C3-6 alkyl), (13) —S—(C3-6 alkenyl), (14) —S—(C3-6 alkynyl), (15) —NR$^6$—(C3-6 alkyl), (16) —NR$^6$—(C3-6 alkenyl), (17) —NR$^6$—(C3-6 alkynyl), (18) a C4-7 alkyl group, (19) a C4-7 alkenyl group, or (20) a C4-7 alkynyl group, and R$^6$ represents a hydrogen atom or a C1-4 alkyl group, provided that a carbon atom in each group may be substituted with 1 to 13 halogen atoms,

[10] The compound or a pharmaceutically acceptable salt thereof according to any one of the above [1] to [9], wherein R$^1$ is a C1-4 alkyl group or a halogen atom,

[11] The compound or a pharmaceutically acceptable salt thereof according to any one of the above [7] to [10], wherein ring 2-1 is azetidine, pyrrolidine, piperidine, or perhydroazepine,

[12] The compound or a pharmaceutically acceptable salt thereof according to the above [1] or [2], wherein the compound is (1) 1-[((3R)-6-butoxy-3-methyl-3,4-dihydronaphthalen-2-yl)methyl]azetidine-3-carboxylic acid, (2) 1-[((3S)-6-butoxy-3-methyl-3,4-dihydronaphthalen-2-yl) methyl]azetidine-3-carboxylic acid, (3) 1-[((3S)-3-methyl-6-pentoxy-3,4-dihydronaphthalen-2-yl)methyl]azetidine-3-carboxylic acid, (4) 1-[[(3S)-3-methyl-6-(4,4,4-trifluorobutoxy)-3,4-dihydronaphthalen-2-yl]methyl] azetidine-3-carboxylic acid, (5) 3-fluoro-1-[[(3S)-3-methyl-6-(3,4,4-trifluorobut-3-enoxy)-3,4-dihydronaphthalen-2-yl] methyl]azetidine-3-carboxylic acid, (6) 1-[[(3S)-3-methyl-6-(1,1,2,2,3,3,4,4,4-nonadeuteriobutoxy)-3,4-dihydronaphthalen-2-yl]methyl]azetidine-3-carboxylic acid, (7) (3R)-1-[[(3S)-3-methyl-6-(4,4,4-trifluorobutoxy)-3,4-dihydronaphthalen-2-yl]methyl]pyrrolidine-3-carboxylic acid, (8) 1-[[(3S)-3-methyl-6-((R)-3,3,3-trifluoro-2-methylpropoxy)-3,4-dihydronaphthalen-2-yl]methyl]azetidine-3-carboxylic acid, (9) 1-[[(3S)-3-methyl-6-((S)-3,3,3-trifluoro-2-methylpropoxy)-3,4-dihydronaphthalen-2-yl] methyl]azetidine-3-carboxylic acid, (10) 3-fluoro-1-[[(3S)-3-methyl-6-[(E)-4,4,4-trifluorobut-2-enoxy]-3,4-dihydronaphthalen-2-yl]methyl]azetidine-3-carboxylic acid, (11) 3-fluoro-1-{[[(3S)-3-methyl-6-(3,3,3-trifluoropropoxy)-3,4-dihydro-2-naphthalenyl]methyl}-3-azetidinecarboxylic acid, (12) cis-3-({1-[(3S)-3-methyl-6-(4,4,4-trifluorobutoxy)-3,4-dihydro-2-naphthalenyl]ethyl}amino)cyclobutanecarboxylic acid, or (13) 1-{[(3S)-3-methyl-6-(propoxymethyl)-3,4-dihydro-2-naphthalenyl]methyl}-3-azetidinecarboxylic acid,

[13] A pharmaceutical composition comprising the compound represented by the general formula (V) or a pharmaceutically acceptable salt thereof according to the above [1],

[14] The pharmaceutical composition according to the above [13], which is an S1P$_5$ agonist,

[15] The pharmaceutical composition according to the above [13] or [14], which is a prophylactic and/or therapeutic agent for an S1P$_5$-mediated disease,

[16] The pharmaceutical composition according to the above [15], wherein the S1P$_5$-mediated disease is a neurodegenerative disease, an autoimmune disease, an infectious disease, or cancer,

[17] The pharmaceutical composition according to the above [16], wherein the S1P$_5$-mediated disease is a neurodegenerative disease, and the neurodegenerative disease is schizophrenia, Binswanger's disease, multiple sclerosis, neuromyelitis optica, Alzheimer-type dementia, cognitive impairment, amyotrophic lateral sclerosis, spinocerebellar degeneration, multiple system atrophy, Parkinson's disease, or Lewy body dementia,

[18] A method for preventing and/or treating an S1P$_5$-mediated disease, characterized by administering an effective amount of the compound represented by the general formula (V) or a pharmaceutically acceptable salt thereof according to the above [1] to a mammal,

[19] The compound represented by the general formula (V) or a pharmaceutically acceptable salt thereof according to the above [1] for use in preventing and/or treating an S1P$_5$-mediated disease,

[20] Use of the compound represented by the general formula (V) or a pharmaceutically acceptable salt thereof according to the above [1] for manufacturing a prophylactic and/or therapeutic agent for an S1P$_5$-mediated disease,

[21] A compound represented by general formula (I) or a pharmaceutically acceptable salt thereof:

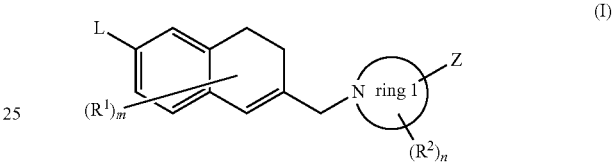

(I)

[wherein L is a branched or linear chain group composed of atoms selected from a carbon atom, an oxygen atom, a nitrogen atom, and a sulfur atom, in which the number of atoms in the main chain thereof is 3 to 8, and the chain group may contain 1 to 3 heteroatoms selected from an oxygen atom, a nitrogen atom, and a sulfur atom, provided that a carbon atom in L may be substituted with 1 to 13 halogen atoms, R$^1$ represents a C1-4 alkyl group, a C3-6 cycloalkyl group which may be substituted with a halogen, a C1-4 alkoxy group which may be substituted with a halogen, a C1-4 haloalkyl group, a halogen atom, or a hydroxy group, R$^2$ represents a C1-4 alkyl group, a C1-4 alkoxy group which may be substituted with a halogen, a C1-4 haloalkyl group, a halogen atom, or a hydroxy group, Z represents (1) a carboxyl group which may be substituted with one C1-8 alkyl group, (2) a hydroxy group which may be substituted with one C1-8 alkyl group, (3) a hydroxamic acid group which may be substituted with one to two C1-8 alkyl groups, (4) a sulfonic acid group which may be substituted with one C1-8 alkyl group, (5) a boronic acid group which may be substituted with one to two C1-8 alkyl groups, (6) a carbamoyl group which may be substituted with (i) one to two C1-8 alkyl groups or (ii) one to two sulfonyl groups which may be substituted with a C1-4 alkyl group, (7) a sulfamoyl group which may be substituted with (i) one to two C1-8 alkyl groups or (ii) one to two C2-8 acyl groups, (8) a sulfoximine group which may be substituted with one to two C1-8 alkyl groups, or (9) a tetrazolyl group, ring 1 represents a 4- to 7-membered nitrogen-containing heterocycle, m represents an integer of 0 to 6, n represents an integer of 0 to 5, when m is 2 or more, a plurality of les may be the same or different, and when n is 2 or more, a plurality of les may be the same or different, provided, provided that each hydrogen atom may be a deuterium atom or a tritium atom]

[22] The compound or a pharmaceutically acceptable salt thereof according to the above [21], wherein L is a branched or linear chain group in which the number of atoms in the main chain is 4 to 7,

[23] The compound or a pharmaceutically acceptable salt thereof according to the above [21] or [22], wherein ring 1 is a 4- to 7-membered nitrogen-containing saturated heterocycle,

[24] The compound or a pharmaceutically acceptable salt thereof according to the above [21], wherein the compound is a compound represented by general formula (I-1):

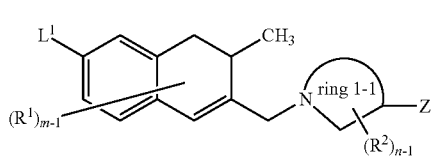

[wherein $L^1$ is a branched or linear chain group composed of atoms selected from a carbon atom, an oxygen atom, a nitrogen atom, and a sulfur atom, in which the number of atoms in the main chain thereof is 4 to 7, and the chain group may contain 1 to 3 heteroatoms selected from an oxygen atom, a nitrogen atom, and a sulfur atom, provided that a carbon atom in $L^1$ may be substituted with 1 to 13 halogen atoms, ring 1-1 represents a 4- to 7-membered nitrogen-containing saturated heterocycle, m-1 represents an integer of 0 to 2, n-1 represents an integer of 0 to 2, when m-1 is 2, a plurality of les may be the same or different, when n-1 is 2, a plurality of les may be the same or different, and the other symbols represent the same meanings as described in the above [21], provided that each hydrogen atom may be a deuterium atom or a tritium atom],

[25] The compound or a pharmaceutically acceptable salt thereof according to the above [24], wherein Z is a carboxyl group which may be substituted with one C1-8 alkyl group,

[26] The compound or a pharmaceutically acceptable salt thereof according to the above [24] or [25], wherein $L^1$ is —O—(C3-6 alkyl group), —O—(C3-6 alkenyl group), —O—(C3-6 alkynyl group), —O—(C2-4 alkylene group)-OCH$_3$, or —O—(C2-3 alkylene group)-OCH$_2$CH$_3$, provided that a carbon atom in each group may be substituted with 1 to 13 halogen atoms,

[27] The compound or a pharmaceutically acceptable salt thereof according to any one of the above [24] to [26], wherein $R^1$ is a C1-4 alkyl group or a halogen atom,

[28] The compound or a pharmaceutically acceptable salt thereof according to any one of the above [24] to [27], wherein ring 1-1 is azetidine, pyrrolidine, piperidine, or perhydroazepine,

[29] The compound or a pharmaceutically acceptable salt thereof according to the above [21], wherein the compound is (1) 1-[((3R)-6-butoxy-3-methyl-3,4-dihydronaphthalen-2-yl)methyl]azetidine-3-carboxylic acid, (2) 1-[((3S)-6-butoxy-3-methyl-3,4-dihydronaphthalen-2-yl)methyl]azetidine-3-carboxylic acid, (3) 1-[((3S)-3-methyl-6-pentoxy-3,4-dihydronaphthalen-2-yl)methyl]azetidine-3-carboxylic acid, (4) 1-[[(3S)-3-methyl-6-(4,4,4-trifluorobutoxy)-3,4-dihydronaphthalen-2-yl]methyl]azetidine-3-carboxylic acid, (5) 3-fluoro-1-[[(3S)-3-methyl-6-(3,4,4-trifluorobut-3-enoxy)-3,4-dihydronaphthalen-2-yl]methyl]azetidine-3-carboxylic acid, (6) 1-[[(3S)-3-methyl-6-(1,1,2,2,3,3,4,4,4-nonadeuteriobutoxy)-3,4-dihydronaphthalen-2-yl]methyl]azetidine-3-carboxylic acid, (7) (3R)-1-[[(3S)-3-methyl-6-(4,4,4-trifluorobutoxy)-3,4-dihydronaphthalen-2-yl]methyl]pyrrolidine-3-carboxylic acid, (8) 1-[[(3S)-3-methyl-6-((R)-3,3,3-trifluoro-2-methylpropoxy)-3,4-dihydronaphthalen-2-yl]methyl]azetidine-3-carboxylic acid, (9) 1-[[(3S)-3-methyl-6-((S)-3,3,3-trifluoro-2-methylpropoxy)-3,4-dihydronaphthalen-2-yl]methyl]azetidine-3-carboxylic acid, or (10) 3-fluoro-1-[[(3S)-3-methyl-6-[(E)-4,4,4-trifluorobut-2-enoxy]-3,4-dihydronaphthalen-2-yl]methyl]azetidine-3-carboxylic acid,

[30] A pharmaceutical composition, comprising the compound represented by the general formula (I) or a pharmaceutically acceptable salt thereof according to the above [21],

[31] The pharmaceutical composition according to the above [30], which is an S1P$_5$ agonist,

[32] The pharmaceutical composition according to the above [30] or [31], which is a prophylactic and/or therapeutic agent for an S1P$_5$-mediated disease,

[33] The pharmaceutical composition according to the above [32], wherein the S1P$_5$-mediated disease is a neurodegenerative disease, an autoimmune disease, an infectious disease, or cancer,

[34] The pharmaceutical composition according to the above [33], wherein the neurodegenerative disease is schizophrenia, Binswanger's disease, multiple sclerosis, neuromyelitis optica, Alzheimer-type dementia, cognitive impairment, amyotrophic lateral sclerosis, spinocerebellar degeneration, multiple system atrophy, Parkinson's disease, or Lewy body dementia,

[35] A method for preventing and/or treating an S1P$_5$-mediated disease, characterized by administering an effective amount of the compound represented by the general formula (I) or a pharmaceutically acceptable salt thereof according to the above [21] to a mammal,

[36] The compound represented by the general formula (I) or a pharmaceutically acceptable salt thereof according to the above [21] for use in preventing and/or treating an S1P$_5$-mediated disease, and

[37] Use of the compound represented by the general formula (I) or a pharmaceutically acceptable salt thereof according to the above [21] for manufacturing a prophylactic and/or therapeutic agent for an S1P$_5$-mediated disease.

EXAMPLES

The present invention will be described in details by referring to Examples hereinbelow, but the present invention is not limited to Examples.

Concerning chromatographic separation or TLC, a solvent in parentheses corresponds to an eluting solvent or a developing solvent employed and a ratio is expressed by volume ratio.

Concerning NMR, a solvent in parentheses corresponds to a solvent used for the measurement.

A compound name used in the present specification is given by using a computer program ACD/Name (registered trademark) of Advanced Chemistry Development, Lexichem Toolkit 1.4.2 of OpenEye Scientific Software, or ChemDraw (registered trademark) Ultra of PerkinElmer. These programs generally denominate a compound according to the IUPAC nomenclature. A compound names used in the present specification also are named according to the IUPAC nomenclature.

LCMS was carried out using Waters i-Class system under the following conditions.

Column: YMC-Triart $C_{18}$ 2.0 mm×30 mm, 1.9 μm, flow rate: 1.0 mL/min, temperature: 30° C., mobile phase A: a 0.1% TFA aqueous solution, mobile phase B: a 0.1% TFA acetonitrile solution, gradient (the ratio of the mobile phase (A) and the mobile phase (B) is described): 0 to 0.10 minutes: (95%:5%), 0.10 to 1.20 minutes: from (95%:5%) to (5%:95%), 1.20 to 1.50 minutes: (5%: 95%)

Example 1: 6-(Benzyloxy)-3,4-dihydronaphthalen-1(2H)-one

To a solution of 6-hydroxy-3,4-dihydronaphthalen-1(2H)-one (CAS registry number: 3470-50-6) (24.3 g) in acetone (160 mL), benzyl bromide (29.4 mL) and potassium carbonate (31.1 g) were added at room temperature and the mixture was stirred at 40° C. for 3.5 hours. After insoluble matters were filtered off, the mixture was concentrated and washed with a mixed solvent of tert-butyl methyl ether (MTBE)-hexane (1:4) to give the title compound (34.5 g) having the following physical property value.

TLC: Rf 0.38 (hexane:ethyl acetate=3:1).

Example 2: 7-(Benzyloxy)-4-methyl-1,2-dihydronaphthalene

To a solution of the compound (34.5 g) prepared in Example 1 in tetrahydrofuran (THF) (300 mL), methylmagnesium bromide (3 mol/L solution in diethyl ether, 55 mL) was added at 0° C., and the mixture was stirred at room temperature for 1 hour. The reaction liquid was cooled to 0° C. and was poured to ice-saturated ammonium chloride aqueous solution. 2 mol/L hydrochloric acid was added to the mixture, and the mixture was stirred at room temperature for 3 hours. The mixture was extracted with ethyl acetate, and the organic layer was washed sequentially with water and saturated saline, was dried over magnesium sulfate and then was concentrated. The obtained residue was purified by silica gel column chromatography (hexane:ethyl acetate=10: 1) to give the title compound (24.8 g) having the following physical property value.

TLC: Rf 0.57 (hexane:ethyl acetate=15:1).

Example 3: 6-(Benzyloxy)-1-methyl-3,4-dihydronaphthalene-2-carbaldehyde

To phosphorus oxychloride (26.7 g), N,N-dimethylformamide (DMF) (60 mL) was added dropwise at 0° C., and the mixture was stirred for 20 minutes. To the mixture, a solution of the compound (24.8 g) prepared in Example 2 in methylene chloride (60 mL) was added dropwise slowly, and the mixture was stirred at room temperature for 90 minutes. The reaction liquid was cooled to 0° C., was poured to ice and was stirred for 30 minutes, and then was extracted with a mixed solvent of hexane-ethyl acetate (1:2). The organic layer was washed sequentially with water and saturated saline, was dried over magnesium sulfate and then was concentrated. The obtained residue was washed with MTBE and dried to give the title compound (19.9 g) having the following physical property value.

TLC: Rf 0.50 (hexane:ethyl acetate=3:1).

Example 4: 6-Hydroxy-1-methyl-3,4-dihydronaphthalene-2-carbaldehyde

To thioanisole (35 mL), trifluoroacetic acid (140 mL) was added at 0° C., and to the mixture, the compound (9.17 g) prepared in Example 3 was added little by little, and the mixture was stirred at room temperature for 4 hours. The reaction liquid was poured to ice, and 5 mol/L sodium hydroxide aqueous solution was added to the reaction solution and the mixture was washed with MTBE. To the aqueous layer, 1 mol/L hydrochloric acid was added, and the mixture was extracted with ethyl acetate. The organic layer was dried over magnesium sulfate, and then was concentrated. The obtained residue was purified by silica gel column chromatography (hexane:ethyl acetate=5:1 to 2:1) to give the title compound (6.03 g) having the following physical property value.

TLC: Rf 0.26 (hexane:ethyl acetate=3:1).

Example 5: Methyl 1-((6-hydroxy-1-methyl-3,4-dihydronaphthalen-2-yl)methyl)azetidine-3-carboxylate To a solution of the compound (8.0 g) prepared in Example 4 in DCM (340 mL), methyl azetidine-3-carboxylate hydrochloride (8.4 g) (CAS Registry Number: 100202-39-9) and diisopropylethylamine (9.6 mL) were added, and the mixture was stirred at room temperature for 30 minutes. To the reaction liquid, sodium triacetoxyborohydride (11.7 g) was added, and the mixture was stirred at room temperature for 16 hours. To the reaction liquid, a saturated sodium hydrogen carbonate aqueous solution was added, and the mixture was extracted with ethyl acetate. The organic layer was washed with saturated saline, dried over magnesium sulfate, and then concentrated under reduced pressure. The obtained residue was purified by silica gel column chromatography (DIOL silica gel, hexane:ethyl acetate=65:35→35: 65) to give the title compound (10.6 g) having the following physical property values.

$^1$H-NMR (CDCl$_3$): δ 7.11, 6.63, 6.57, 3.70, 3.58, 3.45-3.25, 2.60, 2.23, 2.07.

Example 6: Methyl 1-((l-methyl-6-(pentyloxy)-3,4-dihydronaphthalen-2-yl)methyl)azetidine-3-carboxylate To a solution of the compound (123 mg) prepared in Example 5 in DCM (4 mL), sodium hydride (60% in mineral oil, 17 mg) was added, and the mixture was stirred at room temperature for 15 minutes under nitrogen atmosphere. To the reaction liquid, 1-bromopentane (62 mg) was added, and the mixture was stirred for 6 hours. The reaction liquid was diluted with ethyl acetate, washed with water and a 5% lithium chloride aqueous solution, dried over sodium sulfate, and then concentrated under reduced pressure. The obtained residue was purified by silica gel column chromatography (hexane:ethyl acetate=8:2→2:8) to give the title compound (108 mg) having the following physical property values.

$^1$H-NMR (CDCl$_3$): δ 7.18, 6.71, 6.68, 3.95, 3.70, 3.53, 3.35-3.27, 2.67, 2.26, 2.08, 1.78, 1.45-1.35, 0.93.

Example 7: 1-[(1-methyl-6-pentoxy-3,4-dihydronaphthalen-2-yl)methyl]azetidine-3-carboxylic acid

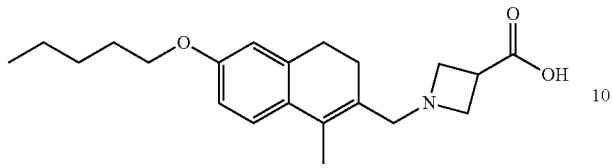

To a solution of the compound (104 mg) prepared in Example 6 in methanol (3 mL), a 2 N sodium hydroxide aqueous solution (3 mL) was added, and the mixture was stirred at room temperature for 2 hours. After the mixture was concentrated under reduced pressure, the obtained residue was purified by silica gel column chromatography (DCM:(DCM:methanol:a concentrated ammonium hydroxide aqueous solution=80:18:2)=9:1→0:10) to give the title compound (84 mg) having the following physical property values.

$^1$H-NMR (DMSO-d$_6$): δ 7.16, 6.74, 6.71, 3.94, 3.40, 3.19, 2.59, 2.16, 2.02, 1.70, 1.36, 0.90;
LCMS: Retention time 0.91 minutes.

Example 7 (1) to 7 (10)

The compound prepared in Example 4 or a corresponding aldehyde derivative instead thereof, methyl azetidine-3-carboxylate hydrochloride, and a corresponding alkyl halide instead of 1-bromopentane were used and subjected to the same reactions as in Example 5→Example 6→Example 7, or the compound prepared in Example 4 or a corresponding aldehyde derivative instead thereof, methyl azetidine-3-carboxylate hydrochloride, and a corresponding alcohol instead of 1-butanol were used and subjected to the same reactions as in Example 5→the below-mentioned Example 8→Example 7 to give the compounds of Examples having the following physical property values.

Example 7 (1): 1-[(6-butoxy-1-methyl-3,4-dihydronaphthalen-2-yl)methyl]azetidine-3-carboxylic acid, ammonia salt $^1$H-NMR (DMSO-d$_6$): δ 7.16, 7.10, 6.74-6.70, 3.94, 3.42, 3.23-3.18, 2.59, 2.26, 2.02, 1.70-1.65, 1.46-1.39, 0.93;
LCMS: Retention time 0.90 minutes.

Example 7 (2): 1-[[1-methyl-6-[(2S)-pentan-2-yl]oxy-3,4-dihydronaphthalen-2-yl]methyl]azetidine-3-carboxylic acid $^1$H-NMR (Acetic Acid-d$_4$): δ 7.29, 6.76, 6.72, 4.64, 4.43-4.41, 4.18, 3.83-3.80, 2.71, 2.30, 2.21, 1.72-1.68, 1.59-1.37, 1.28, 0.94;
LCMS: Retention time 0.93 minutes.

Example 7 (3): 1-[[6-(1,1,2,2,3,3,3-heptadeuteriopropoxy)-1-methyl-3,4-dihydronaphthalen-2-yl]methyl]azetidine-3-carboxylic acid $^1$H-NMR (DMSO-d$_6$): δ 7.16, 6.74, 6.71, 3.40, 3.18, 2.59, 2.16, 2.02;
LCMS: Retention time 0.79 minutes.

Example 7 (4): 1-[[1-methyl-6-(2,2,3,3-tetrafluoropropoxy)-3,4-dihydronaphthalen-2-yl]methyl]azetidine-3-carboxylic acid $^1$H-NMR (DMSO-d$_6$): δ 7.21, 6.87, 6.86, 6.67, 4.56, 3.60-3.00, 2.61, 2.18, 2.03;
LCMS: Retention time 0.79 minutes.

Example 7 (5): 1-[[1-methyl-6-(3,4,4-trifluorobut-3-enoxy)-3,4-dihydronaphthalen-2-yl]methyl]azetidine-3-carboxylic acid $^1$H-NMR (DMSO-d$_6$): δ 7.18, 6.77, 6.75, 4.14, 3.60-3.00, 2.80, 2.60, 2.17, 2.03;
LCMS: Retention time 0.82 minutes.

Example 7 (6): 1-[[1-methyl-6-(3,3,4,4,4-pentadeuteriobutoxy)-3,4-dihydronaphthalen-2-yl]methyl]azetidine-3-carboxylic acid $^1$H-NMR (DMSO-d$_6$): δ 7.16, 6.74, 6.71, 3.94, 3.40, 3.19, 2.59, 2.16, 2.02, 1.66;
LCMS: Retention time 0.85 minutes.

Example 7 (7): 1-[[1-methyl-6-(1,1,2,2,3,3,4,4,4-nonadeuteriobutoxy)-3,4-dihydronaphthalen-2-yl]methyl]azetidine-3-carboxylic acid $^1$H-NMR (DMSO-d$_6$): δ 7.16, 6.74, 6.71, 3.40, 3.19, 2.59, 2.16, 2.02;
LCMS: Retention time 0.85 minutes.

Example 7 (8): 1-[[6-[(E)-but-2-enoxy]-1-methyl-3,4-dihydronaphthalen-2-yl]methyl]azetidine-3-carboxylic acid $^1$H-NMR (DMSO-d$_6$): δ 7.18, 6.75, 6.73, 5.83, 5.68, 4.46, 3.60-3.00, 2.60, 2.16, 2.04, 1.70;
LCMS: Retention time 0.81 minutes.

Example 7 (9): 1-[(6-butoxy-1-ethyl-3,4-dihydronaphthalen-2-yl)methyl]azetidine-3-carboxylic acid $^1$H-NMR (CDCl$_3$): δ 7.24, 6.73, 6.68, 4.35, 4.05, 3.96, 3.91, 3.52-3.35, 2.66, 2.30, 1.76, 1.48, 1.11, 0.97;
LCMS: Retention time 0.89 minutes.

Example 7 (10): 1-[[6-(4,4,4-trifluorobutoxy)-3,4-dihydronaphthalen-2-yl]methyl]azetidine-3-carboxylic acid $^1$H-NMR (DMSO-d$_6$): δ 6.96, 6.72, 6.69, 6.28, 4.00, 3.20, 3.07, 2.68, 2.13, 1.91;
LCMS: Retention time 0.82 minutes.

Example 8: 6-butoxy-3,4-dihydronaphthalen-1(2H)-one

To a solution of 6-hydroxy-3,4-dihydronaphthalen-1(2H)-one (CAS Registry Number: 3470-50-6) (2.0 g) in THF (40 mL), 1-butanol (2.3 mL), triphenylphosphine (6.5 g) and a toluene solution of 2.2 mol/L diethyl azodicarboxylate were added, and the mixture was stirred at room temperature for 5 hours. The reaction liquid was concentrated, and then, the obtained residue was purified by silica gel column chromatography (hexane:ethyl acetate=10:0→8:2) to give the title compound (2.7 g) having the following physical property values.

$^1$H-NMR (CDCl$_3$): δ 8.00, 6.81, 6.70, 4.01, 2.91, 2.60, 2.11, 1.78, 1.49, 0.98.

Example 9: 1-bromo-6-butoxy-3,4-dihydronaphthalene-2-carbaldehyde

A solution of the compound (770 mg) prepared in Example 8 in chloroform (12 mL)/DMF (1.37 mL) was ice-cooled, and tribromide phosphate (0.83 mL) was added thereto, and the mixture was stirred at room temperature for 72 hours. To the reaction liquid, a saturated sodium hydrogen carbonate aqueous solution was added, and the mixture was extracted twice with ethyl acetate. The organic layer was washed with saturated saline, dried over sodium sulfate, and then concentrated under reduced pressure. The obtained residue was purified by silica gel column chromatography (hexane:ethyl acetate=10:0→7:3) to give the title compound (621 mg) having the following physical property values.

$^1$H-NMR (CDCl$_3$): δ 10.20, 7.82, 6.82, 6.72, 4.02, 2.80, 2.61, 1.79, 1.50, 0.99.

Example 10: 6-butoxy-1-cyclopropyl-3,4-dihydronaphthalene-2-carbaldehyde

To a solution of the compound (320 mg) prepared in Example 9 in toluene (5 mL), cyclopropylboric acid (133 mg), a 2 mol/L potassium phosphate aqueous solution (1.6 mL), tricyclohexylphosphine (0.064 mL), and palladium acetate (23 mg) were added, and the mixture was stirred at 90° C. for 5 hours. The reaction liquid was filtered through Celite (trade name), and the filtrate was extracted twice with ethyl acetate. The organic layer was washed with water and saturated saline, dried over sodium sulfate, and then concentrated under reduced pressure. The obtained residue was purified by silica gel column chromatography (hexane:ethyl acetate=10:0→8:2) to give the title compound (271 mg) having the following physical property values.

$^1$H-NMR (CDCl$_3$): δ 10.66, 7.78, 6.80, 6.71, 4.00, 2.67, 2.47, 1.89, 1.78, 1.50, 1.15, 0.98, 0.59.

Example 11: 1-[(6-butoxy-1-cyclopropyl-3,4-dihydronaphthalen-2-yl)methyl]azetidine-3-carboxylic acid

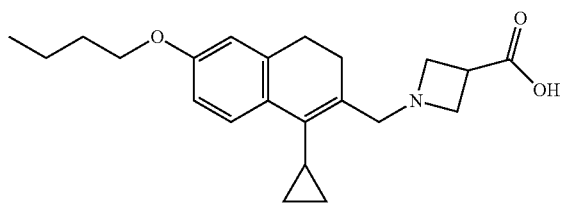 [SMILES: CCCCOc1ccc2c(c1)CCC(CN1CC(C(=O)O)C1)=C2C1CC1]

The compound (270 mg) prepared in Example 10 and methyl azetidine-3-carboxylate hydrochloride (197 mg) were used and subjected to the same reactions as in Example 5→Example 7 to give the title compound (92 mg) having the following physical property values.

$^1$H-NMR (DMSO-d$_6$): δ 7.44, 6.74, 6.67, 3.94, 3.84-2.91, 2.14, 1.67, 1.54, 1.42, 0.96-0.91, 0.24;

LCMS: Retention time 0.96 minutes.

Example 12: 6-methoxy-3-methyl-3,4-dihydronaphthalene-2-carbaldehyde

To a solution of 6-methoxy-3-methyl-3,4-dihydronaphthalen-1(2H)-one (CAS Registry Number: 5563-21-3) (1 g) in methanol (100 mL), sodium borohydride (398 mg) was added at 0° C. The reaction solution was warmed to room temperature and stirred for 2 hours, and thereafter, an ammonium chloride aqueous solution was added thereto, and the mixture was extracted with ethyl acetate. The organic layer was washed with saturated saline, dried over anhydrous sodium sulfate, and then, the solvent was distilled off. The obtained residue was roughly purified by silica gel column chromatography (hexane:ethyl acetate=10:1) and directly used in the subsequent reaction. To a solution of the obtained roughly purified product in DMF (100 mL), phosphorus oxychloride (2.2 g) was added. The reaction solution was heated to 60° C. and stirred for 8 hours. Thereafter, the reaction solution was poured to ice water, and the mixture was stirred for 5 minutes, and then, the organic layer was separated. The organic layer was washed with saturated saline, dried over anhydrous sodium sulfate, and the solvent was distilled off. The obtained residue was purified by silica gel column chromatography (hexane:ethyl acetate=10:1→5:1) to give the title compound (299 mg) having the following physical property values.

$^1$H-NMR (CDCl$_3$): δ 9.57, 7.30-7.24, 6.82-6.78, 3.85, 3.08, 2.65, 0.92.

Example 13: 6-hydroxy-3-methyl-3,4-dihydronaphthalene-2-carbaldehyde

To a solution of the compound (299 mg) prepared in Example 12 in dichloromethane (100 mL), boron tribromide (815 mg) was added dropwise at 0° C. After the mixture was stirred at 0° C. for 3 hours, the reaction solution was poured to ice water, and the mixture was stirred for 5 minutes, and then, the organic layer was separated. The organic layer was washed with saturated saline, dried over anhydrous sodium sulfate, and the solvent was distilled off. The obtained residue was purified by silica gel column chromatography (hexane:ethyl acetate=5:1) to give the title compound (200 mg) having the following physical property values.

$^1$H-NMR (CDCl$_3$): δ 9.57, 7.18, 6.72, 3.08, 2.60, 0.94.

Example 14: (R)-6-hydroxy-3-methyl-3,4-dihydronaphthalene-2-carbaldehyde

The compound prepared in Example 13 was subjected to optical resolution using HPLC (column used: Daicel Corporation CHIRALCEL OJ-H (4.6 mm I. D.×250 mm L), mobile phase: normal hexane:2-propanol=80:20, flow rate: 1 mL/min, temperature: 40° C., wavelength: 245 nm), whereby the title compound was obtained in the first peak (retention time: about 6.9 minutes).

Example 14(1): (S)-6-hydroxy-3-methyl-3,4-dihydronaphthalene-2-carbaldehyde

By the optical resolution in Example 14, the title compound was obtained in the second peak (retention time: about 8.1 minutes).

Example 15: 1-[((3S)-3-methyl-6-pentoxy-3,4-dihydronaphthalen-2-yl)methyl]azetidine-3-carboxylic acid

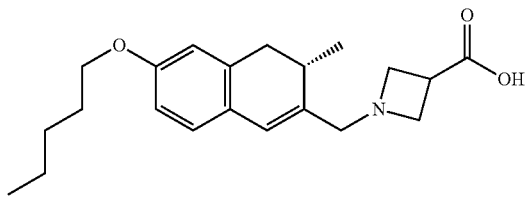 [SMILES: CCCCCOc1ccc2c(c1)C[C@H](C)C(CN1CC(C(=O)O)C1)=C2]

The compound (2.5 g) prepared in Example 14 (1) and methyl azetidine-3-carboxylate hydrochloride (2.6 g) were used and subjected to the same reaction as in Example 5 to give (S)-methyl 1-((6-hydroxy-3-methyl-3,4-dihydronaphthalen-2-yl)methyl)azetidine-3-carboxylate (3.8 g). (S)-methyl 1-((6-hydroxy-3-methyl-3,4-dihydronaphthalen-2-yl)methyl)azetidine-3-carboxylate (30 mg) and 1-pentanol (13.8 mg) were used and subjected to the same reactions as in Example 8→Example 7 to give the title compound (19.5 mg) having the following physical property values.

$^1$H-NMR (DMSO-$d_6$): δ 6.97, 6.71, 6.68, 6.26, 3.92, 3.60-3.00, 2.84, 2.34, 1.68, 1.45-1.26, 0.89, 0.84;
LCMS: Retention time 0.91 minutes.

Examples 15 (1) to (87)

The compound prepared in Example 14 or Example 14 (1), methyl azetidine-3-carboxylate hydrochloride or a corresponding amine derivative instead thereof, and a corresponding alkyl halide instead of 1-bromopentane were used and subjected to the same reactions as in Example 5→Example 6→Example 7, or the compound prepared in Example 14 or Example 14 (1), methyl azetidine-3-carboxylate hydrochloride or a corresponding amine derivative instead thereof, and a corresponding alcohol instead of 1-butanol were used and subjected to the same reactions as in Example 5 Example 8→Example 7 to give the following compounds of Examples.

Example 15 (1): 1-[((3R)-3-methyl-6-pentoxy-3,4-dihydronaphthalen-2-yl)methyl]azetidine-3-carboxylic acid

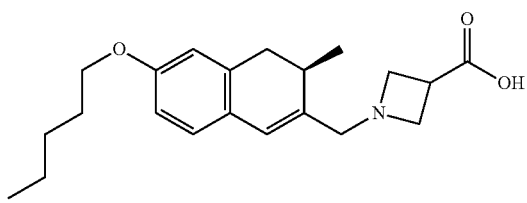 [SMILES: CCCCCOc1ccc2c(c1)C[C@@H](C)C(CN1CC(C(=O)O)C1)=C2]

$^1$H-NMR (DMSO-$d_6$): δ 6.97, 6.71, 6.68, 6.26, 3.92, 3.60-3.00, 2.84, 2.34, 1.68, 1.45-1.26, 0.89, 0.84;
LCMS: Retention time 0.91 minutes.

Example 15 (2): 1-[((3S)-6-hexoxy-3-methyl-3,4-dihydronaphthalen-2-yl)methyl]azetidine-3-carboxylic acid $^1$H-NMR (DMSO-$d_6$): δ 6.96, 6.71, 6.67, 6.22, 3.92, 3.42, 3.21, 2.98, 2.84, 2.33, 1.68, 1.41, 1.31, 0.86;
LCMS: Retention time 0.97 minutes.

Example 15 (3): 1-[((3R)-6-hexoxy-3-methyl-3,4-dihydronaphthalen-2-yl)methyl]azetidine-3-carboxylic acid $^1$H-NMR (DMSO-$d_6$): δ 6.96, 6.71, 6.67, 6.22, 3.92, 3.42, 3.21, 2.98, 2.84, 2.33, 1.68, 1.41, 1.31, 0.86;
LCMS: Retention time 0.97 minutes.

Example 15 (4): 1-[[(3S)-3-methyl-6-(3-methylpentoxy)-3,4-dihydronaphthalen-2-yl]methyl]azetidine-3-carboxylic acid $^1$H-NMR (DMSO-$d_6$): δ 6.97, 6.72, 6.69, 6.25, 3.96, 3.65-3.00, 2.85, 2.34, 1.72, 1.59-1.47, 1.38, 1.18, 0.90, 0.88-0.83;
LCMS: Retention time 0.95 minutes.

Example 15 (5): 1-[[(3R)-3-methyl-6-(3-methylpentoxy)-3,4-dihydronaphthalen-2-yl]methyl]azetidine-3-carboxylic acid $^1$H-NMR (DMSO-$d_6$): δ 6.97, 6.72, 6.69, 6.25, 3.96, 3.65-3.00, 2.85, 2.34, 1.72, 1.59-1.47, 1.38, 1.18, 0.90, 0.88-0.83;
LCMS: Retention time 0.95 minutes.

Example 15 (6): 1-[((3S)-3-methyl-6-propoxy-3,4-dihydronaphthalen-2-yl)methyl]azetidine-3-carboxylic acid $^1$H-NMR (DMSO-$d_6$): δ 6.97, 6.71, 6.68, 6.24, 3.89, 3.60-2.90, 2.84, 2.32, 1.70, 0.96, 0.85;
LCMS: Retention time 0.79 minutes.

Example 15 (7): 1-[((3R)-3-methyl-6-propoxy-3,4-dihydronaphthalen-2-yl)methyl]azetidine-3-carboxylic acid $^1$H-NMR (DMSO-$d_6$): δ 6.97, 6.71, 6.68, 6.24, 3.89, 3.60-2.90, 2.84, 2.32, 1.70, 0.96, 0.85;
LCMS: Retention time 0.79 minutes.

Example 15 (8): 1-[((3S)-6-heptoxy-3-methyl-3,4-dihydronaphthalen-2-yl)methyl]azetidine-3-carboxylic acid $^1$H-NMR (DMSO-$d_6$): δ 6.97, 6.71, 6.68, 6.25, 3.92, 3.60-3.00, 2.84, 2.33, 1.68, 1.39, 1.35-1.20, 0.87, 0.85;
LCMS: Retention time 1.02 minutes.

Example 15 (9): 1-[((3R)-6-heptoxy-3-methyl-3,4-dihydronaphthalen-2-yl)methyl]azetidine-3-carboxylic acid $^1$H-NMR (DMSO-$d_6$): δ 6.97, 6.71, 6.68, 6.25, 3.92, 3.60-3.00, 2.84, 2.33, 1.68, 1.39, 1.35-1.20, 0.87, 0.85;
LCMS: Retention time 1.02 minutes.

Example 15 (10): 1-[[(3S)-3-methyl-6-[(2R)-pentan-2-yl]oxy-3,4-dihydronaphthalen-2-yl]methyl]azetidine-3-carboxylic acid $^1$H-NMR (DMSO-$d_6$): δ 6.95, 6.68, 6.66, 6.22, 4.40, 3.60-2.95, 2.83, 2.32, 1.61, 1.50, 1.45-1.28, 1.20, 0.89, 0.85;
LCMS: Retention time 0.88 minutes.

Example 15 (11): 1-[[(3R)-3-methyl-6-[(2R)-pentan-2-yl]oxy-3,4-dihydronaphthalen-2-yl]methyl]azetidine-3-carboxylic acid $^1$H-NMR (DMSO-d$_6$): δ 6.95, 6.68, 6.66, 6.22, 4.40, 3.60-2.95, 2.83, 2.32, 1.61, 1.50, 1.45-1.28, 1.20, 0.89, 0.85;
LCMS: Retention time 0.88 minutes.

Example 15 (12): 1-[[(3S)-3-methyl-6-[(2S)-pentan-2-yl]oxy-3,4-dihydronaphthalen-2-yl]methyl]azetidine-3-carboxylic acid $^1$H-NMR (CDCl$_3$): δ 6.97, 6.70-6.60, 6.45, 4.46-4.22, 4.15-3.97, 3.92, 3.60-3.30, 3.02, 2.61-2.47, 1.69, 1.59-1.31, 1.28, 0.93;
LCMS: Retention time 0.88 minutes.

Example 15 (13): 1-[[(3R)-3-methyl-6-[(2S)-pentan-2-yl]oxy-3,4-dihydronaphthalen-2-yl]methyl]azetidine-3-carboxylic acid $^1$H-NMR (CDCl$_3$): δ 6.97, 6.70-6.60, 6.45, 4.46-4.22, 4.15-3.97, 3.92, 3.60-3.30, 3.02, 2.61-2.47, 1.69, 1.59-1.31, 1.28, 0.93;
LCMS: Retention time 0.88 minutes.

Example 15 (14): 1-[[(3S)-3-methyl-6-(3-methylbutoxy)-3,4-dihydronaphthalen-2-yl]methyl]azetidine-3-carboxylic acid $^1$H-NMR (DMSO-d$_6$): δ 6.96, 6.72, 6.69, 6.23, 3.96, 3.60-3.00, 2.84, 2.33, 1.77, 1.59, 0.93, 0.85;
LCMS: Retention time 0.91 minutes.

Example 15 (15): 1-[[(3R)-3-methyl-6-(3-methylbutoxy)-3,4-dihydronaphthalen-2-yl]methyl]azetidine-3-carboxylic acid $^1$H-NMR (DMSO-d$_6$): δ 6.96, 6.72, 6.69, 6.23, 3.96, 3.60-3.00, 2.84, 2.33, 1.77, 1.59, 0.93, 0.85;
LCMS: Retention time 0.91 minutes.

Example 15 (16): 1-[((3S)-6-hexan-2-yloxy-3-methyl-3,4-dihydronaphthalen-2-yl)methyl]azetidine-3-carboxylic acid $^1$H-NMR (DMSO-d$_6$): δ 6.95, 6.68, 6.67, 6.23, 4.39, 3.60-2.97, 2.83, 2.33, 1.62, 1.52, 1.43-1.25, 1.20, 0.89-0.83;
LCMS: Retention time 0.94 minutes.

Example 15 (17): 1-[((3R)-6-hexan-2-yloxy-3-methyl-3,4-dihydronaphthalen-2-yl)methyl]azetidine-3-carboxylic acid $^1$H-NMR (DMSO-d$_6$): δ 6.95, 6.68, 6.67, 6.23, 4.39, 3.60-2.97, 2.83, 2.33, 1.62, 1.52, 1.43-1.25, 1.20, 0.89-0.83;
LCMS: Retention time 0.94 minutes.

Example 15 (18): 1-[[(3S)-3-methyl-6-(2-methylpentoxy)-3,4-dihydronaphthalen-2-yl]methyl]azetidine-3-carboxylic acid $^1$H-NMR (DMSO-d$_6$): δ 6.97, 6.72, 6.68, 6.25, 3.80, 3.72, 3.60-2.97, 2.85, 2.34, 1.86, 1.48-1.24, 1.18, 0.96, 0.88, 0.85;
LCMS: Retention time 0.96 minutes.

Example 15 (19): 1-[[(3R)-3-methyl-6-(2-methylpentoxy)-3,4-dihydronaphthalen-2-yl]methyl]azetidine-3-carboxylic acid $^1$H-NMR (DMSO-d$_6$): δ 6.97, 6.72, 6.68, 6.25, 3.80, 3.72, 3.60-2.97, 2.85, 2.34, 1.86, 1.48-1.24, 1.18, 0.96, 0.88, 0.85;
LCMS: Retention time 0.96 minutes.

Example 15 (20): 1-[[(3S)-3-methyl-6-(4-methylpentoxy)-3,4-dihydronaphthalen-2-yl]methyl]azetidine-3-carboxylic acid $^1$H-NMR (DMSO-d$_6$): δ 6.97, 6.71, 6.68, 6.26, 3.92, 3.60-3.01, 2.85, 2.33, 1.69, 1.57, 1.29, 0.89, 0.85;
LCMS: Retention time 0.95 minutes.

Example 15 (21): 1-[[(3R)-3-methyl-6-(4-methylpentoxy)-3,4-dihydronaphthalen-2-yl]methyl]azetidine-3-carboxylic acid $^1$H-NMR (DMSO-d$_6$): δ 6.97, 6.71, 6.68, 6.26, 3.92, 3.60-3.01, 2.85, 2.33, 1.69, 1.57, 1.29, 0.89, 0.85;
LCMS: Retention time 0.95 minutes.

Example 15 (22): 1-[[(3S)-6-(2,2-dimethylpropoxy)-3-methyl-3,4-dihydronaphthalen-2-yl]methyl]azetidine-3-carboxylic acid $^1$H-NMR (DMSO-d$_6$): δ 6.96, 6.72, 6.68, 6.21, 3.59, 3.21, 2.96, 2.84, 2.55, 2.32, 0.99, 0.84;
LCMS: Retention time 0.92 minutes.

Example 15 (23): 1-[[(3R)-6-(2,2-dimethylpropoxy)-3-methyl-3,4-dihydronaphthalen-2-yl]methyl]azetidine-3-carboxylic acid $^1$H-NMR (DMSO-d$_6$): δ 6.96, 6.72, 6.68, 6.21, 3.59, 3.21, 2.96, 2.84, 2.55, 2.32, 0.99, 0.84;
LCMS: Retention time 0.92 minutes.

Example 15 (24): 1-[[(3S)-3-methyl-6-[(2S)-4-methylpentan-2-yl]oxy-3,4-dihydronaphthalen-2-yl]methyl]azetidine-3-carboxylic acid $^1$H-NMR (DMSO-d$_6$): δ 6.96, 6.68, 6.66, 6.22, 4.46, 3.60-2.90, 2.83, 2.33, 1.73, 1.59, 1.33, 1.19, 0.91, 0.88, 0.85;
LCMS: Retention time 0.93 minutes.

Example 15 (25): 1-[[(3R)-3-methyl-6-[(2S)-4-methylpentan-2-yl]oxy-3,4-dihydronaphthalen-2-yl]methyl]azetidine-3-carboxylic acid $^1$H-NMR (DMSO-d$_6$): δ 6.96, 6.68, 6.66, 6.22, 4.46, 3.60-2.90, 2.83, 2.33, 1.73, 1.59, 1.33, 1.19, 0.91, 0.88, 0.85;
LCMS: Retention time 0.93 minutes.

Example 15 (26): 1-[[(3S)-6-(3,3-dimethylbutoxy)-3-methyl-3,4-dihydronaphthalen-2-yl]methyl]azetidine-3-carboxylic acid $^1$H-NMR (DMSO-d$_6$): δ 6.95, 6.71, 6.68, 6.22, 3.98, 3.24, 3.02, 2.84, 2.55, 2.33, 1.63, 0.95, 0.84;
LCMS: Retention time 0.94 minutes.

Example 15 (27): 1-[[(3R)-6-(3,3-dimethylbutoxy)-3-methyl-3,4-dihydronaphthalen-2-yl]methyl]azetidine-3-carboxylic acid $^1$H-NMR (DMSO-d$_6$): δ 6.95, 6.71, 6.68, 6.22, 3.98, 3.24, 3.02, 2.84, 2.55, 2.33, 1.63, 0.95, 0.84;
LCMS: Retention time 0.94 minutes.

Example 15 (28): 1-[[(3S)-3-methyl-6-[(2R)-4-methylpentan-2-yl]oxy-3,4-dihydronaphthalen-2-yl]methyl]azetidine-3-carboxylic acid $^1$H-NMR (DMSO-$d_6$): δ 6.96, 6.69, 6.67, 6.22, 4.46, 3.60-2.90, 2.84, 2.33, 1.73, 1.59, 1.34, 1.20, 0.91, 0.88, 0.85; LCMS: Retention time 0.93 minutes.

Example 15 (29): 1-[[(3R)-3-methyl-6-[(2R)-4-methylpentan-2-yl]oxy-3,4-dihydronaphthalen-2-yl]methyl]azetidine-3-carboxylic acid $^1$H-NMR (DMSO-$d_6$): δ 6.96, 6.69, 6.67, 6.22, 4.46, 3.60-2.90, 2.84, 2.33, 1.73, 1.59, 1.34, 1.20, 0.91, 0.88, 0.85; LCMS: Retention time 0.93 minutes.

Example 15 (30): 1-[((3S)-6-hexan-3-yloxy-3-methyl-3,4-dihydronaphthalen-2-yl)methyl]azetidine-3-carboxylic acid $^1$H-NMR (DMSO-$d_6$): δ 6.95, 6.69, 6.67, 6.23, 4.24, 3.60-2.90, 2.84, 2.33, 1.56, 1.34, 0.88; LCMS: Retention time 0.94 minutes.

Example 15 (31): 1-[((3R)-6-hexan-3-yloxy-3-methyl-3,4-dihydronaphthalen-2-yl)methyl]azetidine-3-carboxylic acid $^1$H-NMR (DMSO-$d_6$): δ 6.95, 6.69, 6.67, 6.23, 4.24, 3.60-2.90, 2.84, 2.33, 1.56, 1.34, 0.88; LCMS: Retention time 0.94 minutes.

Example 15 (32): 1-[[(3S)-3-methyl-6-(2-methylhexan-3-yloxy)-3,4-dihydronaphthalen-2-yl]methyl]azetidine-3-carboxylic acid $^1$H-NMR (DMSO-$d_6$): δ 6.93, 6.69, 6.68, 6.21, 4.12, 3.60-2.90, 2.83, 2.32, 1.91, 1.51, 1.39, 1.29, 0.91, 0.88, 0.86; LCMS: Retention time 0.98 minutes.

Example 15 (33): 1-[[(3R)-3-methyl-6-(2-methylhexan-3-yloxy)-3,4-dihydronaphthalen-2-yl]methyl]azetidine-3-carboxylic acid $^1$H-NMR (DMSO-$d_6$): δ 6.93, 6.69, 6.68, 6.21, 4.12, 3.60-2.90, 2.83, 2.32, 1.91, 1.51, 1.39, 1.29, 0.91, 0.88, 0.86; LCMS: Retention time 0.98 minutes.

Example 15 (34): 1-[[(3S)-3-methyl-6-(4,4,4-trifluorobutoxy)-3,4-dihydronaphthalen-2-yl]methyl]azetidine-3-carboxylic acid

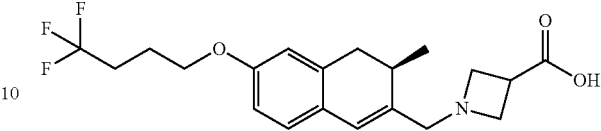

$^1$H-NMR (DMSO-$d_6$): δ 6.95, 6.71, 6.68, 6.20, 3.98, 3.46-3.36, 3.24-3.12, 2.96, 2.82, 2.49, 2.39, 2.31, 1.89, 0.83; LCMS: Retention time 0.85 minutes.

Example 15 (35): 1-[[(3R)-3-methyl-6-(4,4,4-trifluorobutoxy)-3,4-dihydronaphthalen-2-yl]methyl]azetidine-3-carboxylic acid $^1$H-NMR (DMSO-$d_6$): δ 6.95, 6.71, 6.68, 6.20, 3.98, 3.46-3.36, 3.24-3.12, 2.96, 2.82, 2.49, 2.39, 2.31, 1.89, 0.83; LCMS: Retention time 0.85 minutes.

Example 15 (36): 1-[[(3S)-6-[(E)-but-2-enoxy]-3-methyl-3,4-dihydronaphthalen-2-yl]methyl]azetidine-3-carboxylic acid $^1$H-NMR (DMSO-$d_6$): δ 6.96, 6.71, 6.68, 6.23, 5.82, 5.68, 4.44, 3.90-2.95, 2.84, 2.33, 1.70, 0.85; LCMS: Retention time 0.82 minutes.

Example 15 (37): 1-[[(3R)-6-[(E)-but-2-enoxy]-3-methyl-3,4-dihydronaphthalen-2-yl]methyl]azetidine-3-carboxylic acid $^1$H-NMR (DMSO-$d_6$): δ 6.96, 6.71, 6.68, 6.23, 5.82, 5.68, 4.44, 3.90-2.95, 2.84, 2.33, 1.70, 0.85; LCMS: Retention time 0.82 minutes.

Example 15 (38): 1-[[(3S)-3-methyl-6-(3-methylbut-2-enoxy)-3,4-dihydronaphthalen-2-yl]methyl]azetidine-3-carboxylic acid $^1$H-NMR (DMSO-$d_6$): δ 6.96, 6.72, 6.68, 6.23, 5.41, 4.48, 3.80-2.95, 2.84, 2.33, 1.74, 1.70, 0.85; LCMS: Retention time 0.85 minutes.

Example 15 (39): 1-[[(3R)-3-methyl-6-(3-methylbut-2-enoxy)-3,4-dihydronaphthalen-2-yl]methyl]azetidine-3-carboxylic acid $^1$H-NMR (DMSO-$d_6$): δ 6.96, 6.72, 6.68, 6.23, 5.41, 4.48, 3.80-2.95, 2.84, 2.33, 1.74, 1.70, 0.85; LCMS: Retention time 0.85 minutes.

Example 15 (40): 1-[[(3S)-3-methyl-6-(3,4,4-trifluorobut-3-enoxy)-3,4-dihydronaphthalen-2-yl]methyl]azetidine-3-carboxylic acid $^1$H-NMR (DMSO-$d_6$): δ 6.99, 6.74, 6.71, 6.24, 4.13, 3.75-2.95, 2.84, 2.78, 2.33, 0.84; LCMS: Retention time 0.83 minutes.

Example 15 (41): 1-[[(3R)-3-methyl-6-(3,4,4-trifluorobut-3-enoxy)-3,4-dihydronaphthalen-2-yl]methyl]azetidine-3-carboxylic acid $^1$H-NMR (DMSO-$d_6$): δ 6.99, 6.74, 6.71, 6.24, 4.13, 3.75-2.95, 2.84, 2.78, 2.33, 0.84; LCMS: Retention time 0.83 minutes.

Example 15 (42): 1-[((3S)-6-butoxy-3-methyl-3,4-dihydronaphthalen-2-yl)methyl]-3-fluoroazetidine-3-carboxylic acid $^1$H-NMR (DMSO-$d_6$): δ 6.99, 6.72, 6.65, 6.31, 3.93, 3.85-3.05, 2.87, 2.37, 1.68, 1.48, 0.92, 0.85;
LCMS: Retention time 0.84 minutes.

Example 15 (43): 1-[((3R)-6-butoxy-3-methyl-3,4-dihydronaphthalen-2-yl)methyl]-3-fluoroazetidine-3-carboxylic acid $^1$H-NMR (DMSO-$d_6$): δ 6.99, 6.72, 6.65, 6.31, 3.93, 3.85-3.05, 2.87, 2.37, 1.68, 1.48, 0.92, 0.85;
LCMS: Retention time 0.84 minutes.

Example 15 (44): 3-fluoro-1-[[(3S)-3-methyl-6-(4,4,4-trifluorobutoxy)-3,4-dihydronaphthalen-2-yl]methyl]azetidine-3-carboxylic acid $^1$H-NMR (DMSO-$d_6$): δ 7.01, 6.74, 6.71, 6.31, 4.01, 3.94-3.01, 2.87, 2.40, 1.92, 0.85;
LCMS: Retention time 0.83 minutes.

Example 15 (45): 3-fluoro-1-[[(3R)-3-methyl-6-(4,4,4-trifluorobutoxy)-3,4-dihydronaphthalen-2-yl]methyl]azetidine-3-carboxylic acid $^1$H-NMR (DMSO-$d_6$): δ 7.01, 6.74, 6.71, 6.31, 4.01, 3.94-3.01, 2.87, 2.40, 1.92, 0.85;
LCMS: Retention time 0.83 minutes.

Example 15 (46): 1-[[(3S)-6-[(E)-but-2-enoxy]-3-methyl-3,4-dihydronaphthalen-2-yl]methyl]-3-fluoroazetidine-3-carboxylic acid $^1$H-NMR (DMSO-$d_6$): δ 6.99, 6.72, 6.69, 6.29, 5.83, 5.68, 4.44, 3.85-3.00, 2.87, 2.40-2.34, 1.70, 0.86;
LCMS: Retention time 0.79 minutes.

Example 15 (47): 1-[[(3R)-6-[(E)-but-2-enoxy]-3-methyl-3,4-dihydronaphthalen-2-yl]methyl]-3-fluoroazetidine-3-carboxylic acid $^1$H-NMR (DMSO-$d_6$): δ 6.99, 6.72, 6.69, 6.29, 5.83, 5.68, 4.44, 3.85-3.00, 2.87, 2.40-2.34, 1.70, 0.86;
LCMS: Retention time 0.79 minutes.

Example 15 (48): 1-[((3S)-6-but-2-ynoxy-3-methyl-3,4-dihydronaphthalen-2-yl)methyl]-3-fluoroazetidine-3-carboxylic acid $^1$H-NMR (DMSO-$d_6$): δ 7.01, 6.76-6.71, 6.30, 4.70, 3.84-2.98, 2.87, 2.42-2.34, 1.83, 0.86;
LCMS: Retention time 0.74 minutes.

Example 15 (49): 1-[((3R)-6-but-2-ynoxy-3-methyl-3,4-dihydronaphthalen-2-yl)methyl]-3-fluoroazetidine-3-carboxylic acid $^1$H-NMR (DMSO-$d_6$): δ 7.01, 6.76-6.71, 6.30, 4.70, 3.84-2.98, 2.87, 2.42-2.34, 1.83, 0.86;
LCMS: Retention time 0.74 minutes.

Example 15 (50): 3-fluoro-1-[[(3S)-3-methyl-6-(3-methylbut-2-enoxy)-3,4-dihydronaphthalen-2-yl]methyl]azetidine-3-carboxylic acid $^1$H-NMR (DMSO-d6): δ 6.99, 6.73, 6.69, 6.29, 5.41, 4.49, 3.85-3.04, 2.87, 2.41-2.34, 1.74, 1.70, 0.86;
LCMS: Retention time 0.84 minutes.

Example 15 (51): 3-fluoro-1-[[(3R)-3-methyl-6-(3-methylbut-2-enoxy)-3,4-dihydronaphthalen-2-yl]methyl]azetidine-3-carboxylic acid $^1$H-NMR (DMSO-$d_6$): δ 6.99, 6.73, 6.69, 6.29, 5.41, 4.49, 3.85-3.04, 2.87, 2.41-2.34, 1.74, 1.70, 0.86;
LCMS: Retention time 0.84 minutes.

Example 15 (52): 3-fluoro-1-[[(3S)-3-methyl-6-(3,4,4-trifluorobut-3-enoxy)-3,4-dihydronaphthalen-2-yl]methyl]azetidine-3-carboxylic acid

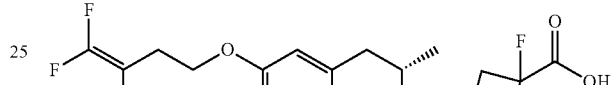

$^1$H-NMR (DMSO-$d_6$): δ 7.01, 6.75, 6.72, 6.29, 4.13, 3.82-3.08, 2.87, 2.78, 2.41-2.34, 0.85;
LCMS: Retention time 0.81 minutes.

Example 15 (53): 3-fluoro-1-[[(3R)-3-methyl-6-(3,4,4-trifluorobut-3-enoxy)-3,4-dihydronaphthalen-2-yl]methyl]azetidine-3-carboxylic acid

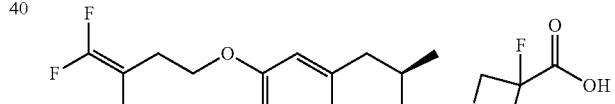

$^1$H-NMR (DMSO-$d_6$): δ 7.01, 6.75, 6.72, 6.29, 4.13, 3.82-3.08, 2.87, 2.78, 2.41-2.34, 0.85;
LCMS: Retention time 0.81 minutes.

Example 15 (54): 3-fluoro-1-[[(3S)-3-methyl-6-[(2S)-pentan-2-yl]oxy-3,4-dihydronaphthalen-2-yl]methyl]azetidine-3-carboxylic acid $^1$H-NMR (DMSO-$d_6$): δ 6.98, 6.69, 6.67, 6.29, 4.41, 3.85-2.98, 2.86, 2.41-2.34, 1.61, 1.49, 1.44-1.31, 1.20, 0.89, 0.86;
LCMS: Retention time 0.87 minutes.

Example 15 (55): 3-fluoro-1-[[(3R)-3-methyl-6-[(2S)-pentan-2-yl]oxy-3,4-dihydronaphthalen-2-yl]methyl]azetidine-3-carboxylic acid $^1$H-NMR (DMSO-$d_6$): δ 6.98, 6.69, 6.67, 6.29, 4.41, 3.85-2.98, 2.86, 2.41-2.34, 1.61, 1.49, 1.44-1.31, 1.20, 0.89, 0.86;
LCMS: Retention time 0.87 minutes.

Example 15 (56): 1-[((3S)-6-ethoxy-3-methyl-3,4-dihydronaphthalen-2-yl)methyl]-3-fluoroazetidine-3-carboxylic acid $^1$H-NMR (DMSO-d$_6$): δ 6.98, 6.71, 6.68, 6.29, 3.99, 3.60-2.97, 2.87, 2.38, 1.30, 0.86;
LCMS: Retention time 0.71 minutes.

Example 15 (57): 1-[((3R)-6-ethoxy-3-methyl-3,4-dihydronaphthalen-2-yl)methyl]-3-fluoroazetidine-3-carboxylic acid $^1$H-NMR (DMSO-d$_6$): δ 6.98, 6.71, 6.68, 6.29, 3.99, 3.60-2.97, 2.87, 2.38, 1.30, 0.86;
LCMS: Retention time 0.71 minutes.

Example 15 (58): 3-fluoro-1-[((3S)-3-methyl-6-propoxy-3,4-dihydronaphthalen-2-yl)methyl]azetidine-3-carboxylic acid $^1$H-NMR (DMSO-d$_6$): δ 6.99, 6.72, 6.69, 6.31, 3.89, 3.60-3.00, 2.87, 2.38, 1.70, 0.96, 0.86;
LCMS: Retention time 0.78 minutes.

Example 15 (59): 3-fluoro-1-[((3R)-3-methyl-6-propoxy-3,4-dihydronaphthalen-2-yl)methyl]azetidine-3-carboxylic acid $^1$H-NMR (DMSO-d$_6$): δ 6.99, 6.72, 6.69, 6.31, 3.89, 3.60-3.00, 2.87, 2.38, 1.70, 0.96, 0.86;
LCMS: Retention time 0.78 minutes.

Example 15 (60): 3-fluoro-1-[((3S)-3-methyl-6-propoxy-3,4-dihydronaphthalen-2-yl)methyl]pyrrolidine-3-carboxylic acid $^1$H-NMR (DMSO-d$_6$): δ 6.96, 6.72, 6.68, 6.29, 3.90, 3.70-3.10, 2.89, 2.36, 2.10, 1.70, 0.97, 0.88;
LCMS: Retention time 0.80 minutes.

Example 15 (61): 3-fluoro-1-[((3R)-3-methyl-6-propoxy-3,4-dihydronaphthalen-2-yl)methyl]pyrrolidine-3-carboxylic acid $^1$H-NMR (DMSO-d$_6$): δ 6.96, 6.72, 6.68, 6.29, 3.90, 3.70-3.10, 2.89, 2.36, 2.10, 1.70, 0.97, 0.88;
LCMS: Retention time 0.80 minutes.

Example 15 (62): 1-[[(3S)-3-methyl-6-[(2R)-2-methylbutoxy]-3,4-dihydronaphthalen-2-yl]methyl]azetidine-3-carboxylic acid $^1$H-NMR (DMSO-d$_6$): δ 7.03, 6.75, 6.73, 6.41, 3.81, 3.74, 3.10, 2.89, 1.81-1.75, 1.62-1.56, 1.53-1.47, 1.43-1.38, 1.37-1.33, 1.28-1.20, 1.18, 0.96, 0.90, 0.85;
LCMS: Retention time 0.93 minutes.

Example 15 (63): 1-[[(3R)-3-methyl-6-[(2R)-2-methylbutoxy]-3,4-dihydronaphthalen-2-yl]methyl]azetidine-3-carboxylic acid $^1$H-NMR (DMSO-d$_6$): δ 7.03, 6.76, 6.73, 6.42, 3.82, 3.73, 3.09, 2.89, 2.55, 1.82-1.75, 1.62-1.57, 1.52-1.47, 1.45-1.33, 1.26-1.19, 1.18, 0.96, 0.90, 0.88, 0.85;
LCMS: Retention time 0.92 minutes.

Example 15 (64): 1-[[(3S)-3-methyl-6-[(2S)-2-methylbutoxy]-3,4-dihydronaphthalen-2-yl]methyl]azetidine-3-carboxylic acid $^1$H-NMR (DMSO-d$_6$): δ 7.03, 6.76, 6.73, 6.42, 3.82, 3.73, 3.09, 2.89, 2.55, 1.82-1.75, 1.62-1.57, 1.52-1.47, 1.45-1.33, 1.26-1.19, 1.18, 0.96, 0.90, 0.88, 0.85;
LCMS: Retention time 0.92 minutes.

Example 15 (65): 1-[[(3R)-3-methyl-6-[(2S)-2-methylbutoxy]-3,4-dihydronaphthalen-2-yl]methyl]azetidine-3-carboxylic acid $^1$H-NMR (DMSO-d$_6$): δ 7.03, 6.75, 6.73, 6.41, 3.81, 3.74, 3.10, 2.89, 1.81-1.75, 1.62-1.56, 1.53-1.47, 1.43-1.38, 1.37-1.33, 1.28-1.20, 1.18, 0.96, 0.90, 0.85;
LCMS: Retention time 0.93 minutes.

Example 15 (66): 3-fluoro-1-[[(3S)-3-methyl-6-(2-methylpropoxy)-3,4-dihydronaphthalen-2-yl]methyl]azetidine-3-carboxylic acid $^1$H-NMR (DMSO-d$_6$): δ 7.00, 6.73, 6.69, 6.29, 3.71, 3.10, 2.88, 2.02-1.95, 1.18, 0.97, 0.85;
LCMS: Retention time 0.84 minutes.

Example 15 (67): 3-fluoro-1-[[(3R)-3-methyl-6-(2-methylpropoxy)-3,4-dihydronaphthalen-2-yl]methyl]azetidine-3-carboxylic acid $^1$H-NMR (DMSO-d$_6$): δ 7.00, 6.73, 6.69, 6.29, 3.71, 3.10, 2.88, 2.02-1.95, 1.18, 0.97, 0.85;
LCMS: Retention time 0.84 minutes.

Example 15 (68): 1-[[(3S)-3-methyl-6-(2-methylpropoxy)-3,4-dihydronaphthalen-2-yl]methyl]azetidine-3-carboxylic acid $^1$H-NMR (DMSO-d$_6$): δ 7.04, 6.75, 6.72, 6.43, 3.72, 3.09, 2.89, 2.54, 2.03-1.95, 1.18, 0.96, 0.85;
LCMS: Retention time 0.86 minutes.

Example 15 (69): 1-[[(3R)-3-methyl-6-(2-methylpropoxy)-3,4-dihydronaphthalen-2-yl]methyl]azetidine-3-carboxylic acid $^1$H-NMR (DMSO-d$_6$): δ 7.04, 6.75, 6.72, 6.43, 3.72, 3.09, 2.89, 2.54, 2.03-1.95, 1.18, 0.96, 0.85;
LCMS: Retention time 0.86 minutes.

Example 15 (70): 1-[[(3S)-3-methyl-6-(1,1,2,2,3,3,4,4,4-nonadeuteriobutoxy)-3,4-dihydronaphthalen-2-yl]methyl]azetidine-3-carboxylic acid

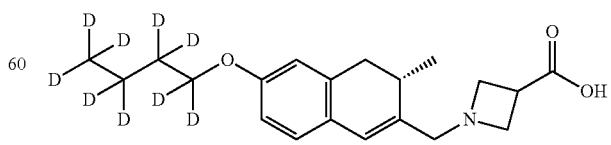

$^1$H-NMR (CD$_3$OD): δ 6.97, 6.72-6.65, 6.37, 3.94, 3.87, 3.71, 3.62, 3.45, 3.38-3.29, 2.98, 2.59, 2.37, 0.92;
LCMS: Retention time 0.85 minutes.

Example 15 (71): 1-[[(3R)-3-methyl-6-(1,1,2,2,3,3,4,4,4-nonadeuteriobutoxy)-3,4-dihydronaphthalen-2-yl]methyl]azetidine-3-carboxylic acid

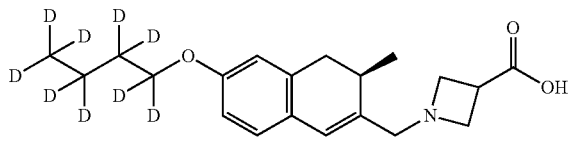 [SMILES: [2H]C([2H])([2H])C([2H])([2H])C([2H])([2H])C([2H])([2H])Oc1ccc2c(c1)C[C@@H](C)C(CN1CC(C(=O)O)C1)=C2]

$^1$H-NMR (CD$_3$OD): δ 6.97, 6.72-6.65, 6.37, 3.94, 3.87, 3.71, 3.62, 3.45, 3.38-3.29, 2.98, 2.59, 2.37, 0.92;
LCMS: Retention time 0.85 minutes.

Example 15 (72): (3R)-1-[[(3S)-3-methyl-6-(4,4,4-trifluorobutoxy)-3,4-dihydronaphthalen-2-yl]methyl]pyrrolidine-3-carboxylic acid

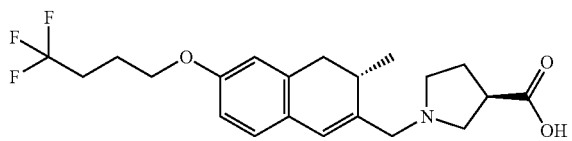 [SMILES: C[C@H]1Cc2cc(OCCCC(F)(F)F)ccc2C=C1CN1CC[C@@H](C(=O)O)C1]

$^1$H-NMR (DMSO-d$_6$) δ 6.97, 6.75, 6.70, 6.28, 4.01, 3.60-3.10, 3.00-2.80, 2.60-2.35, 2.05-1.85, 0.86;
LCMS: Retention time 0.84 minutes.

Example 15 (73): (3R)-1-[[(3R)-3-methyl-6-(4,4,4-trifluorobutoxy)-3,4-dihydronaphthalen-2-yl]methyl]pyrrolidine-3-carboxylic acid

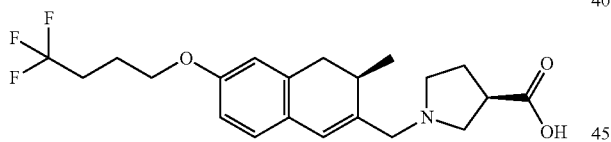

$^1$H-NMR (DMSO-d$_6$) δ 6.97, 6.75, 6.70, 6.28, 4.01, 3.60-3.10, 3.00-2.80, 2.60-2.35, 2.05-1.85, 0.86;
LCMS: Retention time 0.84 minutes.

Example 15 (74): (3S)-3-fluoro-1-[[(3S)-3-methyl-6-(4,4,4-trifluorobutoxy)-3,4-dihydronaphthalen-2-yl]methyl]pyrrolidine-3-carboxylic acid $^1$H-NMR (DMSO-d$_6$): δ 6.97, 6.75, 6.70, 6.31, 4.01, 3.65-2.80, 2.60-2.30, 2.20-2.03, 1.91, 0.88;
LCMS: Retention time 0.84 minutes.

Example 15 (75): (3S)-3-fluoro-1-[[(3R)-3-methyl-6-(4,4,4-trifluorobutoxy)-3,4-dihydronaphthalen-2-yl]methyl]pyrrolidine-3-carboxylic acid $^1$H-NMR (DMSO-d$_6$): δ 6.97, 6.75, 6.70, 6.31, 4.01, 3.65-2.80, 2.60-2.30, 2.20-2.03, 1.91, 0.88;
LCMS: Retention time 0.84 minutes.

Example 15 (76): 1-[[(3S)-3-methyl-6-[(E)-4,4,4-trifluorobut-2-enoxy]-3,4-dihydronaphthalen-2-yl]methyl]azetidine-3-carboxylic acid $^1$H-NMR (DMSO-d$_6$): δ 7.00, 6.79, 6.75-6.70, 6.27-6.20, 4.72, 3.60-3.24, 2.86, 2.33, 0.85;
LCMS: Retention time 0.84 minutes.

Example 15 (77): 1-[[(3R)-3-methyl-6-[(E)-4,4,4-trifluorobut-2-enoxy]-3,4-dihydronaphthalen-2-yl]methyl]azetidine-3-carboxylic acid $^1$H-NMR (DMSO-d$_6$): δ 7.00, 6.79, 6.75-6.70, 6.27-6.20, 4.72, 3.60-3.24, 2.86, 2.33, 0.85;
LCMS: Retention time 0.84 minutes.

Example 15 (78): 1-[[(3S)-3-methyl-6-[(Z)-4,4,4-trifluorobut-2-enoxy]-3,4-dihydronaphthalen-2-yl]methyl]azetidine-3-carboxylic acid $^1$H-NMR (DMSO-d$_6$): δ 7.00, 6.79, 6.76-6.70, 6.25-6.21, 4.72, 2.86, 2.52, 2.35, 0.85;
LCMS: Retention time 0.85 minutes.

Example 15 (79): 1-[[(3R)-3-methyl-6-[(Z)-4,4,4-trifluorobut-2-enoxy]-3,4-dihydronaphthalen-2-yl]methyl]azetidine-3-carboxylic acid $^1$H-NMR (DMSO-d$_6$): δ 7.00, 6.79, 6.76-6.70, 6.25-6.21, 4.72, 2.86, 2.52, 2.35, 0.85;
LCMS: Retention time 0.85 minutes.

Example 15 (80): 3-Fluoro-1-[[(3S)-6-(4-Methoxybutan-2-Yloxy)-3-Methyl-3,4-Dihydronaphthalen-2-Yl]Methyl]Azetidine-3-Carboxylic Acid $^1$H-NMR (DMSO-d$_6$): δ 6.98, 6.70, 6.67, 6.29, 4.60, 3.81-3.67, 3.21, 2.86, 2.87, 1.88-1.83, 1.80-1.73, 1.23, 0.87;
LCMS: Retention time 0.78 minutes.

Example 15 (81): 3-Fluoro-1-[[(3R)-6-(4-Methoxybutan-2-Yloxy)-3-Methyl-3,4-Dihydronaphthalen-2-Yl]Methyl]Azetidine-3-Carboxylic Acid $^1$H-NMR (DMSO-d$_6$): δ 6.98, 6.70, 6.67, 6.29, 4.60, 3.81-3.67, 3.21, 2.86, 2.87, 1.88-1.83, 1.80-1.73, 1.23, 0.87;
LCMS: Retention time 0.78 minutes.

Example 15 (82): 3-Fluoro-1-[[(3S)-3-Methyl-6-[(E)-4,4,4-Trifluorobut-2-Enoxy]-3,4-Dihydronaphthalen-2-Yl]Methyl]Azetidine-3-Carboxylic Acid

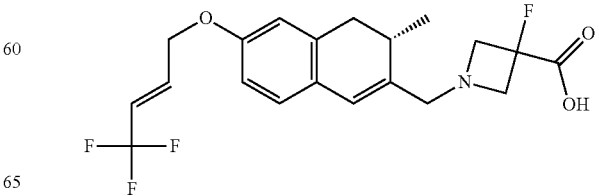

¹H-NMR (DMSO-d₆): δ 7.03, 6.80, 6.75, 6.71, 6.30, 6.25-6.20, 4.73, 2.89, 2.55, 2.52. 2.39, 0.87;
LCMS: Retention time 0.83 minutes.

Example 15 (83): 3-Fluoro-1-[[(3R)-3-Methyl-6-[(E)-4,4,4-Trifluorobut-2-Enoxy]-3,4-Dihydronaphthalen-2-Yl]Methyl]Azetidine-3-Carboxylic Acid

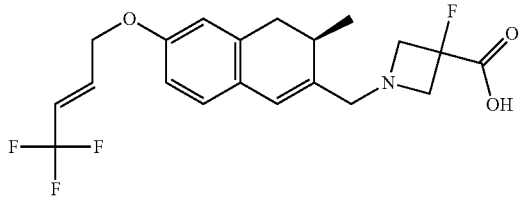 [SMILES: C[C@@H]1Cc2cc(OC/C=C/C(F)(F)F)ccc2C=C1CN1CC(F)(C(=O)O)C1]

¹H-NMR (DMSO-d₆): δ 7.03, 6.80, 6.75, 6.71, 6.30, 6.25-6.20, 4.73, 2.89, 2.55, 2.52. 2.39, 0.87;
LCMS: Retention time 0.83 minutes.

Example 15 (84): 3-Fluoro-1-[[(3S)-3-Methyl-6-[(Z)-4,4,4-Trifluorobut-2-Enoxy]-3,4-Dihydronaphthalen-2-Yl]Methyl]Azetidine-3-Carboxylic Acid ¹H-NMR (DMSO-d₆): δ 7.04, 6.80, 6.76, 6.71, 6.32, 6.26-6.16, 4.72, 2.90, 0.85;
LCMS: Retention time 0.83 minutes.

Example 15 (85): 3-fluoro-1-[[(3R)-3-methyl-6-[(Z)-4,4,4-trifluorobut-2-enoxy]-3,4-dihydronaphthalen-2-yl]methyl]azetidine-3-carboxylic acid ¹H-NMR (DMSO-d₆): δ 7.04, 6.80, 6.76, 6.71, 6.32, 6.26-6.16, 4.72, 2.90, 0.85;
LCMS: Retention time 0.83 minutes.

Example 15 (86): 3-fluoro-1-{[(3S)-3-methyl-6-(3,3,3-trifluoropropoxy)-3,4-dihydro-2-naphthalenyl]methyl}-3-azetidinecarboxylic acid

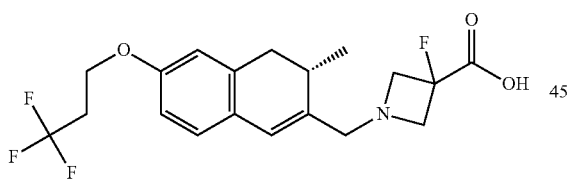

¹H-NMR (DMSO-d₆): δ 7.05, 6.79, 6.75, 6.41, 4.19, 3.50-3.10, 2.91, 2.77, 2.60-2.53, 2.52, 2.45-2.36, 0.86;
LCMS: Retention time 0.78 minutes.

Example 15 (87): 3-fluoro-1-{[(3R)-3-methyl-6-(3,3,3-trifluoropropoxy)-3,4-dihydro-2-naphthalenyl]methyl}-3-azetidinecarboxylic acid

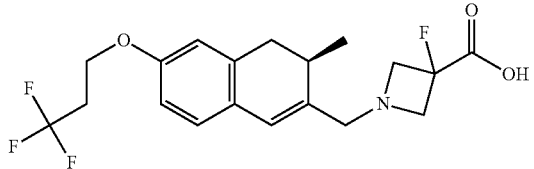 [SMILES: C[C@@H]1Cc2cc(OCCC(F)(F)F)ccc2C=C1CN1CC(F)(C(=O)O)C1]

¹H-NMR (DMSO-d₆): δ 7.05, 6.79, 6.75, 6.41, 4.19, 3.50-3.10, 2.91, 2.77, 2.60-2.53, 2.52, 2.45-2.36, 0.86;
LCMS: Retention time 0.78 minutes.

Example 16: methyl 1-(((3S)-3-methyl-6-(3,3,3-trifluoro-2-methylpropoxy)-3,4-dihydronaphthalen-2-yl)methyl)azetidine-3-carboxylate The compound (2.5 g) prepared in Example 14 (1) and methyl azetidine-3-carboxylate hydrochloride (2.6 g) were used and subjected to the same reaction as in Example 5 to give (S)-methyl 14(6-hydroxy-3-methyl-3,4-dihydronaphthalen-2-yl)methyl)azetidine-3-carboxylate (3.8 g). (S)-methyl 1-((6-hydroxy-3-methyl-3,4-dihydronaphthalen-2-yl)methyl)azetidine-3-carboxylate (50 mg) and 3,3,3-trifluoro-2-methyl-propan-1-ol (31.7 mg) were used and subjected to the same reaction as in Example 8 to give the title compound (18.0 mg).

Example 17: methyl 1-(((S)-3-methyl-6-((R)-3,3,3-trifluoro-2-methylpropoxy)-3,4-dihydronaphthalen-2-yl)methyl)azetidine-3-carboxylate and methyl 1-(((S)-3-methyl-6-((S)-3,3,3-trifluoro-2-methyl-propoxy)-3,4-dihydronaphthalene-2-yl)methyl)azetidine-3-carboxylate The compound prepared in Example 16 was subjected to optical resolution using SFC (column used: Daicel Corporation CHIRALPAK IC (10 mm×250 mm), mobile phase: CO₂:(0.1% DEA/EA/IPA)=9:1, flow rate: 30 mL/min, pressure: 100 bar, wavelength: 254 nm, column temperature: 35° C.). Under the above-mentioned optical resolution conditions, the optically active substances of the compound prepared in Example 16 were obtained in the first peak (retention time: about 9.00 minutes) and in the second peak (retention time: about 12.16 minutes), respectively.

Example 18: 1-[[(3S)-3-methyl-6-((R)-3,3,3-trifluoro-2-methylpropoxy)-3,4-dihydronaphthalen-2-yl]methyl]azetidine-3-carboxylic acid and 1-[[(3S)-3-methyl-6-((S)-3,3,3-trifluoro-2-methylpropoxy)-3,4-dihydronaphthalen-2-yl]methyl]azetidine-3-carboxylic acid

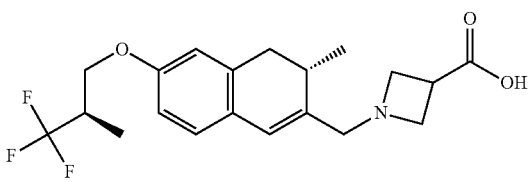

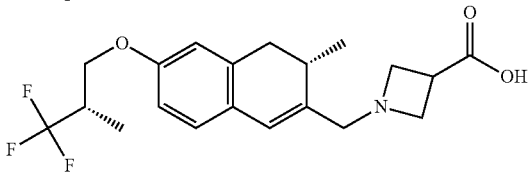

Each of the first peak compound (5.0 mg) or the second peak compound (6.0 mg) obtained by optical resolution in Example 17 was subjected to the same reaction as in Example 7 to give the title compounds (obtained from the first peak: 4.2 mg, obtained from the second peak: 4.7 mg) having the following physical property values.

Obtained from the First Peak $^1$H-NMR (DMSO-$d_6$): δ 7.03, 6.75, 6.73, 6.41, 3.80, 3.75, 3.40, 3.10, 2.89, 2.62, 2.57-2.46, 2.42-2.36, 1.80-1.75, 1.62-1.57, 1.53-1.47, 1.43-1.38, 1.38-1.33, 1.25-1.20, 1.18, 0.96, 0.90, 0.85;

LCMS: Retention time 0.84 minutes.

Obtained from the Second Peak $^1$H-NMR (DMSO-$d_6$): δ 6.99, 6.75, 6.71, 6.22, 6.10, 4.02, 3.23-3.12, 2.95, 2.91-2.87, 2.85, 2.33, 1.19, 0.85;

LCMS: Retention time 0.85 minutes.

Example 18 (1): 1-[[(3R)-3-methyl-6-((R)-3,3,3-trifluoro-2-methylpropoxy)-3,4-dihydronaphthalen-2-yl]methyl]azetidine-3-carboxylic acid and 1-[[(3R)-3-methyl-6-((S)-3,3,3-trifluoro-2-methylpropoxy)-3,4-dihydronaphthalen-2-yl]methyl]azetidine-3-carboxylic acid The compound prepared in Example 14, methyl azetidine-3-carboxylate hydrochloride, and 3,3,3-trifluoro-2-methylpropan-1-ol were used and subjected to the same reactions as in Example 5→Example 8→Example 17→Example 7 to give the title compound having the following physical property values.

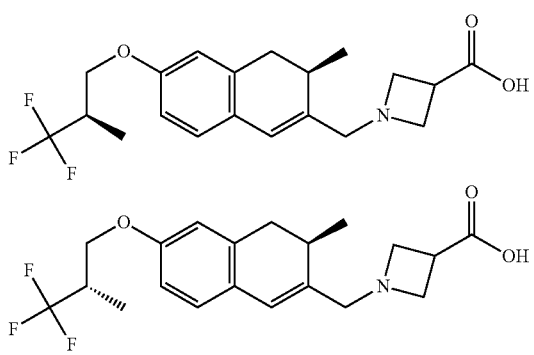

$^1$H-NMR (DMSO-$d_6$): δ 7.03, 6.75, 6.73, 6.41, 3.80, 3.75, 3.40, 3.10, 2.89, 2.62, 2.57-2.46, 2.42-2.36, 1.80-1.75, 1.62-1.57, 1.53-1.47, 1.43-1.38, 1.38-1.33, 1.25-1.20, 1.18, 0.96, 0.90, 0.85;

LCMS: Retention time 0.84 minutes.

or $^1$H-NMR (DMSO-$d_6$): δ 6.99, 6.75, 6.71, 6.22, 6.10, 4.02, 3.23-3.12, 2.95, 2.91-2.87, 2.85, 2.33, 1.19, 0.85;

LCMS: Retention time 0.85 minutes.

Example 19: methyl 1-[(6-butoxy-3-methyl-3,4-dihydronaphthalen-2-yl)methyl]azetidine-3-carboxylate The compound (250 mg) prepared in Example 13 and methyl azetidine-3-carboxylate hydrochloride (242 mg) were used and subjected to the same reaction as in Example 5 to give a corresponding ester derivative. The obtained ester derivative (100 mg) and 1-butanol (39 mg) were used and subjected to the same reaction as in Example 8 to give the title compound (120 mg).

Example 20: (R)-methyl 1-((6-butoxy-3-methyl-3,4-dihydronaphthalen-2-yl)methyl)azetidine-3-carboxylate and (S)-methyl 1-((6-butoxy-3-methyl-3,4-dihydronaphthalen-2-yl)methyl)azetidine-3-carboxylate The compound prepared in Example 19 was subjected to optical resolution using SFC (column used: Daicel Corporation CHIRALPAK ID (10 mm I. D.×250 mm L), mobile phase: $CO_2$:(0.1% DEA/MeOH)=95:5, flow rate: 30 mL/min, pressure: 100 bar, wavelength: 220 nm, column temperature: 35° C.). Under the above-mentioned optical resolution conditions, the optically active substances of the compound prepared in Example 19 were obtained in the first peak (retention time: about 4.62 minutes) and in the second peak (retention time: about 7.02 minutes), respectively.

Example 21: 1-[((3R)-6-butoxy-3-methyl-3,4-dihydronaphthalen-2-yl)methyl]azetidine-3-carboxylic acid and 1-[((3S)-6-butoxy-3-methyl-3,4-dihydronaphthalen-2-yl)methyl]azetidine-3-carboxylic acid

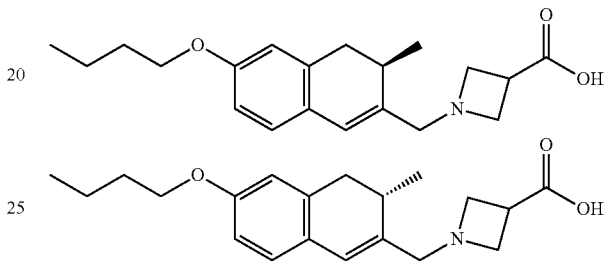

Each of the first peak compound (41 mg) or the second peak compound (38 mg) obtained by optical resolution in Example 20 was subjected to the same reaction as in Example 7 to give the title compounds (obtained from the first peak: 21 mg, obtained from the second peak: 19 mg) having the following physical property values.

Obtained from the First Peak $^1$H-NMR (CDCl$_3$): δ 6.96, 6.73-6.61, 6.45, 4.34, 4.24, 4.11, 4.05, 3.98-3.86, 3.60-3.38, 3.02, 2.62-2.48, 1.75, 1.48, 0.97, 0.91;

LCMS: Retention time 0.86 minutes.

Obtained from the Second Peak $^1$H-NMR (DMSO-$d_6$): δ 6.96, 6.71, 6.68, 6.24, 3.93, 3.60-2.90, 2.84, 2.34, 1.67, 1.43, 0.93, 0.85;

LCMS: Retention time 0.86 minutes.

Example 22: 5-fluoro-6-methoxy-3-methyl-3,4-dihydronaphthalen-1(2H)-one

To a solution of 6-methoxy-3-methyl-3,4-dihydronaphthalen-1(2H)-one (CAS Registry Number: 5563-21-3) (10.0 g) in acetonitrile (60 mL), Selectfluor (trade name) (21.6 g) was added, and the mixture was stirred at 40° C. for 25 hours. To the reaction liquid, water was added, and the mixture was extracted twice with ethyl acetate. The organic layer was washed with saturated saline, dried over sodium sulfate, and then concentrated under reduced pressure. The obtained residue was purified by silica gel column chromatography (hexane:ethyl acetate=10:0→8:2) to give a mixture (3.68 g) containing the title compound.

Example 23: 5-fluoro-6-methoxy-3-methyl-1,2,3,4-tetrahydronaphthalen-1-ol

To a solution of the mixture (3.68 g) prepared in Example 22 in methanol (35 mL), sodium borohydride (1.34 g) was added at 0° C., and the mixture was stirred at room temperature for 1.5 hours. To the reaction liquid, a saturated ammonium chloride aqueous solution was added, and the mixture was extracted with ethyl acetate. The organic layer was washed with saturated saline, dried over sodium sulfate, and then concentrated under reduced pressure. The obtained residue was directly used in the subsequent reaction in an unpurified state.

Example 24: 5-fluoro-6-methoxy-3-methyl-3,4-dihydronaphthalene-2-carbaldehyde To a solution of the compound (3.71 g) prepared in Example 23 in DMF (35 mL), phosphorus oxychloride (5.0 mL) was added, and the mixture was stirred at 70° C. for 16 hours. The reaction liquid was poured to a sodium hydroxide aqueous solution under ice cooling, and the mixture was stirred at room temperature for 30 minutes. After the mixture was extracted twice with ethyl acetate, the organic layer was washed with saturated saline, dried over sodium sulfate, and then concentrated under reduced pressure. The obtained residue was purified by silica gel column chromatography (hexane:ethyl acetate=10:0→7:3) to give the title compound (419 mg) having the following physical property values.
$^1$H-NMR (CDCl$_3$): δ 9.59, 7.15, 7.07, 6.83, 3.93, 3.11, 3.05, 2.78, 0.94.

Example 25: methyl 1-((5-fluoro-3-methyl-6-(4,4,4-trifluorobutoxy)-3,4-dihydronaphthalen-2-yl)methyl)azetidine-3-carboxylate The compound (460 mg) prepared in Example 24, methyl azetidine-3-carboxylate hydrochloride (226 mg), and 4,4,4-trifluorobutan-1-ol (84 mg) were used and subjected to the same reactions as in Example 13→Example 5→Example 8 to give the title compound (150 mg).
$^1$H-NMR (CDCl$_3$): δ 6.78-6.68, 6.22, 4.06, 3.72, 3.65-3.50, 3.43-3.22, 3.05, 2.85, 2.75, 2.50-2.25, 2.08, 0.94.

Example 26: (R)-methyl 1-((5-fluoro-3-methyl-6-(4,4,4-trifluorobutoxy)-3,4-dihydronaphthalen-2-yl)methyl)azetidine-3-carboxylate and (S)-methyl 1-((5-fluoro-3-methyl-6-(4,4,4-trifluorobutoxy)-3,4-dihydronaphthalen-2-yl)methyl)azetidine-3-carboxylate The compound prepared in Example 25 was subjected to optical resolution using SFC (column used: Daicel Corporation CHIRALPAK IC (10 mm×250 mm), mobile phase: CO$_2$:(0.1% DEA/EA)=95:5, flow rate: 30 mL/min, pressure: 100 bar, wavelength: 254 nm, column temperature: 35° C.). Under the above-mentioned optical resolution conditions, the optically active substances of Example 25 were obtained in the first peak (retention time: about 5.99 minutes) and in the second peak (retention time: about 7.67 minutes), respectively.

Example 27: (R)-1-[[5-fluoro-3-methyl-6-(4,4,4-trifluorobutoxy)-3,4-dihydronaphthalen-2-yl]methyl]azetidine-3-carboxylic acid and (S)-1-[[5-fluoro-3-methyl-6-(4,4,4-trifluorobutoxy)-3,4-dihydronaphthalen-2-yl]methyl]azetidine-3-carboxylic acid Each of the first peak compound (72 mg) or the second peak compound (52 mg) obtained by optical resolution in Example 26 was subjected to the same reaction as in Example 7 to give the title compounds (obtained from the first peak: 43 mg, obtained from the second peak: 39 mg) having the following physical property values.

The First Peak
$^1$H-NMR (CDCl$_3$): δ 6.80, 6.71, 6.47, 4.39, 4.30, 4.09-3.97, 3.91, 3.54, 3.44, 2.90, 2.81, 2.62, 2.33, 2.07, 0.94;
LCMS: Retention time 0.86 minutes.
The Second Peak
$^1$H-NMR (CDCl$_3$): δ 6.80, 6.71, 6.47, 4.38, 4.29, 4.09-3.97, 3.90, 3.53, 3.43, 2.90, 2.81, 2.62, 2.33, 2.07, 0.93;
LCMS: Retention time 0.85 minutes.

Example 28: 3-fluoro-1-[[5-fluoro-3-methyl-6-(4,4,4-trifluorobutoxy)-3,4-dihydronaphthalen-2-yl]methyl]azetidine-3-carboxylic acid The compound (370 mg) prepared in Example 24, 4,4,4-trifluorobutan-1-ol (124 mg), and methyl 3-fluoroazetidine-3-carboxylate hydrochloride (48.8 mg) were used and subjected to the same reactions as in Example 13→Example 8→Example 5→Example 7 to give the title compound (34.9 mg) having the following physical property values.
$^1$H-NMR (DMSO-d$_6$): δ 6.95-6.86, 6.32, 4.08, 3.80-2.89, 2.73, 2.47-2.37, 1.94, 0.87;
LCMS: Retention time 0.82 minutes.

Example 29: 2,4,6-triisopropylbenzenesulfonohydrazide

To a solution of 2,4,6-triisopropylbenzenesulfonyl chloride (CAS Registry Number: 6553-96-4) (10 g) in THF (30 mL), hydrazine hydrate (2.3 g) was gradually added at 0° C., and the mixture was stirred at 0° C. for 2 hours. To the reaction liquid, water was added, and the mixture was extracted twice with ethyl acetate. The organic layer was washed with saturated saline, dried over sodium sulfate, and then concentrated under reduced pressure. The obtained residue was washed with hexane, and then dried to give the title compound (7.1 g) having the following physical property values.
$^1$H-NMR (CDCl$_3$): δ 5.46, 4.18, 2.92, 1.30-1.24.

Example 30: (E)-2,4,6-triisopropyl-N'-(6-methoxy-3-methyl-3,4-dihydronaphthalen-1(2H)-ylidene)benzenesulfonohydrazide To a solution of 6-methoxy-3-methyl-3,4-dihydronaphthalen-1(2H)-one (CAS Registry Number: 5563-21-3) (4.0 g) in methanol (40 mL), the compound (7.0 g) prepared in Example 29 was added, and the mixture was stirred at room temperature for 72 hours. The reaction liquid was concentrated under reduced pressure, and the obtained residue was purified by silica gel column chromatography (NH silica gel, hexane:ethyl acetate=8:2→5:5) to give the title compound (4.2 g) having the following physical property values.
$^1$H-NMR (DMSO-d$_6$): δ 10.45, 7.69, 7.23, 6.72-6.67, 4.34, 3.73, 2.91, 2.84, 2.72, 2.40, 2.04-1.80, 1.26-1.17, 1.02.

Example 31: 4-fluoro-7-methoxy-2-methyl-1,2-dihydronaphthalene

To a solution of the compound (2.0 g) prepared in Example 30 in THF (21 mL), a hexane solution (6.0 mL) of 1.55 M n-butyllithium was added at 78° C., and the mixture was stirred at −78° C. for 30 minutes, and stirred at 0° C. for 20 minutes. After the mixture was cooled to −78° C. again, a THF solution (6.0 mL) of N-fluorobenzenesulfonimide (3.3 g) was added thereto, and the mixture was stirred at 78° C. for 30 minutes and stirred at room temperature for 18 hours. To the reaction liquid, a saturated sodium hydrogen carbonate aqueous solution was added, and the mixture was extracted twice with ethyl acetate. The organic layer was washed with saturated saline, dried over sodium sulfate, and then concentrated under reduced pressure. The obtained residue was purified by silica gel column chromatography (hexane:ethyl acetate=10:0→8:2) to give a mixture (550 mg) containing the title compound.

Example 32: 1-fluoro-6-methoxy-3-methyl-3,4-dihydronaphthalene-2-carbaldehyde

To a solution of the mixture (550 mg) prepared in Example 31 in DMF (5 mL), phosphorus oxychloride (1.2 g) was added, and the mixture was stirred at room temperature for 16 hours. To the reaction liquid, water was poured, and the mixture was extracted twice with ethyl acetate. The organic layer was washed with saturated saline, dried over sodium sulfate, and then concentrated under reduced pressure. The obtained residue was purified by silica gel column chromatography (hexane:ethyl acetate=10:0→7:3) to give the title compound (154 mg) having the following physical property values.
$^1$H-NMR (DMSO-$d_6$): δ 10.11, 7.59, 6.99, 6.96, 3.84, 3.10-2.95, 2.69, 0.86.

Example 33: 1-[[1-fluoro-3-methyl-6-(4,4,4-trifluorobutoxy)-3,4-dihydronaphthalen-2-yl]methyl]azetidine-3-carboxylic acid

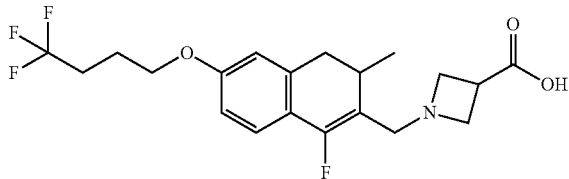 [SMILES: CC1Cc2cc(OCCCC(F)(F)F)ccc2C(F)=C1CN1CC(C(=O)O)C1]

The compound (150 mg) prepared in Example 32, methyl azetidine-3-carboxylate hydrochloride (64.1 mg), and 4,4,4-trifluorobutan-1-ol (8.2 mg) were used and subjected to the same reactions as in Example 13→Example 5→Example 8→Example 7 to give the title compound (8.1 mg) having the following physical property values.
$^1$H-NMR (DMSO-$d_6$): δ 7.22, 6.85, 6.81, 4.05, 3.60-3.00, 2.92, 2.42, 1.93, 0.89;
LCMS: Retention time 0.86 minutes.

Example 34: 1-bromo-6-methoxy-3-methyl-3,4-dihydronaphthalene-2-carbaldehyde

To a mixed solution of DCM (7.5 L) and DMF (1.5 L), phosphorus tribromide (1.5 L) was added dropwise at 0 to 5° C., and the mixture was stirred at 25 to 30° C. for 1 hour. A solution of 6-methoxy-3-methyl-3,4-dihydronaphthalen-1(2H)-one (CAS Registry Number: 5563-21-3) (750 g) in DCM (3.75 L) was added dropwise thereto at 25 to 30° C., and the mixture was heated at 90° C. for 1 hour. The reaction liquid was cooled to 25° C. and poured to crushed ice. The obtained solution was adjusted to pH 7 to 8 with a 2 N sodium hydroxide solution and extracted with DCM. The organic layer was washed with cold water, dried over sodium sulfate, and the solvent was distilled off. The obtained residue was purified by silica gel column chromatography to give the title compound (500 g) having the following physical property values.

$^1$H-NMR (CDCl$_3$): δ 10.18, 7.82, 6.82, 6.74, 3.85, 3.21, 3.07, 2.60, 0.84;

Example 35: 1-bromo-6-hydroxy-3-methyl-3,4-dihydronaphthalene-2-carbaldehyde

To a solution of the compound (525 g) prepared in Example 34 in DCM (4.2 L), a DCM solution (5.6 L) of 1 mol/L of boron tribromide was added dropwise at 10 to 20° C., and the mixture was stirred at 20 to 30° C. for 6 hours. The reaction solution was poured to ice-cold water, and the mixture was stirred for 30 minutes. After DCM was added to the reaction liquid, the organic layer was separated. The aqueous layer was extracted with DCM containing 10% methanol. The combined organic layer was washed with water, and dried over sodium sulfate, and then, the solvent was distilled off. The obtained residue was purified by silica gel column chromatography to give the title compound (350 g) having the following physical property values.
$^1$H-NMR (CDCl$_3$): δ 10.18, 7.81, 6.79, 6.67, 5.22, 3.22, 3.04, 2.58, 0.85.

Example 36: 6-hydroxy-1,3-dimethyl-3,4-dihydronaphthalene-2-carbaldehyde

To a solution of the compound (350 g) prepared in Example 35 in 1,4-dioxane (4.9 L), methyl boronic acid (235.2 g), potassium carbonate (726 g), and Rac BINAP (2,2'-bis(diphenylphosphino)-1,1'-binaphthyl, 40.78 g) were added under argon atmosphere, and the mixture was stirred for 30 minutes. After palladium acetate (17.64 g) was added thereto at 25 to 30° C., the reaction liquid was heated at 90° C. for 4 hours. The obtained reaction liquid was cooled to 25° C. and then poured to ice-cold water. The reaction liquid was filtered through Celite, followed by washing with ethyl acetate. The filtrate was adjusted to pH 2 to 3 with a 2 N hydrochloric acid solution, and the organic layer was separated. The aqueous layer was extracted with ethyl acetate. The combined organic layer was washed with saturated saline, and dried over sodium sulfate, and then, the solvent was distilled off. The obtained residue was purified by silica gel column chromatography to give the title compound (151 g) having the following physical property values.
$^1$H-NMR (DMSO-$d_6$): δ 10.21, 9.89, 7.48, 6.70, 6.65, 2.97, 2.81, 2.58-2.45, 2.44, 0.71.

Example 37: (R)-6-hydroxy-1,3-dimethyl-3,4-dihydronaphthalene-2-carbaldehyde and (S)-6-hydroxy-1,3-dimethyl-3,4-dihydronaphthalene-2-carbaldehyde The compound prepared in Example 36 was subjected to optical resolution using SFC (column used: Daicel Corporation CHIRALCEL OJ-H (30 mm×250 mm), mobile phase: CO$_2$:2-propanol=85:15, flow rate: 90 g/min, pressure: 100.0 bar, wavelength: 320 nm). The optically active substances of Example 36 obtained under the above-mentioned optical resolution conditions were analyzed by SFC (column used: Daicel Corporation CHIRALPAK-IG (46 mm×250 mm), mobile phase: CO$_2$:methanol=80:20, flow rate: 3 mL/min, pressure: 100 bar, wavelength: 214 nm, column temperature: 30° C.), and as a result, the retention times of the first peak and the second peak were 2.45 minutes and 4.77 minutes, respectively.

Example 38

1-[[(3R)-1,3-dimethyl-6-(4,4,4-trifluorobutoxy)-3,4-dihydronaphthalen-2-yl]methyl]azetidine-3-carboxylic acid or 1-[[(3S)-1,3-dimethyl-6-(4,4,4-trifluorobutoxy)-3,4-dihydronaphthalen-2-yl]methyl]azetidine-3-carboxylic acid

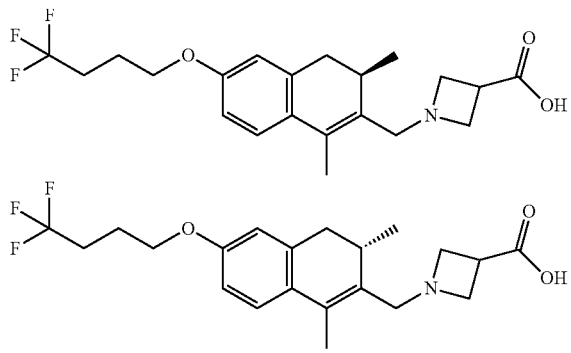

The optically active substance (1.0 g) in the first peak prepared in Example 37, methyl azetidine-3-carboxylate hydrochloride (970 mg), and 4,4,4-trifluorobutan-1-ol (85 mg) were used and subjected to the same reactions as in Example 5→Example 8→Example 7 to give the title compound (112 mg) having the following physical property values.

$^1$H-NMR (DMSO-$d_6$): δ 7.19, 6.77-6.72, 4.02, 3.90-2.88, 2.80, 2.48-2.36, 2.02, 1.92, 0.74;
LCMS: Retention time 0.81 minutes.

Example 39: (3S)-6-butoxy-3-methyl-3,4-dihydronaphthalene-2-carbaldehyde

The compound (300 mg) prepared in Example 14 (1) and 1-bromobutane (240 mg) were used and subjected to the same reaction as in Example 6 to give the title compound (351 mg) having the following physical property values.

$^1$H-NMR (DMSO-$d_6$): δ 9.54, 7.42, 7.37, 6.88, 6.85, 4.03, 3.01-2.84, 2.67, 1.71, 1.44, 0.94, 0.82;
LCMS: retention time 1.25 minutes.

Example 39 (1): (3R)-6-butoxy-3-methyl-3,4-dihydronaphthalene-2-carbaldehyde The compound prepared in Example 14 and 1-bromobutane were used and subjected to the same reaction as in Example 6 to give the title compound having the following physical property values.

$^1$H-NMR (DMSO-$d_6$): δ 9.54, 7.42, 7.37, 6.88, 6.85, 4.03, 3.01-2.84, 2.67, 1.71, 1.44, 0.94, 0.82;
LCMS: retention time 1.25 minutes.

Example 40: 1-{[(3S)-6-butoxy-3-methyl-3,4-dihydro-2-naphthalenyl]methyl}-3-methyl-3-azetidinecarboxylic acid The compound (55 mg) prepared in Example 39 and ethyl 3-methylazetidine-3-carboxylate (25 mg) were used and subjected to the same reactions as in Example 5→Example 7 to give the title compound (28.6 mg) having the following physical property values.

$^1$H-NMR (CD$_3$OD): δ 7.06, 6.78-6.70, 6.56, 4.40, 4.34, 4.07-3.94, 3.93-3.83, 3.04, 2.66, 2.42, 1.77, 1.60-1.46, 1.01, 0.96;
LCMS: Retention time 0.89 minutes.

Examples 40 (1) to (3)

The compound prepared in Example 39 or Example 39 (1) and ethyl azetidine-3-carboxylate or a corresponding amine derivative instead thereof were used and subjected to the same reactions as in Example 5→Example 7 to give the following compounds of Examples.

Example 40 (1)

1-{[(3R)-6-butoxy-3-methyl-3,4-dihydro-2-naphthalenyl]methyl}-3-methyl-3-azetidinecarboxylic acid $^1$H-NMR (CD$_3$OD): δ 7.06, 6.78-6.70, 6.56, 4.40, 4.34, 4.07-3.94, 3.93-3.83, 3.04, 2.66, 2.42, 1.77, 1.60-1.46, 1.01, 0.96;
LCMS: Retention time 0.89 minutes.

Example 40 (2): 1-{[(3S)-6-butoxy-3-methyl-3,4-dihydro-2-naphthalenyl]methyl}-3-methoxy-3-azetidinecarboxylic acid $^1$H-NMR (CD$_3$OD): δ 7.07, 6.78-6.70, 6.58, 4.46, 4.40, 4.23-4.06, 4.03-3.92, 3.36, 3.05, 2.66, 2.44, 1.77, 1.52, 1.01, 0.97;
LCMS: Retention time 0.88 minutes.

Example 40 (3): 1-{[(3R)-6-butoxy-3-methyl-3,4-dihydro-2-naphthalenyl]methyl}-3-methoxy-3-azetidinecarboxylic acid $^1$H-NMR (CD$_3$OD): δ 7.07, 6.78-6.70, 6.58, 4.46, 4.40, 4.23-4.06, 4.03-3.92, 3.36, 3.05, 2.66, 2.44, 1.77, 1.52, 1.01, 0.97;
LCMS: Retention time 0.88 minutes.

Example 41: (3S)-3-methyl-6-(4,4,4-trifluorobutoxy)-3,4-dihydronaphthalene-2-carbaldehyde The compound (312 mg) prepared in Example 14 (1) and 1-bromo-4,4,4-trifluorobutane (348 mg) were used and subjected to the same reaction as in Example 6 to give the title compound (502 mg) having the following physical property values.

$^1$H-NMR (DMSO-$d_6$): δ 9.55, 7.43, 7.39, 6.90, 6.87, 4.10, 3.02-2.85, 2.68, 2.47-2.35, 1.95, 0.82;
LCMS: retention time 1.13 minutes.

Example 41 (1): (3R)-3-methyl-6-(4,4,4-trifluorobutoxy)-3,4-dihydronaphthalene-2-carbaldehyde The compound prepared in Example 14 and 1-bromo-4,4,4-trifluorobutane were used and subjected to the same reaction as in Example 6 to give the title compound having the following physical property values.

$^1$H-NMR (DMSO-$d_6$): δ 9.55, 7.43, 7.39, 6.90, 6.87, 4.10, 3.02-2.85, 2.68, 2.47-2.35, 1.95, 0.82;
LCMS: retention time 1.13 minutes.

Example 42: 3-hydroxy-1-{[(3S)-3-methyl-6-(4,4,4-trifluorobutoxy)-3,4-dihydro-2-naphthalenyl]methyl}-3-azetidinecarboxylic acid The compound (50 mg) prepared in Example 41 and methyl 3-hydroxyazetidine-3-carboxylate hydrochloride (42 mg) were used and subjected to the same reactions as in Example 5→Example 7 to give the title compound (8.0 mg) having the following physical property values.

$^1$H-NMR (CD$_3$OD): δ 6.94, 6.69-6.60, 6.41, 4.22, 3.99-3.79, 2.92, 2.53, 2.38-2.17, 1.92, 0.85;

LCMS: Retention time 0.81 minutes.

Example 42 (1): 3-hydroxy-1-{[(3R)-3-methyl-6-(4,4,4-trifluorobutoxy)-3,4-dihydro-2-naphthalenyl]methyl}-3-azetidinecarboxylic acid The compound prepared in Example 41 (1) and methyl 3-hydroxyazetidine-3-carboxylate hydrochloride were used and subjected to the same reactions as in Example 5→Example 7 to give the title compound having the following physical property values.

$^1$H-NMR (CD$_3$OD): δ 6.94, 6.69-6.60, 6.41, 4.22, 3.99-3.79, 2.92, 2.53, 2.38-2.17, 1.92, 0.85; LCMS: retention time 0.81 minutes.

Example 43: tert-butyl N-{[(3S)-6-butoxy-3-methyl-3,4-dihydronaphthalen-2-yl]methyl}-N-methyl-β-alaninate The compound (55 mg) prepared in Example 39 and tert-butyl 3-(methylamino)propanoate (47 mg) were used and subjected to the same reaction as in Example 5 to give a mixture (23.9 mg) containing the title compound.

Example 43 (1): tert-butyl N-{[(3R)-6-butoxy-3-methyl-3,4-dihydronaphthalen-2-yl]methyl}-N-methyl-β-alaninate The compound prepared in Example 39 (1) and tert-butyl 3-(methylamino)propanoate were used and subjected to the same reaction as in Example 5 to give a mixture containing the title compound.

Example 44: 3-[{[(3S)-6-butoxy-3-methyl-3,4-dihydro-2-naphthalenyl]methyl}(methyl)amino]propanoic acid To a solution of the mixture (23.9 mg) prepared in Example 43 in dichloromethane (0.48 mL), trifluoroacetic acid (0.15 mL) was added, and the mixture was stirred at room temperature. After the reaction liquid was concentrated under reduced pressure, the obtained residue was purified by silica gel column chromatography (DCM:(DCM:methanol:concentrated ammonium hydroxide aqueous solution=80:18:2)=9:1→0:10) to give the title compound (12.0 mg) having the following physical property values.

$^1$H-NMR (CD$_3$OD): δ 7.04, 6.77-6.70, 6.57, 3.99, 3.85, 3.73, 3.32-3.24, 3.23-3.14, 3.10, 2.67, 2.59, 2.56-2.47, 1.77, 1.53, 1.04-0.97;

LCMS: Retention time 0.95 minutes.

Examples 44 (1) to (3)

The compound prepared in Example 39 or Example 39 (1) and tert-butyl 3-(methylamino)propanoate or a corresponding amine derivative instead thereof were used and subjected to the same reactions as in Example 5→Example 44 to give the following compounds of Examples.

Example 44 (1): 3-[{[(3R)-6-butoxy-3-methyl-3,4-dihydro-2-naphthalenyl]methyl}(methyl)amino]propanoic acid $^1$H-NMR (CD$_3$OD): δ 7.04, 6.77-6.70, 6.57, 3.99, 3.85, 3.73, 3.32-3.24, 3.23-3.14, 3.10, 2.67, 2.59, 2.56-2.47, 1.77, 1.53, 1.04-0.97;

LCMS: Retention time 0.95 minutes.

Example 44 (2): 3-({[(3S)-6-butoxy-3-methyl-3,4-dihydro-2-naphthalenyl]methyl}amino)propanoic acid $^1$H-NMR (CD$_3$OD): δ 7.06, 6.79-6.70, 6.62, 4.08-3.94, 3.71, 3.46-3.40, 3.28-3.17, 3.11, 2.87, 2.75-2.50, 1.77, 1.53, 1.05-0.94;

LCMS: Retention time 0.93 minutes.

Example 44 (3): 3-({[(3R-6-butoxy-3-methyl-3,4-dihydro-2-naphthalenyl]methyl}amino)propanoic acid $^1$H-NMR (CD$_3$OD): δ 7.06, 6.79-6.70, 6.62, 4.08-3.94, 3.71, 3.46-3.40, 3.28-3.17, 3.11, 2.87, 2.75-2.50, 1.77, 1.53, 1.05-0.94;

LCMS: Retention time 0.93 minutes.

Example 45: 1-[(3S)-3-methyl-6-(4,4,4-trifluorobutoxy)-3,4-dihydronaphthalen-2-yl]ethan-1-ol A solution of the compound (502 mg) prepared in Example 41 in THF (2.5 mL) was cooled to −78° C., a solution of 3 mol/L methylmagnesium chloride in THF (2.8 mL) was added thereto, and the mixture was stirred. To the reaction liquid, a saturated ammonium chloride aqueous solution was added, and the mixture was extracted with ethyl acetate. The organic layer was washed with saturated saline, dried over sodium sulfate, and then concentrated under reduced pressure. The obtained residue was purified by silica gel column chromatography (hexane:ethyl acetate=5:1→1:1) to give the title compound (410 mg) having the following physical property values.

$^1$H-NMR (DMSO-d$_6$): δ 7.02-6.95, 6.74, 6.70, 6.32, 6.23, 4.81, 4.74, 4.25-4.13, 4.10-3.94, 2.86, 2.45-2.31, 1.93, 1.26, 1.24, 0.88, 0.86.

Example 45 (1): 1-[(3R)-3-methyl-6-(4,4,4-trifluorobutoxy)-3,4-dihydronaphthalen-2-yl]ethan-1-ol The compound prepared in Example 41 (1) was used and subjected to the same reaction as in Example 45 to give the title compound having the following physical property values.

$^1$H-NMR (DMSO-d$_6$): δ 7.02-6.95, 6.74, 6.70, 6.32, 6.23, 4.81, 4.74, 4.25-4.13, 4.10-3.94, 2.86, 2.45-2.31, 1.93, 1.26, 1.24, 0.88, 0.86.

Example 46: 1-[(3S)-3-methyl-6-(4,4,4-trifluorobutoxy)-3,4-dihydronaphthalen-2-yl]ethan-1-one To a solution of the compound (410 mg) prepared in Example 45 in dichloromethane (4.1 mL), Dess-Martin periodinane (CAS Registry Number: 87413-09-0) (1.5 g) was added under ice-cooling, and the mixture was stirred at room temperature for 24 hours. To the reaction liquid, water was added, and the mixture was extracted with ethyl acetate. The organic layer was washed with a sodium thiosulfate aqueous solution, a saturated sodium hydrogen carbonate aqueous solution, and saturated saline, dried over sodium sulfate, and then concentrated under reduced pressure. The obtained residue was directly used in the subsequent reaction in an unpurified state.

Example 46 (1): 1-[(3R)-3-methyl-6-(4,4,4-trifluorobutoxy)-3,4-dihydronaphthalen-2-yl]ethan-1-one The compound prepared in Example 45 (1) was used and subjected to the same reaction as in Example 46 to give the title compound.

Example 47: 1-{1-[(3S)-3-methyl-6-(4,4,4-trifluorobutoxy)-3,4-dihydro-2-naphthalenyl]ethyl}-3-azetidinecarboxylic acid The compound (40 mg) prepared in Example 46 and methyl azetidine-3-carboxylate hydrochloride (39 mg) were used and subjected to the same reactions as in Example 5→Example 7 to give the title compound (14.2 mg) having the following physical property values.

$^1$H-NMR (DMSO-d$_6$): δ 7.03-6.95, 6.73, 6.72-6.66, 6.27, 6.25, 4.01, 3.50-2.99, 2.93-2.70, 2.46-2.28, 1.92, 1.07, 1.03, 0.89, 0.83;

LCMS: Retention time 0.96 minutes.

Examples 47 (1) to (3)

The compound prepared in Example 46 or Example 46 (1) and methyl azetidine-3-carboxylate hydrochloride or a corresponding amine derivative instead thereof were used and subjected to the same reactions as in Example 5→Example 7 to give the following compounds of Examples.

Example 47 (1): 1-{1-[(3R)-3-methyl-6-(4,4,4-trifluorobutoxy)-3,4-dihydro-2-naphthalenyl]ethyl}-3-azetidinecarboxylic acid $^1$H-NMR (DMSO-d$_6$): δ 7.03-6.95, 6.73, 6.72-6.66, 6.27, 6.25, 4.01, 3.50-2.99, 2.93-2.70, 2.46-2.28, 1.92, 1.07, 1.03, 0.89, 0.83;

LCMS: Retention time 0.96 minutes.

Example 47 (2): cis-3-({1-[(3S)-3-methyl-6-(4,4,4-trifluorobutoxy)-3,4-dihydro-2-naphthalenyl]ethyl}amino)cyclobutanecarboxylic acid

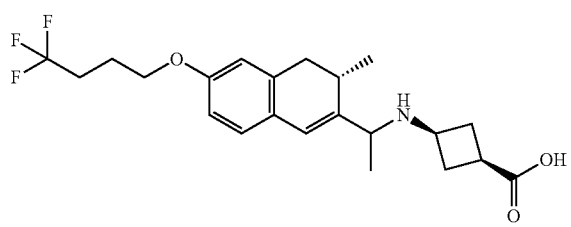 [SMILES: CC(N[C@H]1C[C@@H](C(=O)O)C1)C1=Cc2ccc(OCCCC(F)(F)F)cc2C[C@@H]1C]

$^1$H-NMR (CD$_3$OD): δ 7.07, 6.83-6.74, 6.62, 6.49, 4.07, 3.94-3.72, 3.20-3.03, 3.02-2.86, 2.75-2.26, 2.09-1.96, 1.57, 1.53, 1.00;

LCMS: Retention time 0.65 minutes.

Example 47 (3): cis-3-({1-[(3R)-3-methyl-6-(4,4,4-trifluorobutoxy)-3,4-dihydro-2-naphthalenyl]ethyl}amino)cyclobutanecarboxylic acid

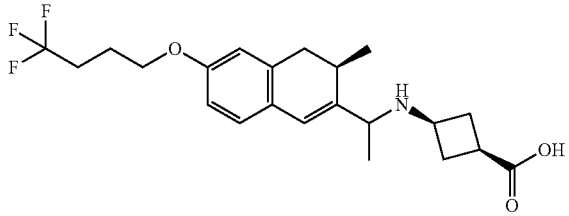 [SMILES: CC(N[C@H]1C[C@@H](C(=O)O)C1)C1=Cc2ccc(OCCCC(F)(F)F)cc2C[C@H]1C]

$^1$H-NMR (CD$_3$OD): δ 7.07, 6.83-6.74, 6.62, 6.49, 4.07, 3.94-3.72, 3.20-3.03, 3.02-2.86, 2.75-2.26, 2.09-1.96, 1.57, 1.53, 1.00;

LCMS: Retention time 0.65 minutes.

Example 48: 1-{[(3S)-6-butoxy-3-methyl-3,4-dihydronaphthalen-2-yl]methyl}azetidine-3-carbonitrile The compound (80 mg) prepared in Example 39 and azetidine-3-carbonitrile hydrochloride (CAS Registry Number: 345594-83-8) (58 mg) were used and subjected to the same reaction as in Example 5 to give the title compound (38 mg) having the following physical property values.

$^1$H-NMR (CDCl$_3$): δ 6.93, 6.70-6.64, 6.22, 3.95, 3.71-3.55, 3.39-3.24, 3.02, 2.95, 2.53, 2.39, 1.75, 1.49, 0.97, 0.93.

Example 48 (1): 1-{[(3R)-6-butoxy-3-methyl-3,4-dihydronaphthalen-2-yl]methyl}azetidine-3-carbonitrile The compound prepared in Example 39 (1) and azetidine-3-carbonitrile hydrochloride were used and subjected to the same reaction as in Example 5 to give the title compound having the following physical property values.

$^1$H-NMR (CDCl$_3$): δ 6.93, 6.70-6.64, 6.22, 3.95, 3.71-3.55, 3.39-3.24, 3.02, 2.95, 2.53, 2.39, 1.75, 1.49, 0.97, 0.93.

Example 49: 5-(1-{[(3S)-6-butoxy-3-methyl-3,4-dihydro-2-naphthalenyl]methyl}-3-azetidinyl)-1H-tetrazole To a solution of the compound (36 mg) prepared in Example 48 in toluene (2.0 mL), dibutyltin oxide (CAS Registry Number: 818-08-6) (87 mg) and trimethylsilyl azide (CAS Registry Number: 4648-54-8) (40 mg) were added, and the mixture was stirred at 110° C. for 4 hours. The reaction liquid was concentrated under reduced pressure, and the obtained residue was purified by silica gel column chromatography (Diol silica gel, dichloromethane:methanol=100:0→95:5) to give the title compound (5.0 mg) having the following physical property values.

$^1$H-NMR (CD$_3$OD): δ 6.94, 6.69-6.57, 6.48, 4.51-4.40, 4.40-4.13, 3.97, 3.90-3.81, 2.94, 2.55, 2.33, 1.65, 1.41, 0.92-0.84;

LCMS: Retention time 0.85 minutes.

Example 49 (1): 5-(1-{[(3R)-6-butoxy-3-methyl-3,4-dihydro-2-naphthalenyl]methyl}-3-azetidinyl)-1H-tetrazole The compound prepared in Example 48 (1) was used and subjected to the same reaction as in Example 49 to give the title compound having the following physical property values.

$^1$H-NMR (CD$_3$OD): δ 6.94, 6.69-6.57, 6.48, 4.51-4.40, 4.40-4.13, 3.97, 3.90-3.81, 2.94, 2.55, 2.33, 1.65, 1.41, 0.92-0.84;

LCMS: Retention time 0.85 minutes.

Example 50: methyl 1-{[(3S)-6-hydroxy-3-methyl-3,4-dihydronaphthalen-2-yl]methyl}azetidine-3-carboxylate The compound (1.0 g) prepared in Example 14 (1) and methyl azetidine-3-carboxylate hydrochloride (1.0 g) were used and subjected to the same reaction as in Example 5 to give the title compound (1.5 g) having the following physical property values.

$^1$H-NMR (DMSO-d$_6$): δ 9.24, 6.84, 6.53, 6.50, 6.16, 3.63, 3.48-3.24, 3.23-3.07, 2.92, 2.80, 2.43, 2.36-2.26, 0.85.

Example 50 (1): methyl 1-{[(3R)-6-hydroxy-3-methyl-3,4-dihydronaphthalen-2-yl]methyl}azetidine-3-carboxylate The compound prepared in Example 14 and methyl azetidine-3-carboxylate hydrochloride were used and subjected to the same reaction as in Example 5 to give the title compound having the following physical property values.

$^1$H-NMR (DMSO-d$_6$): δ 9.24, 6.84, 6.53, 6.50, 6.16, 3.63, 3.48-3.24, 3.23-3.07, 2.92, 2.80, 2.43, 2.36-2.26, 0.85.

Example 51: methyl 1-({(3S)-3-methyl-6-[(trifluoromethanesulfonyl)oxy]-3,4-dihydronaphthalen-2-yl}methyl)azetidine-3-carboxylate To a solution of the compound (1250 mg) prepared in Example 50 in dichloromethane (12.5 mL), diisopropylethylamine (2.3 mL) and N-phenylbis(trifluoromethanesulfonimide) (CAS Registry Number: 37595-74-7) (1.7 g) were added under ice cooling, and the mixture was stirred at room temperature for 24 hours. To the reaction liquid, water was added, and the mixture was extracted with ethyl acetate. The organic layer was washed with saturated saline, dried over sodium sulfate, and then concentrated under reduced pressure. The obtained residue was purified by silica gel column chromatography (hexane:ethyl acetate=7:3→5:5) to give the title compound (1630 mg) having the following physical property values.

$^1$H-NMR (CDCl$_3$): δ 7.09-6.98, 6.26, 3.64-3.52, 3.41-3.25, 3.08, 3.00, 2.60, 2.43, 0.94.

Example 51 (1): methyl 1-({(3R)-3-methyl-6-[(trifluoromethanesulfonyl)oxy]-3,4-dihydronaphthalen-2-yl}methyl)azetidine-3-carboxylate The compound prepared in Example 50 (1) was used and subjected to the same reaction as in Example 51 to give the title compound having the following physical property values.

$^1$H-NMR (CDCl$_3$): δ 7.09-6.98, 6.26, 3.64-3.52, 3.41-3.25, 3.08, 3.00, 2.60, 2.43, 0.94.

Example 52: methyl 1-({(3S)-6-[butyl(methyl)amino]-3-methyl-3,4-dihydronaphthalen-2-yl}methyl)azetidine-3-carboxylate To a solution of the compound (50 mg) prepared in Example 51 in 1,4-dioxane (0.5 mL), N-methylbutylamine (13.5 mg), cesium carbonate (51 mg), XPhos (11 mg), and dibenzylideneacetone dipalladium (5.5 mg) were added, and the mixture was stirred at 80° C. for 16 hours. To the reaction liquid, ethyl acetate was added, and the mixture was filtered through amino silica, and the filtrate was concentrated. The obtained residue was purified by silica gel column chromatography (NH$_2$ silica gel, hexane:ethyl acetate=1:2) to give a mixture containing the title compound.

Example 52 (1): methyl 1-({(3R)-6-[butyl(methyl)amino]-3-methyl-3,4-dihydronaphthalen-2-yl}methyl)azetidine-3-carboxylate The compound prepared in Example 51 (1) and N-methylbutylamine were used and subjected to the same reaction as in Example 52 to give a mixture containing the title compound.

Example 53: 1-({(3S)-6-[butyl(methyl)amino]-3-methyl-3,4-dihydro-2-naphthalenyl}methyl)-3-azetidinecarboxylic acid The mixture (21 mg) prepared in Example 52 was used and subjected to the same reaction as in Example 7 to give the title compound (4.4 mg) having the following physical property values.

$^1$H-NMR (DMSO-d$_6$): δ 6.84, 6.46, 6.42, 6.14, 3.50-3.07, 3.00-2.87, 2.86, 2.84-2.76, 2.52, 2.47-2.42, 2.35-2.22, 1.47, 1.30, 0.90, 0.85;

LCMS: Retention time 0.79 minutes.

Example 53 (1): 1-({(3R)-6-[butyl(methyl)amino]-3-methyl-3,4-dihydro-2-naphthalenyl}methyl)-3-azetidinecarboxylic acid The mixture prepared in Example 52 (1) was used and subjected to the same reaction as in Example 7 to give the title compound having the following physical property values.

$^1$H-NMR (DMSO-d$_6$): δ 6.84, 6.46, 6.42, 6.14, 3.50-3.07, 3.00-2.87, 2.86, 2.84-2.76, 2.52, 2.47-2.42, 2.35-2.22, 1.47, 1.30, 0.90, 0.85;

LCMS: Retention time 0.79 minutes.

Example 54: methyl 1-{[(3S)-6-(butylsulfanyl)-3-methyl-3,4-dihydronaphthalen-2-yl]methyl}azetidine-3-carboxylate To a solution of the compound (150 mg) prepared in Example 51 in 1,4-dioxane (1.5 mL), 1-butanethiol (64.5 mg), diisopropylethylamine (0.15 mL), Xantphos (41 mg), and dibenzylideneacetone dipalladium (33 mg) were added, and the mixture was stirred at 100° C. for 24 hours. The reaction liquid was filtered through Celite, and the filtrate was concentrated under reduced pressure. The obtained residue was purified by silica gel column chromatography (hexane:ethyl acetate=8:2→5:5) to give the title compound (83 mg) having the following physical property values.

$^1$H-NMR (CDCl$_3$): δ 7.09, 7.06, 6.93, 6.23, 3.71, 3.65-3.52, 3.42-3.22, 3.04, 2.96, 2.90, 2.53, 2.40, 1.68-1.56, 1.51-1.37, 0.97-0.88.

Example 54 (1): methyl 1-{[(3R)-6-(butylsulfanyl)-3-methyl-3,4-dihydronaphthalen-2-yl]methyl}azetidine-3-carboxylate The compound prepared in Example 51 (1) and 1-butanethiol were used and subjected to the same reaction as in Example 54 to give the title compound having the following physical property values.
$^1$H-NMR (CDCl$_3$): δ 7.09, 7.06, 6.93, 6.23, 3.71, 3.65-3.52, 3.42-3.22, 3.04, 2.96, 2.90, 2.53, 2.40, 1.68-1.56, 1.51-1.37, 0.97-0.88;

Example 55: 1-{[(3S)-6-(butylthio)-3-methyl-3,4-dihydro-2-naphthalenyl]methyl}-3-azetidinecarboxylic acid The compound (77 mg) prepared in Example 54 was used and subjected to the same reaction as in Example 7 to give the title compound (57 mg) having the following physical property values.
$^1$H-NMR (DMSO-d$_6$): δ 7.10-7.04, 7.00, 6.27, 3.55-3.17, 3.05, 2.94, 2.86, 2.57-2.52, 2.42-2.31, 1.55, 1.40, 0.88, 0.85;
LCMS: Retention time 0.98 minutes.

Example 55 (1): 1-{[(3R)-6-(butylthio)-3-methyl-3,4-dihydro-2-naphthalenyl]methyl}-3-azetidinecarboxylic acid The compound prepared in Example 54 (1) was used and subjected to the same reaction as in Example 7 to give the title compound having the following physical property values.
$^1$H-NMR (DMSO-d$_6$): δ 7.10-7.04, 7.00, 6.27, 3.55-3.17, 3.05, 2.94, 2.86, 2.57-2.52, 2.42-2.31, 1.55, 1.40, 0.88, 0.85;
LCMS: Retention time 0.98 minutes.

Example 56: methyl 1-{[(3S)-3-methyl-6-pentyl-3,4-dihydronaphthalen-2-yl]methyl}azetidine-3-carboxylate To a solution of the compound (95 mg) prepared in Example 51 in a mixed solution of 1,4-dioxane (1.0 mL), tetrahydrofuran (0.95 mL) and water (0.19 mL), pentylboronic acid (31.5 mg), cesium carbonate (221 mg), and 1,1'-bis(diphenylphosphino)ferrocene-palladium (II) dichloride dichloromethane adduct (18.5 mg) were added, and the mixture was stirred at 90° C. for 19 hours. To the reaction liquid, saturated saline was added, and the mixture was extracted with ethyl acetate. The organic layer was washed with a 5% potassium carbonate aqueous solution, dried over sodium sulfate, and then concentrated under reduced pressure. The obtained residue was purified by silica gel column chromatography (hexane:ethyl acetate=6:4→4:6) to give a mixture (23 mg) containing the title compound.
LCMS: retention time 1.01 minutes.

Example 56 (1): methyl 1-{[(3R)-3-methyl-6-pentyl-3,4-dihydronaphthalen-2-yl]methyl}azetidine-3-carboxylate The compound prepared in Example 51 (1) and pentylboronic acid were used and subjected to the same reaction as in Example 56 to give a mixture containing the title compound.
LCMS: retention time 1.01 minutes.

Example 57: 1-{[(3S)-3-methyl-6-pentyl-3,4-dihydro-2-naphthalenyl]methyl}-3-azetidinecarboxylic acid The compound (23 mg) prepared in Example 56 was used and subjected to the same reaction as in Example 7 to give the title compound (10.7 mg) having the following physical property values.
$^1$H-NMR (DMSO-d$_6$): δ 6.97-6.92, 6.25, 3.50-3.15, 3.02, 2.86, 2.48-2.44, 2.40-2.29, 1.54, 1.17-1.21, 0.90-0.82;
LCMS: Retention time 1.00 minutes.

Examples 57 (1) to (5)

The compound prepared in Example 51 or Example 51 (1) and pentylboronic acid or a corresponding boronic acid derivative instead thereof were used and subjected to the same reactions as in Example 56→Example 7 to give the following compounds of Examples.

Example 57 (1): 1-{[(3R)-3-methyl-6-pentyl-3,4-dihydro-2-naphthalenyl]methyl}-3-azetidinecarboxylic acid $^1$H-NMR (DMSO-d$_6$): δ 6.97-6.92, 6.25, 3.50-3.15, 3.02, 2.86, 2.48-2.44, 2.40-2.29, 1.54, 1.17-1.21, 0.90-0.82;
LCMS: Retention time 1.00 minutes.

Example 57 (2): 1-{[(3S)-3-methyl-6-(propoxymethyl)-3,4-dihydro-2-naphthalenyl]methyl}-3-azetidinecarboxylic acid $^1$H-NMR (DMSO-d$_6$): δ 7.09-7.05, 7.02, 6.27, 4.38, 3.50-3.10, 2.98, 2.88, 2.52, 2.46-2.32, 1.54, 0.88, 0.86;
LCMS: Retention time 0.89 minutes.

Example 57 (3): 1-{[(3R)-3-methyl-6-(propoxymethyl)-3,4-dihydro-2-naphthalenyl]methyl}-3-azetidinecarboxylic acid $^1$H-NMR (DMSO-d$_6$): δ 7.09-7.05, 7.02, 6.27, 4.38, 3.50-3.10, 2.98, 2.88, 2.52, 2.46-2.32, 1.54, 0.88, 0.86;
LCMS: Retention time 0.89 minutes.

Example 57 (4): 1-{[(3S)-6-(2-ethoxyethyl)-3-methyl-3,4-dihydro-2-naphthalenyl]methyl}-3-azetidinecarboxylic acid $^1$H-NMR (CDCl$_3$): δ 7.05-6.95, 6.50, 4.55-4.08, 3.92, 3.69, 3.60, 3.49, 3.00, 2.83, 2.57, 2.49, 1.19, 0.91;
LCMS: Retention time 0.86 minutes.

Example 57 (5): 1-{[(3R)-6-(2-ethoxyethyl)-3-methyl-3,4-dihydro-2-naphthalenyl]methyl}-3-azetidinecarboxylic acid $^1$H-NMR (CDCl$_3$): δ 7.05-6.95, 6.50, 4.55-4.08, 3.92, 3.69, 3.60, 3.49, 3.00, 2.83, 2.57, 2.49, 1.19, 0.91;
LCMS: Retention time 0.86 minutes.

Comparative Example: (S)-3-fluoro-1-[(6-methoxy-3-methyl-3,4-dihydronaphthalen-2-yl)methyl]azetidine-3-carboxylic acid The compound (300 mg) prepared in Example 14 (1), methyl 3-fluoroazetidine-3-carboxylate hydrochloride (297 mg), and methanol (6.3 mg) were used and subjected to the same reactions as in Example 5→Example 8→Example 7 to give the title compound (17 mg) having the following physical property values.

$^1$H-NMR (DMSO-d$_6$): δ 6.99, 6.71, 6.68, 6.27, 3.82-3.64, 3.63-3.35, 3.30-3.15, 2.86, 2.52, 2.36, 0.85;

LCMS: Retention time 0.65 minutes.

Hereinafter, Biological Experimental Examples will be shown, and the effects of the compounds of the present invention were confirmed based on these experimental methods.

Biological Experimental Example 1: Evaluation of SIP Receptor Agonist Activity of Compounds of the Present Invention by Monitoring Intracellular Calcium Concentration Chinese hamster ovary (CHO) cells in which each of a human S1P$_1$ (EDG-1) gene or a human S1P$_5$ (EDG-8) gene was overexpressed were cultured in Ham's F-12 medium containing 10% FBS (fetal bovine serum), penicillin/streptomycin, and geneticin (0.25 mg/mL). The culture medium was replaced one day before performing a calcium assay and on the day of the assay. Four hours after the culture medium replacement, the culture medium was removed, and washing was performed once with phosphate-buffered saline. After the cells were detached by adding 0.05% trypsin EDTA, the cells were recovered by adding a culture medium. The recovered cell suspension was centrifuged to remove the supernatant, and the cells were suspended in phosphate-buffered saline, and the cell number was counted. The cells were suspended in a Hanks solution containing Calcium 6 Assay Reagent (manufactured by Molecular Devices, LLC), 20 mM HEPES, and 2.5 mM probenecid at a cell density of 1.1×10$^6$ cells/mL, and the suspension was incubated at 37° C. for about 1 hour. Thereafter, the supernatant was removed by centrifugation, and the cells were suspended in a Hanks solution containing 20 mM HEPES, 2.5 mM probenecid, and 0.1% BSA at a cell density of 2.2×10$^6$ cells/mL. The suspension was inoculated in a 96-well plate at 80 μL/well. The plate was set on a fluorescent drug screening system (FDSS 6000), and the compound and S1P were sequentially added thereto, and an increase in intracellular calcium concentration between before and after the addition was measured at an excitation wavelength of 480 nm and a fluorescence wavelength of 540 nm. The increase in intracellular calcium concentration was evaluated by the signal intensity at the fluorescence wavelength, and the agonist activity of each compound was calculated by assuming the signal intensity when S1P was added instead of the compound to be 100% activity.

[Results]

The agonist activities (EC$_{50}$ values) of the compounds of the present invention against S1P$_1$ receptor or S1P$_5$ receptor are shown in Table 1. Further, other than Comparative Example described in the present specification as Comparative Compound, as Comparative Compound A, 1-{[1-methyl-6-(octyloxy)-3,4-dihydro-2-naphthalenyl]methyl}-3-azetidinecarboxylic acid hydrochloride described in Example 31 (58) of Patent Literature 1, and as Comparative Compound B, 1-({6-[(2-methoxy-4-propylbenzyl)oxy]-1-methyl-3,4-dihydro-2-naphthalenyl}methyl)-3-azetidinecarboxylic acid described in Example 37 of Patent Literature 2 were used. Comparative Example did not have S1P$_1$ and S1P$_5$ receptor agonist activities. Comparative Compound A and Comparative Compound B have both S1P$_1$ and S1P$_5$ receptor agonist activities, and the S1P$_1$ receptor agonist activity was stronger than the S1P$_5$ receptor agonist activity. On the other hand, it was found that each compounds of the present invention have a selective agonist activity against S1P$_5$ receptor, and the balance of an S1P$_5$ receptor agonist activity against an S1P$_1$ receptor agonist activity is improved.

TABLE 1

| | Agonist Activity EC$_{50}$ (nmol/L) | |
|---|---|---|
| Compound | S1P$_1$ | S1P$_5$ |
| Comparative Example | >10000 | >10000 |
| Comparative Compound A | <3 | 3 |
| Comparative Compound B | 0.2 | 2 |
| Example 15 | >3000 | 3 |
| Example 18* | >30000 | 11 |
| Example 18 | >30000 | 21 |
| Example 21* | >3000 | 23 |
| Example 21 | >3000 | 250 |
| Example 15 (34) | >3000 | 20 |
| Example 15 (52) | >3000 | 15 |
| Example 15 (70) | >3000 | 12 |
| Example 15 (72) | >3000 | 22 |
| Example 15 (82) | >30000 | 9 |
| Example 15 (86) | >30000 | 26 |
| Example 47 (2) | >30000 | 1100 |
| Example 57 (2) | >30000 | 98 |

*Obtained from the first peak

Biological Experimental Example 2: Measurement of Clearance in Rats

A compound solution was administered into the tail vein of fasted male SD rats. After the administration, the rats were held by hand, and the blood was collected by adding heparin sodium from the cervical vein at regular intervals. The blood was centrifuged at 10,000 g for 3 minutes at 4° C. to obtain plasma. The concentration of the compound in the plasma was measured by LC/MS/MS. A clearance was calculated from the change in plasma concentration using a pharmacokinetic analysis software Phoenix WinNonlin (Certara USA, Inc.).

[Results]

Since the compounds of the present invention have a low clearance, high bioavailability can be expected.

Biological Experimental Example 3: Measurement of Inhibitory Action of Comparative Compound C on Binding of [$^{33}$P]-S1P to S1P$_5$ (EDG-8)

A reaction was carried out in a 96-well microplate by using a membrane fraction of Chinese hamster ovary (CHO) cells each of which was made to overexpress human S1P$_1$ (EDG-1) gene or human S1P$_5$ gene respectively, in an amount of the membrane fraction of 60 μg protein/mL. To each of the well, 100 μL of a vehicle (DMSO) solution or a compound solution at a two-fold concentration each diluted with Binding Buffer (50 mmol/L Tris pH 7.5, 5 mmol/L MgCl$_2$, 0.5% BSA, Complete EDTA free (1 tablet/50 mL)) and 50 μL of 0.16 nmol/L [$^{33}$P]-S1P (manufactured by American Radiolabeled Chemicals, Inc.) diluted with Binding Buffer were added, and thereafter, the membrane fraction solution (50 μL) was added thereto, and a reacted was allowed to proceed at room temperature for 60 minutes. After the reaction, suction filtration was carried out by using a 96-well Unifilter, followed by washing with a washing buffer (50 mmol/L Tris pH 7.5, 0.5% BSA) (150 mL), and then dried at 50 to 60° C. for 30 to 60 minutes. MicroScint (trade name) 20 (50 μL/well) was added thereto, and the plate was covered with TopSeal-A, and then a radioactivity was measured with TopCount (manufactured by PerkinElmer Co., Ltd.)

[Evaluation]

The compound concentration at which 50% of the specific binding of [$^{33}$P]-S1P to human S1P$_1$ and human S1P$_5$ was replaced (IC$_{50}$ value) was used as an evaluation item. The specific binding amount was determined by subtracting the mean amount (cpm) of [$^{33}$P]-S1P nonspecific binding from that of the [$^{33}$P]-S1P total binding, vehicle, or compound treatment. The specific binding amount of [$^{33}$P]-S1P was assumed to be 100%, and a relative value (%) of the specific binding amount at each concentration of the compound was calculated. Among the treatment concentrations of the vehicle or the compound exhibiting a relative value (%) of 25 to 75%, a treatment concentration at which a relative value closest to 50% was exhibited was selected, and the IC$_{50}$ value was calculated by substituting the relative value (%) and the treatment concentration for Y and X, respectively, in the following formula.

$$Y=100/(1+10^{X-logIC50})$$

[Results]

As Comparative Compound C, 3-({[6-(3-cyclohexylpropoxy)-1-methyl-3,4-dihydro-2-naphthalenyl]methyl}amino)propanoic acid hydrochloride described in Example 31 (45) of Patent Literature 1 was used. Comparative Compound C exhibited an inhibitory activity (IC$_{50}$ value) of 1.0 nmol/L or 8.5 nmol/L for binding of [$^{33}$P]-S1P to S1P$_1$ or S1P$_5$, respectively.

Biological Experimental Example 4: Effectiveness in Mouse Experimental Autoimmune Encephalomyelitis Model Female C57BL/J mice (Charles River Laboratories Japan, Inc., age at start of experiment: at 7 or 8 weeks of age) were used. Myelin Oligoendendyte Glycoprotein [sequence 35-55 MEVGWYRSPFSRVVHLYRNGK (AnaSpec, Inc., hereinafter referred to as MOG 35-55)] was dissolved in physiological saline (Otsuka Pharmaceutical Factory Co., Ltd.) to prepare a 2 mg/mL solution. The 2 mg/mL solution of MOG 35-55 and an equal amount of FCA H37Ra (Difco Laboratories) were mixed to prepare an emulsion, and the emulsion was used as an inducing agent. An immunization treatment was carried out by subcutaneously administering 0.2 mL of the inducing agent into the flank of the mouse using a glass syringe equipped with a 26G injection needle. The immunization treatment day was determined as day 0 of immunization, and 0.2 mL of a 1 µg/mL solution of Pertussis toxin (List Biological Laboratories) was administered into the tail vein on day 0 and day 2 of immunization (see Cell Mol Immunol, Vol. 2, pp. 439-448, 2005).

On the day before the immunization treatment, the body weight was measured, and the mice were evenly divided into groups so that no significant difference was observed in the average value of the body weight among the respective groups. After dividing into groups, administration of a test substance (the compound of the present invention), a positive control compound (FTY720: fingolimod), or a vehicle (a 0.5 w/v % methylcellulose 400 cP solution) was started on the same day, and each test substance was repetitively orally administered once a day for 30 days from the day before the immunization treatment to day 28 of immunization. The amount of the solution to be administered was calculated based on the body weight of each animal on the administration day.

In the evaluation of the neurological symptom, the degree of paralysis was assigned a score which was used as a neurological symptom score (0: normal, 1: flaccid tail, 2: paresis of hind limbs, 3: paralysis of hind limbs, 4: quadriplegia, 5: near-death). The observation period was determined to be the day before the immunization treatment and each day between day 5 to day 29 of immunization, and observation was carried out before administering the test substance or the like (see Proc. Natl. Acad. Sci. USA, Vol. 103, pp. 13451-13456, 2006).

[Results]

The compounds of the present invention exhibit effectiveness in this model.

PREPARATION EXAMPLES

Preparation Example 1

By mixing the following components in a conventional manner and tableting, about 10,000 tablets each containing 10 mg of the active ingredient are obtained.

| | |
|---|---|
| 1-[((3S)-3-methyl-6-pentoxy-3,4-dihydronaphthalen-2-yl)methyl]azetidine-3-carboxylic acid | 100 g |
| Carboxymethyl cellulose calcium (a disintegrating agent) | 20 g |
| Magnesium stearate (a lubricant) | 10 g |
| Microcrystalline cellulose | 870 g |

Preparation Example 2

The following components were mixed in a conventional manner. Thereafter, the mixture is filtered through a dust filter, and 5 ml aliquots are charged into ampules. The ampules are heat sterilized by an autoclave to give 10,000 ampules each containing 20 mg of the active component.

| | |
|---|---|
| 3-fluoro-1-[[(3S)-3-methyl-6-[(E)-4,4,4-trifluorobut-2-enoxy]-3,4-dihydronaphthalen-2-yl]methyl]azetidine-3-carboxylic acid | 200 g |
| Mannitol | 20 g |
| Distilled water | 50 L |

INDUSTRIAL APPLICABILITY

The compound of the present invention has a selective S1P$_5$ receptor agonist activity, and therefore, is useful for treating an S1P$_5$-mediated disease, for example, neurodegenerative disease and the like.

The invention claimed is:

1. A compound or a pharmaceutically acceptable salt thereof, wherein the compound is 1-[[(3S)-3-methyl-6-(4,4,4-trifluorobutoxy)-3,4-dihydronaphthalen-2-yl]methyl]azetidine-3-carboxylic acid, or a pharmaceutically acceptable salt thereof.

2. A compound of the following structure:

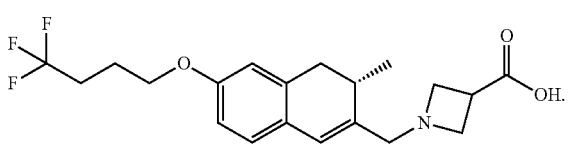 [SMILES: C[C@H]1Cc2cc(OCCCC(F)(F)F)ccc2C=C1CN1CC(C(=O)O)C1]

3. A pharmaceutically acceptable salt of the compound of the following structure:
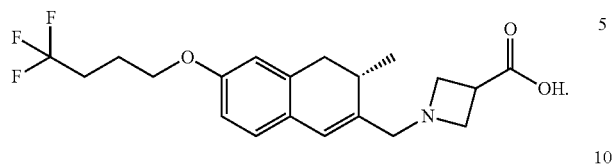
* * * * *

UNITED STATES PATENT AND TRADEMARK OFFICE
CERTIFICATE OF CORRECTION

PATENT NO. : 11,198,672 B2
APPLICATION NO. : 16/970865
DATED : December 14, 2021
INVENTOR(S) : Toshihide Watanabe et al.

Page 1 of 1

It is certified that error appears in the above-identified patent and that said Letters Patent is hereby corrected as shown below:

On the Title Page

Page 2, Column 1, Line 3, Item [56] delete "PCT/JP2 015/084019." and insert --PCT/JP2015/084019.-- therefor;

Page 2, Column 1, Line 5, Item [56] delete "relatedt" and insert --related-- therefor; and Page 2, Column 1, Line 6, Item [56] delete "PCT/JP2 015/084019." and insert --PCT/JP2015/084019.-- therefor.

In the Claims

Claim 1, Column 76, Lines 56-57, delete ", or a pharmaceutically acceptable salt thereof".

Signed and Sealed this
Twenty-third Day of August, 2022

Katherine Kelly Vidal
*Director of the United States Patent and Trademark Office*